United States Patent
Wyrich et al.

(10) Patent No.: US 11,525,155 B2
(45) Date of Patent: *Dec. 13, 2022

(54) STABILISATION OF BIOLOGICAL SAMPLES

(71) Applicant: QIAGEN GmbH, Hilden (DE)

(72) Inventors: Ralf Wyrich, Hilden (DE); Thorsten Voss, Leverkusen (DE); Kalle Günther, Hilden (DE); Uwe Oelmüller, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,902

(22) PCT Filed: Mar. 18, 2014

(86) PCT No.: PCT/EP2014/000725
§ 371 (c)(1),
(2) Date: Sep. 17, 2015

(87) PCT Pub. No.: WO2014/146781
PCT Pub. Date: Sep. 25, 2014

(65) Prior Publication Data
US 2016/0348151 A1    Dec. 1, 2016

Related U.S. Application Data

(60) Provisional application No. 61/803,107, filed on Mar. 18, 2013.

(30) Foreign Application Priority Data

Mar. 25, 2013 (EP) ..................................... 13160896
Aug. 12, 2013 (EP) ..................................... 13180130

(51) Int. Cl.
C12Q 1/6806 (2018.01)
C12Q 1/6841 (2018.01)
C12N 15/10 (2006.01)

(52) U.S. Cl.
CPC ........... *C12Q 1/6806* (2013.01); *C12N 15/10* (2013.01); *C12N 15/1003* (2013.01); *C12Q 1/6841* (2013.01)

(58) Field of Classification Search
CPC .................................................. C12N 15/10
See application file for complete search history.

(56) References Cited

U.S. PATENT DOCUMENTS

| | | | |
|---|---|---|---|
| 3,389,133 A | 6/1968 | Gutcho | |
| 3,903,179 A | 9/1975 | Bacha et al. | |
| 4,555,487 A * | 11/1985 | Yamada | C12N 1/20 435/129 |
| 4,938,961 A | 7/1990 | Collins et al. | |
| 5,459,073 A | 10/1995 | Ryan | |
| 5,460,797 A | 10/1995 | Ryan | |
| 5,705,628 A | 1/1998 | Hawkins | |
| 5,811,268 A | 9/1998 | Geri et al. | |
| 5,860,397 A | 1/1999 | Schafer | |
| 5,898,071 A | 4/1999 | Hawkins | |
| 6,379,930 B1 | 4/2002 | Dattagupta et al. | |
| 6,407,107 B1 | 6/2002 | Gilbert et al. | |
| 6,479,267 B1 | 11/2002 | Davis et al. | |
| 6,534,262 B1 | 3/2003 | McKernan et al. | |
| 6,602,718 B1 | 8/2003 | Augello et al. | |
| 6,617,170 B2 | 9/2003 | Augello et al. | |
| 6,673,364 B1 | 1/2004 | Holland et al. | |
| 6,776,959 B1 | 8/2004 | Helftenbein | |
| 7,270,953 B2 | 9/2007 | Holländer et al. | |
| 7,332,277 B2 | 2/2008 | Dhallan | |
| 7,442,506 B2 | 10/2008 | Dhallan | |
| 8,569,477 B2 | 10/2013 | Finne | |
| 9,006,419 B2 | 4/2015 | Jiang et al. | |
| 2002/0081619 A1 | 6/2002 | Bastian et al. | |
| 2003/0064000 A1 | 4/2003 | Burgess et al. | |
| 2003/0118980 A1 | 6/2003 | Taylor | |
| 2004/0004523 A1 | 1/2004 | Humphries et al. | |
| 2004/0043505 A1 | 3/2004 | Walenciak et al. | |
| 2004/0167165 A1 | 8/2004 | Shankar et al. | |
| 2004/0191703 A1 | 9/2004 | Soper et al. | |
| 2004/0214175 A9 | 10/2004 | McKernan et al. | |
| 2004/0253661 A1 | 12/2004 | Goldrick et al. | |
| 2005/0158699 A1 | 7/2005 | Kadkade et al. | |
| 2005/0208510 A1 | 9/2005 | Latham et al. | |
| 2006/0014177 A1 | 1/2006 | Hogan et al. | |
| 2006/0141465 A1 | 6/2006 | Tanga et al. | |
| 2006/0147944 A1 | 7/2006 | Chomczynski | |

(Continued)

FOREIGN PATENT DOCUMENTS

| | | |
|---|---|---|
| AU | 2011253662 A1 | 12/2011 |
| EP | 0 578 885 A2 | 1/1994 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802. (Year: 1995).*

Baechler et al., "Expression levels for many genes in human peripheral blood cells are highly sensitive to ex vivo incubation," *Genes and Immunity* 5:347-353 (2004).

Caserta et al., "Q-VD-Oph, a broad spectrum caspase inhibitor with potent antiapoptotic properties," *Apoptosis* 8(4):345-351 (2003).

Chiu et al., "Effects of Blood-Processing Protocols on Fetal and Total DNA Quantification in Maternal Plasma," *Clinical Chemistry* 47(9):1607-1613 (2001).

DeAngelis et al., "Solid-phase reversible immobilization for the isolation of PCR products," *Nucleic Acids Research* 23(22):4742-4743 (1995).

(Continued)

*Primary Examiner* — Marcos L Sznaidman
(74) *Attorney, Agent, or Firm* — Seed IP Law Group LLP

(57) ABSTRACT

The present invention provides methods and composition suitable for stabilizing cell-containing samples such as blood samples. The stabilizers used are primary or secondary carboxylic acid amides.

20 Claims, 25 Drawing Sheets

Specification includes a Sequence Listing.

(56) References Cited

U.S. PATENT DOCUMENTS

| | | |
|---|---|---|
| 2006/0212020 A1* | 9/2006 | Rainen .................... A01N 1/02 604/403 |
| 2007/0190535 A1 | 8/2007 | Hall, Jr. et al. |
| 2007/0208166 A1 | 9/2007 | Baly et al. |
| 2008/0132694 A1 | 6/2008 | Himmelreich et al. |
| 2008/0176209 A1 | 7/2008 | Muller et al. |
| 2008/0187924 A1 | 8/2008 | Korfhage et al. |
| 2008/0257207 A1 | 10/2008 | Rengaswamy et al. |
| 2009/0017438 A1 | 1/2009 | Roy et al. |
| 2009/0017439 A1 | 1/2009 | Shimko et al. |
| 2009/0042301 A1 | 2/2009 | Owttrim et al. |
| 2009/0274765 A1 | 11/2009 | Beduneau et al. |
| 2010/0009349 A1 | 1/2010 | Holländer |
| 2010/0137575 A1 | 6/2010 | Connolly et al. |
| 2010/0184069 A1 | 7/2010 | Fernando et al. |
| 2010/0209930 A1 | 8/2010 | Fernando |
| 2010/0255524 A1* | 10/2010 | Hollander .......... C12N 15/1003 435/29 |
| 2010/0280233 A1 | 11/2010 | Connolly et al. |
| 2010/0285468 A1 | 11/2010 | Xin |
| 2010/0311166 A1 | 12/2010 | Florio et al. |
| 2011/0111410 A1 | 5/2011 | Ryan et al. |
| 2011/0306668 A1 | 12/2011 | Yu et al. |
| 2012/0064021 A1 | 3/2012 | Leplanquais et al. |
| 2012/0253071 A1 | 10/2012 | Fau et al. |
| 2013/0078625 A1* | 3/2013 | Holmes .............. G01N 35/0092 435/6.11 |
| 2013/0323793 A1 | 12/2013 | Tanner et al. |
| 2014/0227687 A1 | 8/2014 | Horlitz et al. |
| 2014/0227688 A1 | 8/2014 | Horlitz et al. |
| 2015/0056604 A1 | 2/2015 | Sehgal |

FOREIGN PATENT DOCUMENTS

| | | |
|---|---|---|
| EP | 0 880 537 B1 | 12/1998 |
| EP | 1 859 038 B1 | 8/2010 |
| EP | 2 256 196 A1 | 12/2010 |
| GB | 2 496 969 A | 5/2013 |
| JP | 2009-521949 A | 6/2009 |
| JP | 2009-522542 A | 6/2009 |
| JP | 2011-109987 A | 6/2011 |
| WO | 95/21849 A1 | 8/1995 |
| WO | 97/34015 A1 | 9/1997 |
| WO | 97/35589 A1 | 10/1997 |
| WO | 98/05767 A1 | 2/1998 |
| WO | WO 98/29126 * | 7/1998 |
| WO | WO 1998/29126 * | 7/1998 |
| WO | 98/41651 A1 | 9/1998 |
| WO | 99/57318 A2 | 11/1999 |
| WO | 01/60517 A2 | 8/2001 |
| WO | 01/70279 A1 | 9/2001 |
| WO | 02/066993 A1 | 8/2002 |
| WO | 03/018757 A2 | 3/2003 |
| WO | 03/040687 A2 | 5/2003 |
| WO | 03/086480 A1 | 10/2003 |
| WO | 2004/024958 A1 | 3/2004 |
| WO | 2004/032750 A1 | 4/2004 |
| WO | 2004/051272 A1 | 6/2004 |
| WO | 2004/072228 A2 | 8/2004 |
| WO | 2005/021748 A1 | 3/2005 |
| WO | 2005/067388 A2 | 7/2005 |
| WO | 2005/081867 A2 | 9/2005 |
| WO | 2006/017295 A2 | 2/2006 |
| WO | 2006/097806 A1 | 9/2006 |
| WO | 2007/077199 A2 | 7/2007 |
| WO | 2007/077560 A2 | 7/2007 |
| WO | WO 2007/077560 * | 12/2007 |
| WO | 2008/145710 A1 | 12/2008 |
| WO | 2009/016255 A1 | 2/2009 |
| WO | 2010/096323 A1 | 8/2010 |
| WO | WO 2010/096323 * | 8/2010 |
| WO | 2011/026027 A1 | 3/2011 |
| WO | 2011/026028 A1 | 3/2011 |
| WO | 2011/057061 A1 | 5/2011 |
| WO | 2011/057184 A1 | 5/2011 |
| WO | 2011/157678 A1 | 12/2011 |
| WO | 2012/151450 A1 | 11/2012 |
| WO | 2013/045432 A1 | 4/2013 |
| WO | 2013/045434 A1 | 4/2013 |
| WO | 2013/045457 A1 | 4/2013 |
| WO | 2013/045458 A1 | 4/2013 |
| WO | 2013/053855 A1 | 4/2013 |
| WO | 2014/049022 A1 | 4/2014 |
| WO | 2014/055936 A1 | 4/2014 |
| WO | 2014/131906 A1 | 9/2014 |
| WO | 2014/146780 A1 | 9/2014 |
| WO | 2014/146782 A1 | 9/2014 |
| WO | 2015/140218 A1 | 9/2015 |
| WO | 2016/022433 A1 | 2/2016 |

OTHER PUBLICATIONS

Fan et al., "Analysis of the Size Distributions of Fetal and Maternal Cell-Free DNA by Paired-End Sequencing," *Clinical Chemistry* 56(8):1-8 (2010).

Fleischhacker et al., "Circulating nucleic acids (CNAs) and cancer—A survey," *Biochimica et Biophysica Acta* 1775:181-232 (2007).

Fleischhacker, "Biology of Circulating mRNA—Still More Questions Than Answers?" *Ann. N.Y. Acad. Sci.* 1075:40-49 (2006).

Hromadnikova et al., "Quantification of Fetal and Total Circulatory DNA in Maternal Plasma Samples Before and After Size Fractionation by Agarose Gel Electrophoresis," *DNA and Cell Biology* 25(11):635-640 (2006).

Kruhøffer et al., "Isolation of Microarray-Grade Total RNA, MicroRNA, and DNA from a Single PAXgene Blood RNA Tube," *Journal of Molecular Diagnostics* 9(4):452-458 (Sep. 2007).

Lis et al., "Size fractionation of double-stranded DNA by precipitation with polyethylene glycol," *Nucleic Acids Research* 2(3):383-389 (Mar. 1975).

Pahl et al., "Gene expression changes in blood after phlebotomy: implications for gene expression profiling," *Blood* 100(3):1-2 (Aug. 1, 2002).

Rainen et al., "Stabilization of mRNA Expression in Whole Blood Samples," *Clinical Chemistry* 48(11):1883-1890 (2002).

Swarup et al., "Circulating (cell-free) nucleic acids—A promising, non-invasive tool for early detection of several human diseases," *FEBS Letters* 581:795-799 (2007).

U.S. Appl. No. 14/777,878, filed Sep. 17, 2015, Stabilization and Isolation of Extracellular Nucleic Acids.

U.S. Appl. No. 14/777,882, filed Sep. 17, 2015, Stabilization and Isolation of Extracellular Nucleic Acids.

U.S. Appl. No. 15/125,863, filed Sep. 13, 2016, Stabilization and Isolation of Extracellular Nucleic Acids.

U.S. Appl. No. 14/430,824, filed Mar. 24, 2015, Stabilisation of Biological Samples.

U.S. Appl. No. 14/347,048, filed Mar. 25, 2014, Stabilization and Isolation of Extracellular Nucleic Acids.

U.S. Appl. No. 14/347,051, filed Aug. 7, 2014, Stabilization and Isolation of Extracellular Nucleic Acids.

Anonymous, "Caspase Inhibitor," BD™ ApoBlock—Technical Data Sheet (2 pages) (2008).

Dupuis et al., "Molecular-crowding effects on single-molecule RNA folding/unfolding thermodynamics and kinetics," *PANS* 111(23):8464-8469 (Jun. 10, 2014).

Ekert et al., "Caspase inhibitors," *Cell Death and Differentiation* 6:1081-1086, 1999.

Fernando et al., "Preservation and Amplification of Fetal Cell-Free DNA in Maternal Plasma for Noninvasive Prenatal Diagnosis," *Streck*, First Presented at AACC/ASCLS Clinical Lab Expo on Jul. 23, 2009.

Fernando et al., "Stabilization of Cell-Free RNA in Plasma for Noninvasive Diagnosis," *Streck*, Presented at AACC Annual Meeting Jul. 2010, Anaheim, CA.

Goldstein et al., "Caspase-independent cytochrome c release is a sensitive measure of low-level apoptosis in cell culture models," *Aging Cell* 4(4):217-222 (2005).

(56) References Cited

OTHER PUBLICATIONS

Jani et al., "Caspase Inhibition Prevents the Increase in Caspase-3, -2, -8 and -9 Activity and Apoptosis in the Cold Ischemic Mouse Kidney," *American Journal of Transplantation* 4:1246-1254, 2004.
Karimata et al., "Stabilization of a DNA duplex under molecular crowding conditions of PEG," *Nucleic Acids Symposium Series No. 48*:107-108 (2004).
Ke et al., "Characterizing DNA Condensation and Conformational Changes in Organic Solvents," *PLoS ONE* 5(10):e13308, 2010, 8 pages.
MP Biomedicals, "Q-VD-OPH (OPH109), anew generation broad spectrum caspase inhibitor from innovators of Z-VAD(OMe)-FMK Caspase Inhibitor / Apoptosis Inhibitor," downloaded from https://www.mpbio.com/detailed_info.php?family_key=03OPH109&country=223 on Sep. 5, 2017, 5 pages.
Mukae et al., "Molecular cloning and characterization of human caspase-activated DNase," Proc. Natl. Acad. Sci. USA 95:9123-9128 (1998).
Müller et al., "Improvement of molecular monitoring of residual disease in leukemias by bedside RNA stabilization," *Leukemia16*:2395-2399 (2002).
Notice of Reasons for Refusal with English Translation, dated Jun. 1, 2016, for Japanese Application No. 2014-532357, 11 pages.
Paithankar et al., "Precipitation of DNA by polyethylene glycol and ethanol," Nucleic Acids Research 19(6):1346 (Feb. 6, 1991).
QIAamp® Circulating Nucleic Acid Handbook, QIAGEN®—Sample & Assay Technologies (44 pages) (May 2009).
Samejima et al., "Trashing the Genome: The Role of Nucleases During Apoptosis," *Nature Reviews* 6:677-688, 2005.
Sethu et al., "Microfluidic Isolation of Leukocytes from Whole Blood for Phenotype and Gene Expression Analysis," *Anal. Chem.* 76:5453-5461 (2006).
Decision of Rejection corresponding to Chinese Patent Application No. 201280046949.4, English Translation, 3 pages, dated May 25, 2018.
Xu, "Guidance Book of Malignant Tumor Chemotherapy and Strategies Thereof for National Self-Taught Higher Education Examinations for Chinese Medicine Majors," (Bachelor) with Partial English Translation, 7 pages, (2002).
Zhao et al., "*Collection of Essays at 60th Anniversary of Animal Society of China for Commemorating 100th Anniversary of Professor Chen Zhen's Birth*," with Partial English Translation, 6 pages, (1994).
Marino et al., "Lysosomal and mitochondrial permeabilization mediates zinc(II) cationic phthalocyanine phototoxicity," The International loumal of Biochemistry & Cell Biology 45:2553-2562 (2013).

Mosbah et al., "Effects of Polyethylene Glycol and Hydroxyethyl Starch in University of Wisconsin Preservation Solution on Human Red Blood Cell Aggregation and Viscosity," Transplantation Proceedings 38:1229-1235 (2006).
BD Pharmingen, Technical Data Sheet, "Z-VAD-FMK, General Caspase Inhibitor," (2 pages) (2008).
Japan Becton, Dickinson and Company sterilizes all vacuum blood collection tubes., Japan BD [online], 2 pages, Jun. 11, 2015, [retrieved on Dec. 16, 2020], URL, https://web.archive.org/web/20150611101224https://www.bdj.co.jp/pas/articles/1f3pro000000pyeu.html.
Japanese Office Action dated Dec. 17, 2020 corresponding to Japanese Patent Application No. 2018-525690, 15 pages, with translation.
Katsue Kikuchi, et al., Shinkuu saiketsukan wo mochiita yori anzenna saiketsuhou wo mezashite [Aiming for a safer blood collection method using a vacuum blood collection tube] (Final Version), Clinical Test News, 2 pages, 2006, No. 17.
Sinkuu Saiketsukan [Vacuum blood collection tube], Nipro, 2 pages, May 2015.
Ahmad et al., "Modification of standard proteinase K/phenol method for DNA isolation to improve yield and from frozen blood," *J Med Genet* 32:129-130 (1995).
Boese et al., "In vitro selection and characterization of cellulose-binding DNA aptamers," *Nucleic Acids Research* 35(19):6378-6388 (2007).
DYEnamic ET Dye Terminator Cycle Sequencing Kit for MegaBACE DNA Analysis Systems, Amersham Biosciences, 40 pages, (2002).
Elkin et al., "Magnetic Bead Purification of Labeled DNA Fragments for High-Throughput Capillary Electrophoresis Sequencing," *Biotechniques* 32(6):1296-1302 (Jun. 2002).
Finn et al., "Synthesis and application of charge-modified dye-labeled dideoxynucleoside-5'-triphosphates to 'direct-load' DNA sequencing," *Nucleic Acids Research*, 30(13):2877-2885 (2002).
Ruiz-Martinez et al., "A Sample Purification Method for Rugged and High-Performance DNA Sequencing by Capillary Electrophoresis Using Replaceable Polymer Solutions. A. Development of the Cleanup Protocol," *Anal. Chem.* 70:1516-1527 (1998).
Sephadex® G-25 media and pre-packed cols. Desalting/buffer exchange and gel filtration, Data File, Pharmacia Biotech (1996).
Tabor et al., "DNA sequence analysis with a modified bacteriophage T7 Dna polymerase," *Proc. Natl. Aca. Sci. USA* 84:4767-4771 (Jul. 1987).
Xu et al., "Solid-Phase Reversible Immobilization in Microfluidic Chips for the Purification of Dye-Labeled DNA Sequencing Fragments," *Anal. Chem.* 75:2975-2984 (2003).

\* cited by examiner

SEQUENCE LISTING

```
<160> NUMBER OF SEQ ID NOS: 83

<210> SEQ ID NO 1
<211> LENGTH: 5
<212> TYPE: PRT
<213> ORGANISM: Unknown
<220> FEATURE:
<223> OTHER INFORMATION: Bax-Inhibiting peptide, V5

<400> SEQUENCE: 1

Val Pro Met Leu Lys
1               5

<210> SEQ ID NO 2
<211> LENGTH: 6
<212> TYPE: PRT
<213> ORGANISM: Unknown
<220> FEATURE:
<223> OTHER INFORMATION: STAT3 Inhibitor peptide
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (2)..(2)
<223> OTHER INFORMATION: PHOSPHORYLATION

<400> SEQUENCE: 2

Pro Tyr Leu Lys Thr Lys
1               5

<210> SEQ ID NO 3
<211> LENGTH: 4
<212> TYPE: PRT
<213> ORGANISM: Artificial
<220> FEATURE:
<223> OTHER INFORMATION: Group III Caspase Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 3

Ile Glu Pro Asp
1

<210> SEQ ID NO 4
<211> LENGTH: 4
<212> TYPE: PRT
<213> ORGANISM: Artificial
<220> FEATURE:
<223> OTHER INFORMATION: Caspase 3, 7 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 4

Asp Glu Val Asp
1

<210> SEQ ID NO 5
<211> LENGTH: 4
<212> TYPE: PRT
<213> ORGANISM: Artificial
<220> FEATURE:
<223> OTHER INFORMATION: Caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
```

-continued

```
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 5

Leu Glu Thr Asp
1

<210> SEQ ID NO 6
<211> LENGTH: 4
<212> TYPE: PRT
<213> ORGANISM: Artificial
<220> FEATURE:
<223> OTHER INFORMATION: Caspase 1, 4 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 6

Tyr Val Ala Asp
1

<210> SEQ ID NO 7
<211> LENGTH: 4
<212> TYPE: PRT
<213> ORGANISM: Artificial
<220> FEATURE:
<223> OTHER INFORMATION: Caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 7

Ala Glu Val Asp
1

<210> SEQ ID NO 8
<211> LENGTH: 4
<212> TYPE: PRT
<213> ORGANISM: Artificial
<220> FEATURE:
<223> OTHER INFORMATION: Caspase 12 inhibitor
<220> FEATURE:
<221> NAME/KEY: MOD_RES
<222> LOCATION: (1)..(1)
```

```
<223> OTHER INFORMATION: BLOCKED
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 8

Ala Thr Ala Asp
1

<210> SEQ ID NO 9
<211> LENGTH: 4
<212> TYPE: PRT
<213> ORGANISM: Artificial
<220> FEATURE:
<223> OTHER INFORMATION: Caspase 4 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 9

Leu Glu Val Asp
1

<210> SEQ ID NO 10
<211> LENGTH: 4
<212> TYPE: PRT
<213> ORGANISM: Artificial
<220> FEATURE:
<223> OTHER INFORMATION: Caspase 13 inhibitor, reversible
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 10

Leu Glu Glu Asp
1

<210> SEQ ID NO 11
<211> LENGTH: 4
<212> TYPE: PRT
<213> ORGANISM: Artificial
<220> FEATURE:
<223> OTHER INFORMATION: Caspase 13 inhibitor, irreversible
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
```

<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 11

Leu Glu Glu Asp
1

<210> SEQ ID NO 12
<211> LENGTH: 4
<212> TYPE: PRT
<213> ORGANISM: Artificial
<220> FEATURE:
<223> OTHER INFORMATION: inhibitor of anti-APO-1 induced apoptosis in
      L929-APO-1 cells
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 12

Tyr Val Ala Asp
1

<210> SEQ ID NO 13
<211> LENGTH: 20
<212> TYPE: PRT
<213> ORGANISM: Artificial
<220> FEATURE:
<223> OTHER INFORMATION: Caspase 1 Inhibitor I, cell-permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 13

Ala Ala Val Ala Leu Leu Pro Ala Val Leu Leu Ala Leu Leu Ala Pro
1               5                   10                  15

Tyr Val Ala Asp
            20

<210> SEQ ID NO 14
<211> LENGTH: 4
<212> TYPE: PRT
<213> ORGANISM: Artificial
<220> FEATURE:
<223> OTHER INFORMATION: Caspase 1 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)

```
<223> OTHER INFORMATION: BLOCKED

<400> SEQUENCE: 14

Tyr Val Ala Asp
1

<210> SEQ ID NO 15
<211> LENGTH: 4
<212> TYPE: PRT
<213> ORGANISM: Artificial
<220> FEATURE:
<223> OTHER INFORMATION: Caspase 1 inhibitor IV, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 15

Tyr Val Ala Asp
1

<210> SEQ ID NO 16
<211> LENGTH: 4
<212> TYPE: PRT
<213> ORGANISM: Artificial
<220> FEATURE:
<223> OTHER INFORMATION: Caspase 1 Inhibitor VI, cell permeable
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 16

Tyr Val Ala Asp
1

<210> SEQ ID NO 17
<211> LENGTH: 5
<212> TYPE: PRT
<213> ORGANISM: Artificial
<220> FEATURE:
<223> OTHER INFORMATION: Caspase 2 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (5)..(5)
<223> OTHER INFORMATION: BLOCKED

<400> SEQUENCE: 17
```

Val Asp Val Ala Asp
1               5

<210> SEQ ID NO 18
<211> LENGTH: 5
<212> TYPE: PRT
<213> ORGANISM: Artificial
<220> FEATURE:
<223> OTHER INFORMATION: Caspase 2 Inhibitor II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 18

Leu Asp Glu Ser Asp
1               5

<210> SEQ ID NO 19
<211> LENGTH: 4
<212> TYPE: PRT
<213> ORGANISM: Artificial
<220> FEATURE:
<223> OTHER INFORMATION: Caspase 3 Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 19

Asp Glu Val Asp
1

<210> SEQ ID NO 20
<211> LENGTH: 20
<212> TYPE: PRT
<213> ORGANISM: Artificial
<220> FEATURE:
<223> OTHER INFORMATION: Caspase 3 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 20

Ala Ala Val Ala Leu Leu Pro Ala Val Leu Leu Ala Leu Leu Ala Pro
1               5                   10                  15

Asp Glu Val Asp
            20

<210> SEQ ID NO 21
<211> LENGTH: 4
<212> TYPE: PRT
<213> ORGANISM: Artificial
<220> FEATURE:
<223> OTHER INFORMATION: Caspase 3 Inhibitor II
<220> FEATURE:
<221> NAME/KEY: MOD_RES
<222> LOCATION: (1)..(1)

```
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 21

Asp Glu Val Asp
1

<210> SEQ ID NO 22
<211> LENGTH: 4
<212> TYPE: PRT
<213> ORGANISM: Artificial
<220> FEATURE:
<223> OTHER INFORMATION: Caspase 3 Inhibitor III
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 22

Asp Glu Val Asp
1

<210> SEQ ID NO 23
<211> LENGTH: 4
<212> TYPE: PRT
<213> ORGANISM: Artificial
<220> FEATURE:
<223> OTHER INFORMATION: Caspase 3 Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 23

Asp Met Gln Asp
1

<210> SEQ ID NO 24
<211> LENGTH: 4
<212> TYPE: PRT
<213> ORGANISM: Artificial
<220> FEATURE:
<223> OTHER INFORMATION: Caspase 3 Inhibitor V
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
```

```
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 24

Asp Gln Met Asp
1

<210> SEQ ID NO 25
<211> LENGTH: 4
<212> TYPE: PRT
<213> ORGANISM: Artificial
<220> FEATURE:
<223> OTHER INFORMATION: Caspase 4 Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 25

Leu Glu Val Asp
1

<210> SEQ ID NO 26
<211> LENGTH: 20
<212> TYPE: PRT
<213> ORGANISM: Artificial
<220> FEATURE:
<223> OTHER INFORMATION: Caspase 4 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 26

Ala Ala Val Ala Leu Leu Pro Ala Val Leu Leu Ala Leu Leu Ala Pro
1               5                   10                  15

Leu Glu Val Asp
            20

<210> SEQ ID NO 27
<211> LENGTH: 4
<212> TYPE: PRT
<213> ORGANISM: Artificial
<220> FEATURE:
<223> OTHER INFORMATION: Caspase 5 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
```

```
<220> FEATURE:
<221> NAME/KEY: MOD_RES
<222> LOCATION: (4)..(4)
<223> OTHER INFORMATION: BLOCKED

<400> SEQUENCE: 27

Trp Glu His Asp
1

<210> SEQ ID NO 28
<211> LENGTH: 4
<212> TYPE: PRT
<213> ORGANISM: Artificial
<220> FEATURE:
<223> OTHER INFORMATION: Caspase 6 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 28

Val Glu Ile Asp
1

<210> SEQ ID NO 29
<211> LENGTH: 20
<212> TYPE: PRT
<213> ORGANISM: Artificial
<220> FEATURE:
<223> OTHER INFORMATION: Caspase 6 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 29

Ala Ala Val Ala Leu Leu Pro Ala Val Leu Leu Ala Leu Leu Ala Pro
1               5                   10                  15

Val Glu Ile Asp
            20

<210> SEQ ID NO 30
<211> LENGTH: 20
<212> TYPE: PRT
<213> ORGANISM: Artificial
<220> FEATURE:
<223> OTHER INFORMATION: Caspase 8 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED
```

```
<400> SEQUENCE: 30

Ala Ala Val Ala Leu Leu Pro Ala Val Leu Leu Ala Leu Leu Ala Pro
1               5                   10                  15

Ile Glu Thr Asp
            20

<210> SEQ ID NO 31
<211> LENGTH: 4
<212> TYPE: PRT
<213> ORGANISM: Artificial
<220> FEATURE:
<223> OTHER INFORMATION: Caspase 8 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 31

Ile Glu Thr Asp
1

<210> SEQ ID NO 32
<211> LENGTH: 4
<212> TYPE: PRT
<213> ORGANISM: Artificial
<220> FEATURE:
<223> OTHER INFORMATION: Caspase 9 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 32

Leu Glu His Asp
1

<210> SEQ ID NO 33
<211> LENGTH: 20
<212> TYPE: PRT
<213> ORGANISM: Artificial
<220> FEATURE:
<223> OTHER INFORMATION: Caspase 9 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (20)..(20)
<223> OTHER INFORMATION: BLOCKED

<400> SEQUENCE: 33

Ala Ala Val Ala Leu Leu Pro Ala Val Leu Leu Ala Leu Leu Ala Pro
1               5                   10                  15

Leu Glu His Asp
            20

<210> SEQ ID NO 34
<211> LENGTH: 4
<212> TYPE: PRT
<213> ORGANISM: Artificial
<220> FEATURE:
<223> OTHER INFORMATION: Caspase 9 Inhibitor III
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 34

Leu Glu His Asp
1

<210> SEQ ID NO 35
<211> LENGTH: 19
<212> TYPE: PRT
<213> ORGANISM: Artificial
<220> FEATURE:
<223> OTHER INFORMATION: Pan-Caspase Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: BLOCKED

<400> SEQUENCE: 35

Ala Ala Val Ala Leu Leu Pro Ala Val Leu Leu Ala Leu Leu Ala Pro
1               5                   10                  15

Val Ala Asp

<210> SEQ ID NO 36
<211> LENGTH: 5
<212> TYPE: PRT
<213> ORGANISM: Artificial
<220> FEATURE:
<223> OTHER INFORMATION: Caspase Inhibitor VIII
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 36

Val Asp Val Ala Asp
1               5

<210> SEQ ID NO 37
<211> LENGTH: 4
```

```
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 37

Tyr Val Ala Asp
1

<210> SEQ ID NO 38
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 38

Trp Glu His Asp
1

<210> SEQ ID NO 39
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 39

Tyr Val Ala Asp
1

<210> SEQ ID NO 40
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED
```

```
<400> SEQUENCE: 40

Tyr Val Ala Asp
1

<210> SEQ ID NO 41
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 41

Tyr Val Ala Asp
1

<210> SEQ ID NO 42
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 42

Tyr Val Lys Asp
1

<210> SEQ ID NO 43
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 43

Tyr Val Ala Asp
1

<210> SEQ ID NO 44
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 44

Val Asp Val Ala Asp
1               5

<210> SEQ ID NO 45
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: BLOCKED
<220> FEATURE:
<221> NAME/KEY: MOD_RES
<222> LOCATION: (5)..(5)
<223> OTHER INFORMATION: METHYLATION

<400> SEQUENCE: 45

Val Asp Val Ala Asp
1               5

<210> SEQ ID NO 46
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 46

Glu Ser Met Asp
1

<210> SEQ ID NO 47
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 47
```

Ile Glu Thr Asp
1

<210> SEQ ID NO 48
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 48

Asp Glu Val Asp
1

<210> SEQ ID NO 49
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 49

Asp Met Gln Asp
1

<210> SEQ ID NO 50
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 50

Asp Gln Met Asp
1

<210> SEQ ID NO 51
<211> LENGTH: 4
<212> TYPE: PRT
<213> ORGANISM: Artificial

```
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 51

Asp Glu Val Asp
1

<210> SEQ ID NO 52
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 52

Asp Glu Val Asp
1

<210> SEQ ID NO 53
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 53

Leu Glu Val Asp
1

<210> SEQ ID NO 54
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
```

```
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 54

Tyr Val Ala Asp
1

<210> SEQ ID NO 55
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 55

Val Glu Ile Asp
1

<210> SEQ ID NO 56
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 56

Val Glu Ile Asp
1

<210> SEQ ID NO 57
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 57
```

```
Ile Glu Pro Asp
1

<210> SEQ ID NO 58
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 58

Ala Glu Val Asp
1

<210> SEQ ID NO 59
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 59

Ile Glu Thr Asp
1

<210> SEQ ID NO 60
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 60
```

```
Leu Glu Thr Asp
1

<210> SEQ ID NO 61
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 61

Leu Glu His Asp
1

<210> SEQ ID NO 62
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 62

Leu Glu His Asp
1

<210> SEQ ID NO 63
<211> LENGTH: 4
<212> TYPE: PRT
<213> ORGANISM: Artificial
<220> FEATURE:
<223> OTHER INFORMATION: caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 63

Ala Glu Val Asp
1

<210> SEQ ID NO 64
<211> LENGTH: 4
<212> TYPE: PRT
<213> ORGANISM: Artificial
<220> FEATURE:
<223> OTHER INFORMATION: Granzyme B Inhibitor II
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: BLOCKED

<400> SEQUENCE: 64

Ile Glu Thr Asp
1

<210> SEQ ID NO 65
<211> LENGTH: 4
<212> TYPE: PRT
<213> ORGANISM: Artificial
<220> FEATURE:
<223> OTHER INFORMATION: Granzyme B Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 65

Ile Glu Pro Asp
1

<210> SEQ ID NO 66
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 66
gccgctagag gtgaaattct tg                                           22

<210> SEQ ID NO 67
<211> LENGTH: 21
<212> TYPE: DNA
<213> ORGANISM: Artificial
<220> FEATURE:
<223> OTHER INFORMATION: human ribosomal DNA reverse primer

<400> SEQUENCE: 67
cattcttggc aaatgctttc g                                            21

<210> SEQ ID NO 68
<211> LENGTH: 21
<212> TYPE: DNA
<213> ORGANISM: Artificial
<220> FEATURE:
<223> OTHER INFORMATION: human ribosomal DNA probe

<400> SEQUENCE: 68
accggcgcaa gacggaccag a                                            21

<210> SEQ ID NO 69
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 69
gtcgctcgct cctctcctac tt                                           22
```

```
<210> SEQ ID NO 70
<211> LENGTH: 19
<212> TYPE: DNA
<213> ORGANISM: Artificial
<220> FEATURE:
<223> OTHER INFORMATION: human ribosomal DNA reverse primer

<400> SEQUENCE: 70
ggctgctggc accagactt                                                19

<210> SEQ ID NO 71
<211> LENGTH: 25
<212> TYPE: DNA
<213> ORGANISM: Artificial
<220> FEATURE:
<223> OTHER INFORMATION: human ribosomal DNA probe

<400> SEQUENCE: 71
ctaatacatg ccgacgggcg ctgac                                         25

<210> SEQ ID NO 72
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 4
<223> OTHER INFORMATION: BLOCKED

<400> SEQUENCE: 72

Tyr Val Ala Asp
1

<210> SEQ ID NO 73
<211> LENGTH: 4
<212> TYPE: PRT
<213> ORGANISM: Artificial Sequence
<220> FEATURE:
<223> OTHER INFORMATION: Caspase-3 Inhibitor I
<220> FEATURE:
<221> NAME/KEY: MOD_RES
<222> LOCATION: 4
<223> OTHER INFORMATION: BLOCKED

<400> SEQUENCE: 73

Asp Glu Val Asp
1

<210> SEQ ID NO 74
<211> LENGTH: 4
<212> TYPE: PRT
<213> ORGANISM: Artificial Sequence
<220> FEATURE:
<223> OTHER INFORMATION: Caspase-3 Inhibitor II
<220> FEATURE:
<221> NAME/KEY: MOD_RES
<222> LOCATION: 1,4
<223> OTHER INFORMATION: BLOCKED

<400> SEQUENCE: 74

Asp Glu Val Asp
1

<210> SEQ ID NO 75
<211> LENGTH: 4
<212> TYPE: PRT
<213> ORGANISM: Artificial Sequence
```

```
<220> FEATURE:
<223> OTHER INFORMATION: Caspase-3 Inhibitor IV
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 4
<223> OTHER INFORMATION: BLOCKED

<400> SEQUENCE: 75

Val Glu Ile Asp
1

<210> SEQ ID NO 76
<211> LENGTH: 4
<212> TYPE: PRT
<213> ORGANISM: Artificial Sequence
<220> FEATURE:
<223> OTHER INFORMATION: Caspase-8 Inhibitor II
<220> FEATURE:
<221> NAME/KEY: MOD_RES
<222> LOCATION: 1,4
<223> OTHER INFORMATION: BLOCKED

<400> SEQUENCE: 76

Ile Glu Thr Asp
1

<210> SEQ ID NO 77
<211> LENGTH: 4
<212> TYPE: PRT
<213> ORGANISM: Artificial Sequence
<220> FEATURE:
<223> OTHER INFORMATION: Caspase-9 Inhibitor I
<220> FEATURE:
<221> NAME/KEY: MOD_RES
<222> LOCATION: 1,4
<223> OTHER INFORMATION: BLOCKED

<400> SEQUENCE: 77

Leu Glu His Asp
1

<210> SEQ ID NO 78
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 78

Tyr Val Ala Asp
1

<210> SEQ ID NO 79
<211> LENGTH: 4
<212> TYPE: PRT
```

```
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1,4
<223> OTHER INFORMATION: BLOCKED

<400> SEQUENCE: 79

Tyr Val Ala Asp
1

<210> SEQ ID NO 80
<211> LENGTH: 4
<212> TYPE: PRT
<213> ORGANISM: Artificial Sequence
<220> FEATURE:
<223> OTHER INFORMATION: Caspase-3 Inhibitor
<220> FEATURE:
<221> NAME/KEY: MOD_RES
<222> LOCATION: 1,4
<223> OTHER INFORMATION: BLOCKED

<400> SEQUENCE: 80

Asp Glu Val Asp
1

<210> SEQ ID NO 81
<211> LENGTH: 4
<212> TYPE: PRT
<213> ORGANISM: Artificial Sequence
<220> FEATURE:
<223> OTHER INFORMATION: Caspase-3 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 1
<223> OTHER INFORMATION: METHYLATION
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 81

Asp Glu Val Asp
1

<210> SEQ ID NO 82
<211> LENGTH: 4
<212> TYPE: PRT
<213> ORGANISM: Artificial Sequence
<220> FEATURE:
<223> OTHER INFORMATION: Caspase-9 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 2
<223> OTHER INFORMATION: METHYLATION
<220> FEATURE:
```

```
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 82

Leu Glu His Asp
1

<210> SEQ ID NO 83
<211> LENGTH: 4
<212> TYPE: PRT
<213> ORGANISM: Artificial Sequence
<220> FEATURE:
<223> OTHER INFORMATION: Caspase-10 inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 83

Ala Glu Val Asp
1
```

STABILISATION OF BIOLOGICAL SAMPLES

The work leading to this invention has received funding from the European Community's Seventh Framework Programme (FP7/2007-2013) under grant agreement n° 222916.

FIELD OF THE INVENTION

The technology disclosed herein inter alia relates to methods and compositions suitable for stabilizing a cell-containing sample, in particular a blood sample, and to methods for isolating nucleic acids from respectively stabilized biological samples.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 771025_414USPC_SEQUENCE_LISTING.txt. The text file is 25.2 KB, was created on Sep. 16, 2015, and is being submitted electronically via EFS-Web.

BACKGROUND OF THE INVENTION

Nucleic acids are important biomarkers in the diagnostic field. E.g. profiles of transcripts of the genome (in particular mRNA and miRNA) are widely used as biomarkers in molecular in vitro diagnostics and provide inside into normal biological and pathological processes with the hope of predicting disease outcome and indicating individualised courses of therapy. Therefore, profiling of nucleic acids, in particular RNA, is important in disease diagnosis, prognosis and in clinical trials for biomarker discovery. The ability to obtain quantitative information from the transcriptional profile is a powerful tool to explore basic biology, diagnose disease, facilitate drug development, tailor therapeutics to specific pathologies and genetic profiles and also to generate databases relevant to biological or therapeutic processes and pathways. Significant improvements of downstream assays and data analyses (analytical process) have been made during the last years. However, it was found that the preanalytical steps, such as sample handling and sample stabilisation, in particular for new biomolecular targets, have a severe impact on the expression profile and may compromise the subsequent analysis (see for example Härtel et al, 2001, Pahl and Brune, 2002). Without precaution in the stabilisation of the sample to be analysed, the sample will undergo changes during transport and storage that may severely alter the expression profile of the targeted molecules (see for example Rainen et al, 2002; Baechler et al, 2004). Thus, gene expression, in particular blood cell gene expression is sensitive to ex vivo handling of the sample. If the expression profile is altered due to the handling of the sample, the subsequent analysis does not reflect the original situation of the sample and hence of the patient but rather measure an artificial profile generated during sample handling, transport and storage. Therefore, optimized stabilisation processes are needed which stabilise the expression profile thereby allowing the reliable analysis. In particular, there is a need to stabilize blood samples in order to allow the analysis of blood cell gene expression profiles.

Stabilisation of samples such as in particular blood samples for a longer period was formally performed with the addition of organic solvents such as phenol and/or chloroform or by direct freezing in liquid nitrogen or using dry ice. These methods are not at all practicable techniques for hospitals, doctor surgeries or diagnostic routine laboratories. To overcome these problems, PreAnalytiX developed the first research product for the collection of human blood with an evacuated blood collection tube that contains reagents for an immediate stabilisation of the RNA gene expression profile at the point of sample collection (PAXgene Blood RNA Tubes). The respective stabilisation composition allows the transport and storage at room temperature without the risk of changes in the RNA profile by gene induction and transcript degradation (see for example U.S. Pat. Nos. 6,617,170, 7,270,953, Kruhoffer et al, 2007). Other stabilisation agents that achieve an immediate lysis of the sample, here blood, are sold by ABI/Life Technologies under the name Tempus Blood RNA tube product. Another product is the Biomatrica Vacuette RNAgard Blood Tube. Also with this tube lysis occurs immediately during collection and RNases are inactivated shown by intact RNA over time of blood incubation. The disadvantage of the respective methods is that the stabilisation results in the complete lysis of the cells. The destruction of the cells results in that intracellular nucleic acids become mixed with extracellular nucleic acids which prevents the separate analysis of these two nucleic acid populations. Furthermore, not only the quality and quantity of the isolated nucleic acids respectively their expression profile is of analytical interest, but also the presence, absence or number of specific cells contained in the sample such as for example a blood sample. The destruction of the cells is a great disadvantage because any cell sorting or cell enrichment respectively cell analysis becomes impossible.

Therefore, very often specific stabilisation reagents, respectively blood collection tubes are provided that are specifically intended for the stabilisation of cells. The respective products allow to investigate the cellular content of the sample after storage, for example to detect the presence of tumor cells for example by fluorescence activated cell sorting (FACS) analysis or changes of the ratio of different white blood cells to each other by flow cytometry (FC) or FACS analysis. E.g. many workflows use standard EDTA blood collection tubes for flow cytometry or FACS analysis, although blood cells show minor lysis over time of storage. A further product from Streck Inc. is a direct-draw vacuum blood collection tube for the preservation of whole blood samples for immunophenotyping by flow cytometry. It preserves white blood cell antigens allowing subsets of leucocytes to be distinguished by flow cytometry analysis. The technology to maintain the integrity of the white blood cell cluster of differentiation (CD) markers is e.g. covered by U.S. Pat. Nos. 5,460,797 and 5,459,073.

However, using different stabilisation reagents and accordingly stabilisation tubes for collecting the sample for nucleic acid analysis and cell analysis is tedious. There is a need to reduce the number of different sample collection tubes, for example blood collection tubes, per draw at the patients' site that are dedicated to different downstream assays (e.g. detection of cells and analysis of RNA). Therefore, sample collection and stabilisation systems are needed, which preserve the cell's morphology while at the same time stabilising the nucleic acids.

To address the need of simultaneous cell stabilisation and nucleic acid stabilisation, stabilisation systems were developed that are based on the use of formaldehyde releasers. Respective stabilisation agents are commercially available from Streck Inc. under the name of cell-free RNA BCT (blood collection tube). The 10 ml blood collection tube is intended for the preservation and stabilisation of cell-free RNA in plasma for up to 3 days at room temperature. The preservative stabilizes cell-free RNA in plasma and prevents the release of non-target background RNA from blood cells during sample processing and storage. US 2011/0111410 describes the use of formaldehyde releasing components to achieve cell and RNA stabilisation in the same blood sample. Therefore, this document describes a technique wherein the stabilisation agent stabilises the blood cells in the drawn blood thereby preventing contamination of cellular RNA with cell-free RNA or globin RNA, inhibits the RNA synthesis for at least 2 hours and cellular RNA that is within the blood cells is preserved to keep the protein expression pattern of the blood cells substantially unchanged to the time of the blood draw. The white blood cells can be isolated from the respectively stabilised sample and cellular RNA is than extracted from the white blood cells. However, nucleic acid isolation from respectively stabilised samples is very difficult, because the used formaldehyde releaser interferes with the subsequent nucleic acid isolation process. Therefore, the nucleic acid yield and/or purity is severely reduced compared to the isolation of nucleic acids that were stabilised using stabilization methods that specifically aim at the stabilization and isolation of nucleic acids such as RNA (for example the PAXgene Blood RNA Tubes).

Furthermore, methods are known in the prior art for stabilizing cell-containing samples, such as blood or tissue samples, which stabilize the cells, the transcriptome, genome and proteome. Such a method is e.g. disclosed in WO 2008/145710. Said method is based on the use of specific stabilizing compounds. In contrast to stabilization methods that involve a formaldehyde releaser, the isolation of nucleic acids is not impaired by the stabilization agents.

A further nucleic acid species present in cell-containing biological samples that are of clinical interest are extracellular nucleic acids. Extracellular nucleic acids have been identified in blood, plasma, serum and other body fluids. Extracellular nucleic acids that are found in respective samples are to a certain extent degradation resistant due to the fact that they are protected from nucleases (e.g. because they are secreted in form of a proteolipid complex, are associated with proteins or are contained in vesicles). The presence of elevated levels of extracellular nucleic acids such as DNA and/or RNA in many medical conditions, malignancies, and infectious processes is of interest inter alia for screening, diagnosis, prognosis, surveillance for disease progression, for identifying potential therapeutic targets, and for monitoring treatment response. Additionally, elevated fetal DNA/RNA in maternal blood is being used to determine e.g. gender identity, assess chromosomal abnormalities, and monitor pregnancy-associated complications. Thus, extracellular nucleic acids are in particular useful in non-invasive diagnosis and prognosis and can be used e.g. as diagnostic markers in many fields of application, such as non-invasive prenatal genetic testing, oncology, transplantation medicine or many other diseases and, hence, are of diagnostic relevance (e.g. fetal- or tumor-derived nucleic acids). However, extracellular nucleic acids are also found in healthy human beings. Common applications and analysis methods of extracellular nucleic acids are e.g. described in WO97/035589, WO97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8.

Traditionally, the first step of isolating extracellular nucleic acids from a cell-containing biological sample such as blood is to obtain an essentially cell-free fraction of said sample, e.g. either serum or plasma in the case of blood. The extracellular nucleic acids are then isolated from said cell-free fraction, commonly plasma when processing a blood sample.

However, obtaining an essentially cell-free fraction of a sample can be problematic and the separation is frequently a tedious and time consuming multi-step process as it is important to use carefully controlled conditions to prevent cell breakage during centrifugation which could contaminate the extracellular nucleic acids with cellular nucleic acids released during breakage. Furthermore, it is often difficult to remove all cells. Thus, many processed samples that are often and commonly classified as "cell-free" such as plasma or serum in fact still contain residual amounts of cells that were not removed during the separation process. Another important consideration is that cellular nucleic acid are released from the cells contained in the sample due to cell breakage during ex vivo incubation, typically within a relatively short period of time from a blood draw event. Once cell lysis begins, the lysed cells release additional nucleic acids which become mixed with the extracellular nucleic acids and it becomes increasingly difficult to recover the extracellular nucleic acids for testing. These problems are discussed in the prior art (see e.g. Chiu et al (2001), Clinical Chemistry 47:9 1607-1613; Fan et al (2010) and US2010/0184069). Further, the amount and recoverability of available extracellular nucleic acids can decrease substantially over time due to degradation.

Methods are known in the prior art that specifically aim at stabilizing circulating nucleic acids contained in whole blood. One method employs the use of formaldehyde to stabilize the cell membranes, thereby reducing the cell lysis and furthermore, formaldehyde inhibits nucleases. Respective methods are e.g. described in U.S. Pat. Nos. 7,332,277 and 7,442,506. However, the use of formaldehyde or formaldehyde-releasing substances has drawbacks, as they may compromise the efficacy of extracellular nucleic acid isolation by induction of crosslinks between nucleic acid molecules or between proteins and nucleic acids. Alternative methods to stabilize blood samples are described e.g. in US 2010/0184069 and US 2010/0209930. This demonstrates the great need for providing means to stabilise cell-containing biological samples, to allow the efficient recovery of e.g. extracellular nucleic acids contained in such samples.

There is still a continuous need to develop sample processing techniques which result in a stabilisation of the gene expression profile and the extracellular nucleic acid population comprised in a cell-containing biological sample, such as a whole blood sample, thereby making the handling, respectively processing of such stabilized samples easier.

It is the object of the present invention to overcome at least one of the drawbacks of the prior art sample stabilization methods. In particular, it is an object to provide a method that is capable of stabilising a cell-containing sample, in particular a whole blood sample. In particular, it is an object to provide a sample stabilization method, which allows stabilizing nucleic acids contained in the cell-containing sample. Furthermore, it is an object to provide a sample stabilization method, which is not based on cell lysis and stabilizes the extracellular nucleic acid population contained in the cell-containing sample as well as the gene expression profile of contained cells.

SUMMARY OF THE INVENTION

The present invention is based on the finding that primary and secondary carboxylic acid amides are surprisingly effective in stabilizing cell-containing biological samples, in particular whole blood samples or samples derived from whole blood such as e.g. blood plasma. It was found that these additives are highly efficient in stabilizing the extracellular nucleic acid population and in particular are capable to avoid or at least significantly reduce contaminations with genomic DNA, in particular fragmented genomic DNA. Furthermore, it was found that these additives also capable of stabilizing gene expression profiles of contained cells, thereby allowing the reliable profiling of gene expression. In contrast to prior art methods, the stabilization effect is not based on cell lysis. Therefore, the stabilization technologies described herein also allow the separate analysis of the extracellular and intracellular nucleic acid population if desired. Furthermore, the stabilization described herein allows to analyze cells contained in the stabilized sample, e.g. the cell morphology and/or cell surface characteristics.

According to a first aspect of the present invention, a method for stabilizing a cell-containing sample is provided, comprising contacting the sample with at least one carboxylic acid amide, wherein the carboxylic acid amide is selected from primary carboxylic acid amides and secondary carboxylic acid amides. Preferably, the resulting composition comprising the cell-containing biological sample and the at least one carboxylic acid amide comprises the carboxylic acid amide in a concentration of at least 0.25%.

Primary and secondary carboxylic acid amides such as formamide, butanamide, N-methylformamide and N-methylacetamide are very effective stabilizing agents for cell-containing samples, in particular blood samples. It was found that adding a respective compound has an advantageous stabilizing effect on the extracellular nucleic acid population. As is shown by the examples, these compounds are suitable for stabilizing an extracellular nucleic acid population comprised in a cell-containing sample. Furthermore, as is shown by the examples, these compounds are suitable for stabilizing and thus preserving the gene transcription profile of contained cells. As is shown by the examples, after stabilization, changes in the gene expression profile are reduced or even prevented during the stabilization period. Thus, the gene expression profile is basically "freezed" upon stabilization with a primary or secondary carboxylic acid amide and thus is preserved at the state of sample collection, respectively sample stabilization. Preferably, the cell-containing sample is selected from whole blood, plasma or serum. Furthermore, the cell stabilizing properties achieved allow analysing and also separating specific cells contained in the stabilized sample such as e.g. blood cells or circulating tumor cells contained in a blood sample.

In order to enhance the stabilization effect, it is also an object of the present invention to provide combinations of stabilizing agents e.g. in order to stabilize the extracellular nucleic acid population comprised in a cell-containing sample and/or the gene transcription profile of contained cells. A respective combination may comprise at least one primary or secondary carboxylic acid amide and additionally at least one tertiary amide and/or at least one apoptosis inhibitor. Surprisingly, it was found that an apoptosis inhibitor such as in particular a caspase inhibitor reduces contaminations of the extracellular nucleic acid population with intracellular nucleic acids, in particular fragmented genomic DNA, that originate from cells contained in the sample, e.g. from damaged or dying cells. Thus, the stabilization combination which includes an apoptosis inhibitor is very effective in substantially preserving the extracellular nucleic acid population contained in the sample in the state it had shown at the time the biological sample was obtained, respectively collected. A respective combination may also comprise additional additives that enhance the stabilizing effect such as e.g.

chelating agents. In case the sample is blood or a sample derived from blood, usually an anticoagulant is also added. Chelating agents such as e.g. EDTA are suitable for this purpose. Respective stabilizing combinations can be advantageously used in the method for stabilizing a cell-containing sample according to the first aspect.

According to a second aspect, a method for isolating nucleic acids from a biological sample is provided, wherein said method comprises the steps of:
a) stabilizing a cell-containing sample according to the method defined in the first aspect of the present invention;
b) isolating nucleic acids from the stabilized sample.

Stabilization in step a) is achieved according to the first aspect according to the present invention as described above. As discussed above, the stabilization according to the present invention inter alia has the effect that the extracellular nucleic acid population contained in the sample is substantially preserved in the state it had shown at the time the biological sample was obtained, respectively collected. Therefore, extracellular nucleic acids obtained from a respectively stabilized sample comprise less contaminations with intracellular nucleic acids, in particular fragmented genomic DNA, that results e.g. from decaying cells comprised in the sample compared to extracellular nucleic acids that are obtained from an unstabilized sample. The substantial preservation of the extracellular nucleic acid population is an important advantage because this stabilization/preservation enhances the accuracy of any subsequent tests. It allows for standardizing the isolation and subsequent analysis of the extracellular nucleic acid population, thereby making diagnostic or prognostic applications that are based on the extracellular nucleic acid fraction more reliable and more independent from the used storage/handling conditions. In particular, the teachings of the present invention have the advantage that the ratio of certain extracellular nucleic acid molecules can be kept substantially constant compared to the ratio at the time the sample was collected. The stabilization achieves that intracellular nucleic acids are substantially kept within the cells and that extracellular nucleic acids are substantially stabilized. Furthermore, the stabilization methods described herein are also suitable for stabilizing intracellular nucleic acids. After sample stabilization, intracellular RNA is protected from degradation and furthermore, changes in the gene transcription profile of contained cells are inhibited. Thus, the stabilization described herein in particular reduces in vitro degradation and minimizes gene induction. Therefore, intracellular nucleic acids isolated from respectively stabilized samples are well suitable e.g. for gene expression profiling and other analytical methods that require an accurate representation of in vivo transcript levels in the stabilized sample. Furthermore, advantageously, the stabilization method described herein allows if desired to isolate stabilized extracellular nucleic acids separately from stabilized intracellular nucleic acids from the same stabilized sample. According to a third aspect, a composition suitable for stabilizing a cell-containing biological sample is provided, comprising:
a) at least one carboxylic acid amide in a concentration of at least 1%, wherein the carboxylic acid amide is selected from primary carboxylic acid amides and secondary carboxylic acid amides; and
b) at least one anticoagulant.

A respective stabilizing composition is particularly effective in stabilizing a cell-containing biological sample, in particular whole blood, plasma and/or serum by stabilizing the extracellular nucleic acid population comprised in said sample. Furthermore, a respective stabilizing composition is effective in stabilizing the gene transcription profile of contained cells. Furthermore, cells and important cell characteristics such as e.g. the cell morphology and/or cell surface characteristics of contained cells can be preserved as is shown by the examples. A respective stabilizing composition allows the storage and/or handling, e.g.

shipping, of the sample, e.g. whole blood, at room temperature for at least two, or preferably at least three days without substantially compromising the quality of the sample, respectively the extracellular nucleic acid population contained therein. Thus, when using the stabilization composition according to the present invention, the time between sample collection, e.g. blood collection, and nucleic acid extraction can vary without substantial effect on the extracellular nucleic acid population contained in the sample or the gene expression profile of contained cells. This is an important advantage as it reduces the variability in the extracellular nucleic acid population and the intracellular nucleic acid population, in particular transcript levels, attributable to different handling procedures. According to one embodiment, the composition additionally comprises at least one apoptosis inhibitor, preferably a caspase inhibitor.

According to a fourth aspect, a container for collecting a cell-containing biological sample, preferably a blood sample, is provided which comprises
a) at least one carboxylic acid amide, preferably in a concentration of at least 1%, wherein the carboxylic acid amide is selected from primary carboxylic acid amides and secondary carboxylic acid amides; and
b) at least one anticoagulant.

The container for collecting a cell-containing biological sample, preferably a blood sample, may comprise a composition according to the third aspect of the present invention. Providing a respective container, e.g. a sample collection tube comprising the stabilizing composition has the advantage that the sample is immediately stabilized as soon as the sample is collected in the respective container. Furthermore, a respective sample collection container, in particular a blood collection tube, is capable of stabilising blood cells and their gene transcription profile and is capable of stabilizing extracellular nucleic acids and optionally, viruses respectively viral nucleic acids contained in a blood sample or a sample derived from blood. Thereby, a further problem was overcome.

According to a fifth aspect, a method is provided comprising the step of collecting, preferably withdrawing, a biological sample, preferably blood, from a patient directly into a chamber of a container according to the fourth aspect of the present invention. According to a sixth aspect, a method of producing a composition according to the third aspect of the present invention is provided, wherein the components of the composition are mixed, preferably are mixed in a solution. The term "solution" as used herein in particular refers to a liquid composition, preferably an aqueous composition. It may be a homogenous mixture of only one phase but it is also within the scope of the present invention that a solution comprises solid components such as e.g. precipitates.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only.

DETAILED DESCRIPTION OF THIS INVENTION

Figure 1:
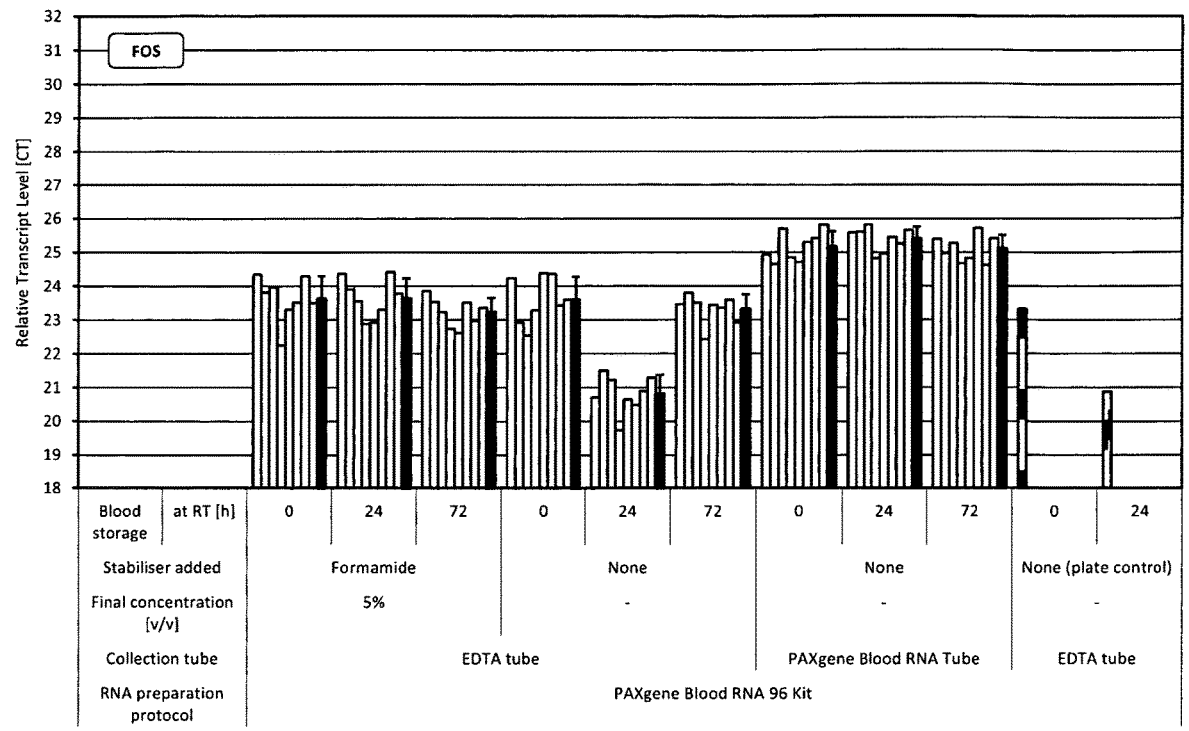
FIGS. 1 to 4: Relative transcript levels of FOS, IL1B, IL8 and TP53 (from FIGS. 1 to 4) from samples of example 1. Transcripts were analysed using real time monoplex RT-PCR assays. Transcript levels given as cycle thresholds (CT) of individual samples are shown as white bars, means as black solid bars with standard deviations and control samples of an additional donor of a different experiment serving as positive control of gene expression changes and RT-PCR within each PCR run (plate control) as shaded bars.
Figure 2:
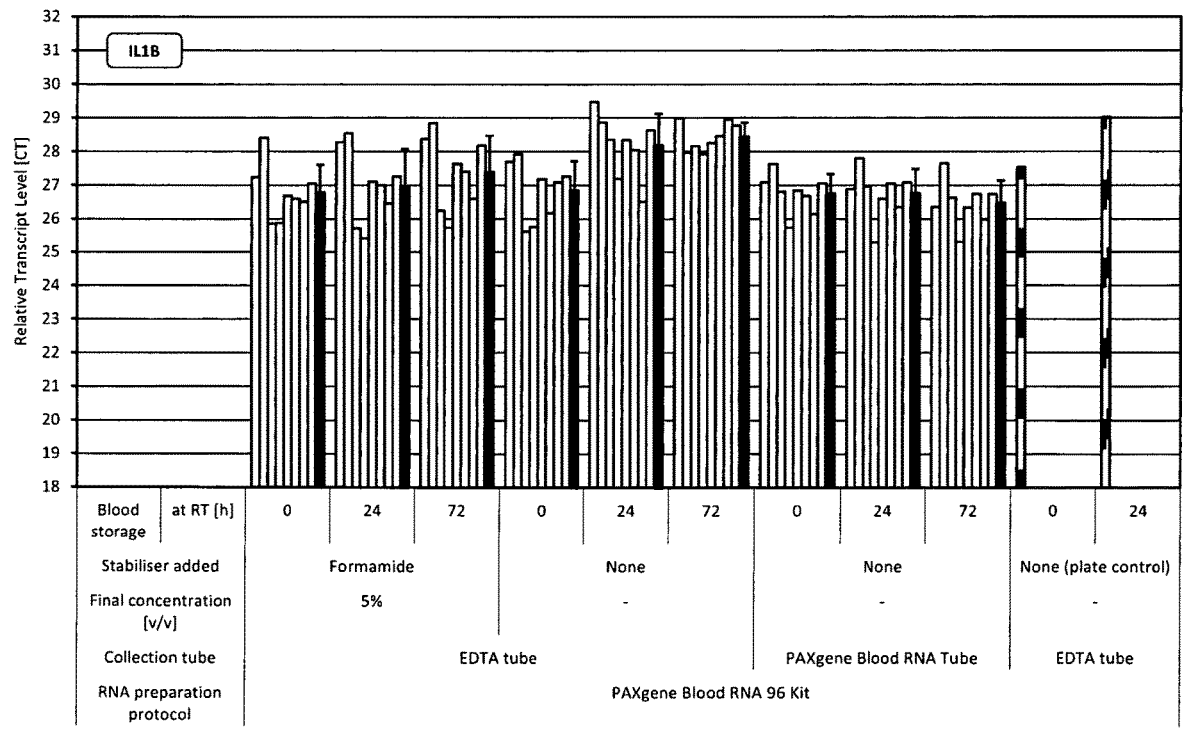
Figure 3:
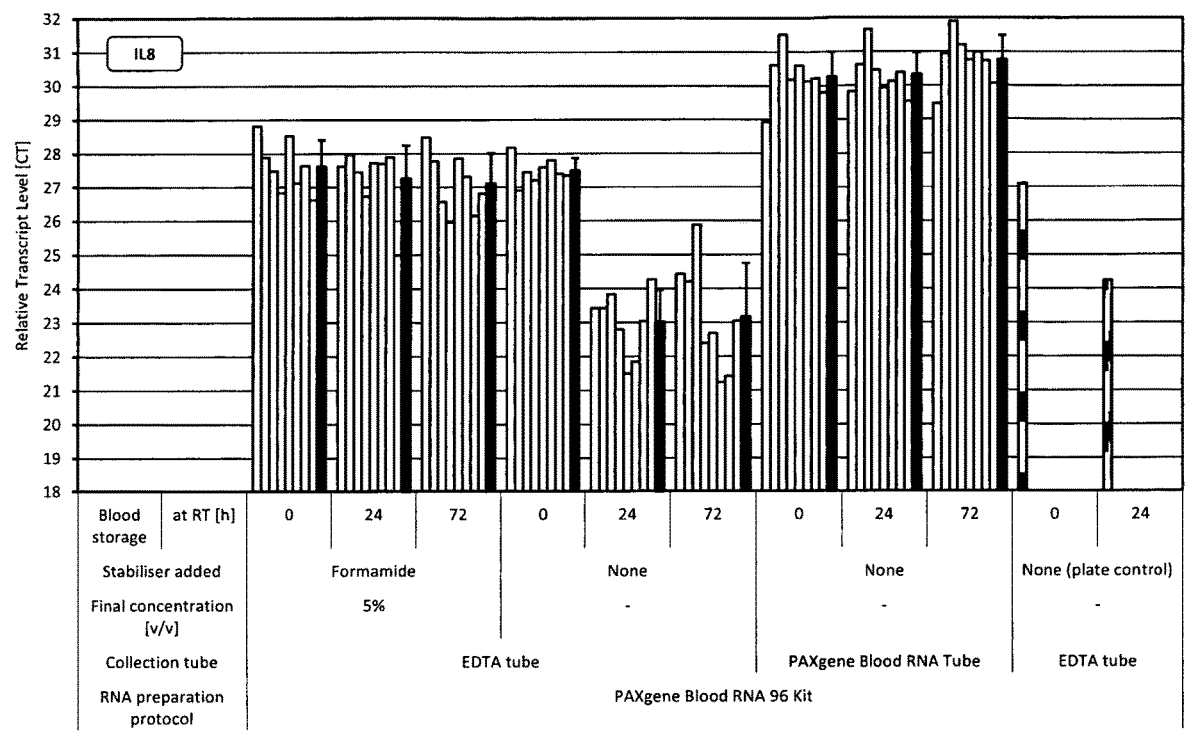
Figure 4:
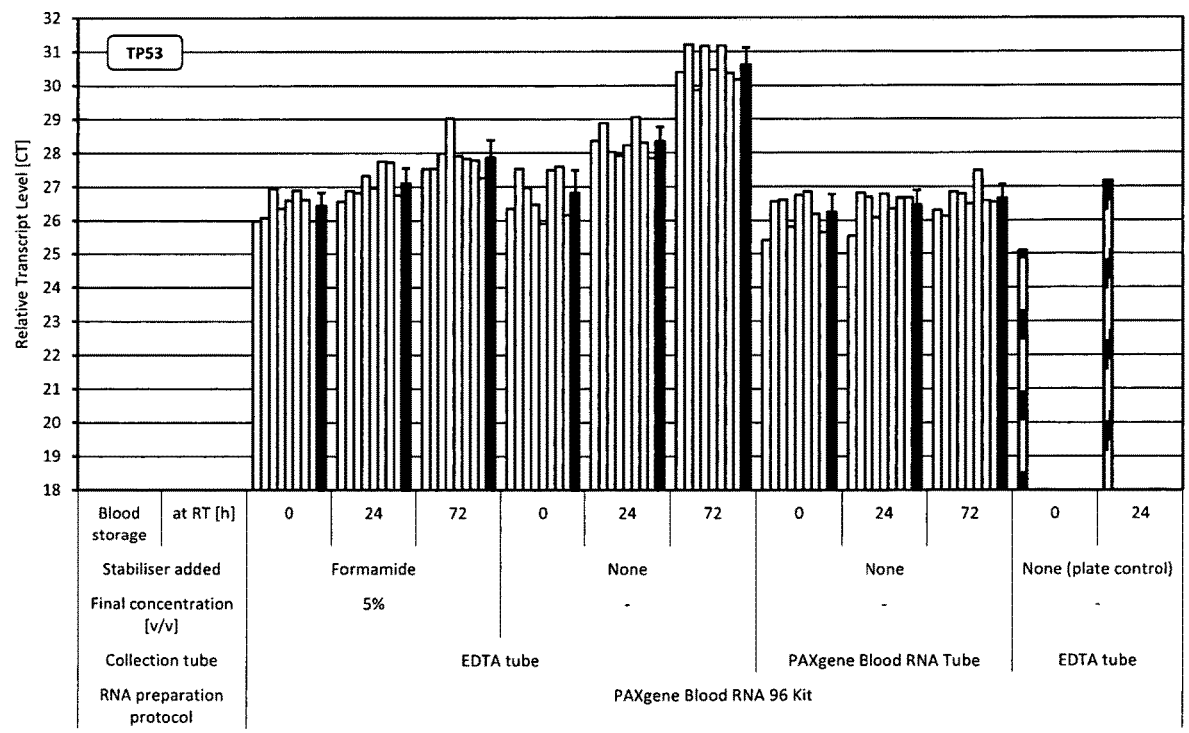

The present invention is directed to methods, compositions and devices and thus to technologies suitable for stabilizing the extracellular nucleic acid population comprised in a cell-containing biological sample and/or for stabilizing the gene transcription profile and thus the transcriptome of contained cells. The stabilization technologies disclosed herein e.g. reduce the risk that the extracellular nucleic acid population is contaminated with intracellular nucleic acids, in particular fragmented genomic DNA, which derives from, e.g. is released, from damaged and/or dying cells contained in the sample. Furthermore, the stabilizing technologies disclosed herein substantially preserve the gene transcription profile of contained cells, thereby allowing the reliable analysis of gene expression profiles. Furthermore, the stabilization described herein prevents contaminations of extracellular nucleic acids with intracellular nucleic acids and vice versa which allows a separate analysis of the extracellular nucleic acid population and the intracellular nucleic acids from the same stabilized cell-containing sample if desired. Therefore, the present invention achieves the stabilization of the sample and hence the stabilization of the extracellular nucleic acid population and/or the intracellular nucleic acid population without the lysis of the contained cells. Rather, cells contained in the sample are stabilized thereby substantially preventing or reducing the release of intracellular nucleic acids. Furthermore, as is shown by the examples, the gene transcription profile of contained cells is substantially preserved, by inhibiting changes and thus alterations in the transcript levels. Furthermore, cells can be recovered from the stabilized samples and are suitable for different analyses. E.g. the cell morphology and/or the cell surface characteristics of contained can be analysed if desired. Furthermore, the stabilized sample can be analyzed for the presence or absence of specific cells such as e.g. tumor cells, e.g. circulating tumor cells present in whole blood samples.

The remarkable stabilization of nucleic acids that is achieved with the methods and compositions of the present invention allows the storage and/or handling of the stabilized sample for a prolonged period of time at room temperature without jeopardizing the quality of the sample, respectively the extracellular nucleic acids contained therein. As the composition of the extracellular nucleic acid population and the intracellular transcriptome is stabilized and thus substantially preserved at the time the sample is obtained by using the teachings of the present invention, the time between sample collection and nucleic acid extraction can vary without significant effect on the composition of the extracellular nucleic acids population. This allows the standardization of e.g. diagnostic or prognostic extracellular nucleic acid analysis because variations in the handling/storage of the samples have less influence on the quality, respectively the composition of the extracellular nucleic acid population, thereby providing an important advantage over prior art methods. Hence, the samples, respectively the extracellular nucleic acids obtained from respectively stabilized samples become more comparable. Furthermore, the achieved stabilization of the gene transcription profile of contained cells allows a reliable gene expression analysis even after prolonged storage of the stabilized samples. Furthermore, advantageously, the teachings of the present invention obviate the necessity to directly separate cells contained in the sample from the cell-free portion of the sample in order to avoid, respectively reduce contaminations of the extracellular nucleic acids with intracellular nucleic acids, in particular fragmented genomic DNA, that is otherwise released from decaying cells. This advantage considerably simplifies the handling of the samples, in particular the handling of whole blood samples. E.g. whole blood samples obtained in a clinic and stabilized according to the teachings of the present invention can be shipped at room temperature and the plasma containing the extracellular nucleic acids can be conveniently separated from the contained cells in the receiving clinical lab. However, the teachings of the invention are also advantageous when processing cell-depleted biological samples, or samples commonly referred to as "cell-free" such as e.g. blood plasma or serum. Respective cell-depleted or "cell-free" biological samples may still (also depending on the used separation process) comprise residual cells, in particular white blood cells which comprise genomic DNA, which accordingly, pose a risk that the extracellular nucleic acid population becomes increasingly contaminated with intracellular nucleic acids, in particular fragmented genomic DNA, if the (potentially) remaining cells are damaged or die during the shipping of storing process. This risk is considerably reduced when using the stabilization method taught by the present invention. Because the technology of the present invention allows to efficiently preserve the extracellular nucleic acid population of the sample and the gene expression profile of contained cells at the time the sample is collected and contacted with the stabilizing agents, said samples can be properly worked up in the receiving facilities in order to isolate the extracellular nucleic acids from said samples while substantially avoiding respectively reducing contaminations of the extracellular nucleic population with intracellular nucleic acids. Intracellular nucleic acids can be isolated from the stabilized cells and can be used e.g. for gene expression profiling. The facilities receiving the samples such as e.g. laboratories usually also have the necessary equipment such as e.g. high speed centrifuges (or other means, see also below) to efficiently remove cells comprised in the samples, including residual cells that might be present in cell-depleted samples such as e.g. in blood plasma. Such equipment is often not present in the facilities where the sample is obtained. Thus, the present invention has many advantages when stabilizing biological samples which comprise a large amount of cells such as e.g. whole blood samples, but also has important advantages when stabilizing biological samples which comprise only a small amount of cells or which may only be suspected of containing cells such as e.g. plasma, serum, urine, saliva, synovial fluids, amniotic fluid, lachrymal fluid, ichors, lymphatic fluid, liquor, cerebrospinal fluid and the like.

Method for Stabilizing a Cell-Containing Sample

According to a first aspect, a method for stabilizing a cell-containing sample, preferably a blood sample, is provided, by contacting the sample with at least one carboxylic acid amide, wherein the carboxylic acid amide is selected from primary carboxylic acid amides and secondary carboxylic acid amides. Preferably, the resulting composition comprising the cell-containing biological sample and the at least one carboxylic acid amide comprises the carboxylic acid amide in a concentration of at least 0.25%.

As is shown by the provided examples such compounds are inter alia effective in achieving a remarkable stabilizing effect on the cell-containing sample e.g. in substantially preserving the composition of the extracellular nucleic acid population in the stabilized sample. Thereby, the risk is reduced that the extracellular nucleic acid population is contaminated with intracellular nucleic acids, in particular fragmented genomic DNA originating from contained cells, e.g. from damaged or dying cells and/or the degradation of nucleic acids present in the sample is reduced, respectively inhibited. This has the effect that the composition of the extracellular nucleic acid population comprised in said sample is substantially preserved, respectively stabilized. Also a mixture of one or more of primary and/or secondary carboxylic acid amides can be used for stabilization. Furthermore, nucleic acids can be efficiently isolated from respectively stabilized samples using standard nucleic acid isolation methods because the carboxylic acid amides used herein for stabilization do not have cross-linking properties. This is an important advantage as it e.g. simplifies the further processing of the stabilized samples and also increases the chance that e.g. rare target nucleic acids comprised in the extracellular nucleic acid population can be subsequently detected.

According to one embodiment, the carboxylic acid amide which is selected from primary carboxylic acid amides and secondary carboxylic acid amides has the formula 1

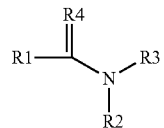

formula 1 wherein R1 is a hydrogen residue or an alkyl residue, wherein R2 is selected from a hydrogen residue and a hydrocarbon residue with a length of the carbon chain of 1-20 atoms arranged in a linear or branched manner, wherein R3 is a hydrogen residue, and wherein R4 is oxygen. Suitable and preferred examples of R1, R2 and R3 are also described below.

In one embodiment, R1 is a C1-C5 alkyl residue, preferably a C1-C4 alkyl residue or a C1-C3 alkyl residue, more preferred a C1-C2 alkyl residue. In another embodiment, R1 is a hydrogen residue. The chain length n of R1 preferably has the value 1, 2, 3, 4 or 5. Particularly preferred is a chain length of 1 or 2 for R1. In particularly preferred embodiments, R1 is selected from the group consisting of a hydrogen residue, a methyl residue, an ethyl residue and a propyl residue.

R2 and R3 of the compound according to formula 1 are identical or different and are selected from a hydrogen residue and a hydrocarbon residue. According to one embodiment, the compound according to formula 1 is a primary amide and R2 and R3 are both hydrogen residues. According to another embodiment, the compound according to formula 1 is a secondary amide and R2 is a hydrocarbon residue and R3 is a hydrogen residue. According to another embodiment described below, the compound according to formula 1 is a tertiary amide and R2 and R3 are identical or different hydrocarbon residues (see below). The hydrocarbon residues R2 and/or R3 can be selected independently of one another from the group comprising of alkyl, including short chain alkyl and long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. General groups, for instance alkyl, alkoxy, aryl etc. are claimed and described in the description and the claims. Preferably, the following groups are used within the generally described groups within the scope of the present invention:

(1) alkyl: preferably short chain alkyls, in particular linear and branched C1-C5 alkyls or long-chain alkyls: linear and branched C5-C20 alkyls;
(2) alkenyl: preferably C2-C6 alkenyl;
(3) cycloalkyl: preferably C3-C8 cycloalkyl;
(4) alkoxy: preferably C1-C6 alkoxy;
(5) long-chain alkoxy: preferably linear and branched C5-C20 alkoxy;
(6) alkylenes: preferably a divalent linear or branched aliphatic, cycloaliphatic or aromatic hydrocarbon residue with 2 to 18 carbon atoms optionally containing heteroatoms, e.g. selected from the group comprising: methylene; 1,1-ethylene; 1,1-propylidene; 1,2-propylene; 1,3-propylene; 2,2-propylidene; butan-2-ol-1,4-diyl; propan-2-ol-1,3-diyl; 1,4-butylene; 1,4-pentylene; 1,6-hexylene; 1,7-heptylene; 1,8-octylene; 1,9-nonylene; 1,10-decylene; 1,11-undecylene; 1,12-docedylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl;

(7) alkenediyl: preferably selected from the group comprising: 1,2-propenediyl; 1,2-butenediyl; 2,3-butenediyl; 1,2-pentenediyl; 2,3-pentenediyl; 1,2-hexenediyl; 2,3-hexenediyl; and 3,4-hexenediyl;
(8) alkynediyl: is equal to —C≡C—;
(9) aryl: preferably selected from aromatics with a molecular weight below 300 Da;
(10) arylenes: preferably selected from the group comprising: 1,2-phenylene; 1,3-phenylene; 1,4-phenylene; 1,2-naphtthalenylene; 1,3-naphtthalenylene; 1,4-naphtthalenylene; 2,3-naphtthalenylene; 1-hydroxy-2,3-phenylene; 1-hydroxy-2,4-phenylene; 1-hydroxy-2,5-phenylene; 1-hydroxy-2,6-phenylene;
(11) carboxylate: preferably the group —C(O)OR, where R is selected from: hydrogen; C1-C6 alkyl; phenyl; C1-C6 alkyl-C6H5; Li; Na; K; Cs; Mg; Ca;
(12) carbonyl: preferably the group —C(O)R, where R is selected from: hydrogen; C1-C6 alkyl; phenyl; C1-C6 alkyl-C6H5 and amine (resulting in an amide) selected from the group: —NR'2, where each R' is selected independently from: hydrogen; C1-C6 alkyl; C1-C6 alkyl-C6H5 and phenyl, where, if both Rs represent C1-C6 alkyl they can form an NC3 to NC5 heterocyclic ring with alkyl substituents of the ring forming the other alkyl chain;
(13) alkylsilyl: preferably the group —SiR1R2R3, where R1, R2 and R3 are selected independently of one another from: hydrogen; alkyl; long-chain alkyl; phenyl; cycloalkyl; haloalkyl; alkoxy; long-chain alkoxy;
(14) alkylsilyloxy: preferably the group —O—SiR1R2R3, where R1, R2 and R3 are selected independently of one another from: hydrogen; alkyl; long-chain alkyl; phenyl; cycloalkyl; haloalkyl; alkoxy; long-chain alkoxy.

In certain embodiments, R1, R2 and/or R3 are a hydrogen residue or an unsubstituted, saturated, linear or branched hydrocarbon residue.

The chain length n of R2 and/or R3 can in particular have the values 1, 2, 3, 4, 5, 6, 7, 8, 9, 10, 11, 12, 13, 14, 15, 16, 17, 18, 19 and 20. Preferably R2 and R3 have a length of the carbon chain of 1-10. In this case the chain length n can in particular have the values 1, 2, 3, 4, 5, 6, 7, 8, 9, and 10. Preferably, R2 and R3 have a length of the carbon chain of 1-5 and in this case the chain length can in particular have the values 1, 2, 3, 4 and 5. Particularly preferred is a chain length of 1 or 2 for R2 and R3. Preferably, R2 and R3 are both alkyl residues in the tertiary amides described below, preferably C1-C5 alkyl residues. In particularly preferred embodiments, R2 and/or R3 are selected from the group consisting of a hydrogen residue and an alkyl residue, preferably a methyl residue.

R4 preferably is oxygen.

In preferred embodiments, the carboxylic acid amide according to the invention which is selected from primary carboxylic acid amides and secondary carboxylic acid amides is a compound according to formula 1, wherein R3 is a hydrogen residue and wherein R4 is an oxygen residue. Preferably, R2 is selected from the group consisting of a hydrogen residue and a C1-C5 alkyl residue, preferably a methyl residue. Furthermore, R1 preferably is selected from the group consisting of a hydrogen residue, a methyl residue, an ethyl residue and a propyl residue. Preferably, the primary carboxylic acid amide is selected from the group consisting of formamide, acetamide, propanamide and butanamide. Preferably, the carboxylic acid amide is selected from butanamide and formamide. More preferred, it is butanamide, in particular for stabilizing the extracellular nucleic acid population. As is shown by the examples, butanamide is a particularly effective stabilizer and furthermore, non-toxic according to GHS classification. According to one embodiment, the primary carboxylic acid amide is not propanamide.

According to one embodiment, the cell-containing biological sample is contacted with at least one secondary carboxylic acid amide which is selected from the group consisting of N-alkylformamide, N-alkylacetamide and N-alkylpropanamide, and preferably is selected from N-methylformamide, N-methylacetamide and N-methylpropanamide. As is shown in the examples, these compounds are all effective stabilizing agents.

The mixture that is obtained when contacting the cell-containing biological sample with the at least one primary or secondary carboxylic acid amide or a mixture of respective compounds (and optionally further additives such as preferably a caspase inhibitor) may comprise said compound (or mixture of such compounds) in a concentration of at least 0.1%, at least 0.25%, at least 0.5%, at least 0.75%, at least 1%, at least 1.25%, at least 1.5% or at least 2%. Suitable concentration ranges include but are not limited to 0.1% to 30%, 0.25% to 20%, 0.5% to 15%, 0.7% to 10%, 0.8% to 7.5%, 0.9% to 6% and 1% to 5%. Concentrations or concentration ranges indicated in percentage values as used herein are in particular given as percentage weight per volume (w/v) for solid compounds, substances or compositions in a liquid composition, and as percentage volume per volume (v/v) for liquid compounds, substances or compositions in a liquid composition. As can be seen from the examples, the primary and secondary carboxylic acid amides are effective stabilizers over a broad concentration range. Suitable concentrations for different compounds and/or for different sample types can also be determined by the skilled person using routine experiments, e.g. by testing different concentrations in the test assays described in the examples.

According to one embodiment, butanamide is used as carboxylic acid amide and the mixture that is obtained after contacting the cell-containing biological sample with butanamide and optionally further additives may comprise butanamide in a concentration of at least 0.1% (w/v), at least 0.2% (w/v), at least 0.3% (w/v), at least 0.4% (w/v), at least 0.5% (w/v), at least 0.6% (w/v), at least 0.75% (w/v), at least 1% (w/v), at least 1.25% (w/v), at least 1.5% (w/v), at least 1.75% (w/v), at least 1.85% (w/v), at least 2% (w/v), at least 2.1% (w/v), at least 2.2% (w/v), at least 2.3% (w/v), at least 2.4% (w/v), at least 2.5% (w/v), at least 2.6% (w/v), at least 2.7% (w/v), at least 2.8% (w/v), at least 2.9% (w/v) or at least 3% (w/v). Butanamide is used in a concentration, wherein it exerts a stabilizing effect on the cell-containing biological sample, in particular the extracellular nucleic acid population that is contained in the cell-free portion of the cell-containing sample. As is shown by the examples, butanamide is effective in various concentrations. Suitable concentrations of butanamide for different sample types can also be determined by the skilled person using routine experiments, e.g. by testing different concentrations of butanamide in the test assays described in the examples. As is shown by the examples, the suitable concentration range for butanamide also depends on whether one or more additional stabilizers are used in combination with butanamide. E.g. lower concentrations of butanamide can be used if one or more additional stabilizing additives as described herein, preferably at least one caspase inhibitor and/or a tertiary amide according to formula 1 (see below), are used in combination with butanamide for stabilizing a cell-containing biological sample such as e.g. blood. Suitable concentration ranges for butanamide when mixed with the cell-containing biological sample and optionally further additives, include but are not limited to 0.1% (w/v) up to 15%, 0.25% (w/v) to 13% (w/v), 0.4% (w/v) to 12% (w/v), 0.5% (w/v) to 10% (w/v), 0.75% (w/v) to 8% (w/v), 1% (w/v) to 7.5% (w/v), 1.25% (w/v) to 7% (w/v), 1.5% (w/v) to 6.5% (w/v), 1.75% (w/v) to 6° A) (w/v), 1.8% (w/v) to 5.5% (w/v), 1.9% (w/v) to 5.25% (w/v), 2% (w/v) to 5% (w/v), 2.1% (w/v) to 4.75% (w/v), 2.2% (w/v) to 4.5% (w/v), 2.3% (w/v) to 4.25% (w/v), 2.4% (w/v) to 4% (w/v), 2.5% (w/v) to 3.75% (w/v) or 2.5% (w/v) to 3.5% (w/v). According to one embodiment, said mixture that is obtained after contacting the cell-containing biological sample with butanamide and optionally further additives, comprises butanamide in a concentration that lies in the range of 0.5% (w/v) to 3.5% (w/v), preferably 0.75% (w/v) to 3.25% or 0.9% (w/v) to 3% (w/v). Such concentrations are particularly suitable for stabilizing blood samples. As is shown by the examples, using butanamide in a concentration that lies in these ranges provides an excellent stabilizing effect on blood samples and furthermore, prevents the hemolysis of the red blood cells contained in the blood sample. A lower butanamide concentration of 5 2% (w/v) is particularly effective when additionally using a further stabilizing agent such as preferably a caspase inhibitor and/or a tertiary amide according to formula 1. As is shown by the examples, using a combination of these stabilizing agents is particularly advantageous for stabilizing blood samples.

According to one embodiment, formamide is used as carboxylic acid amide. Formamide is particularly effective in stabilizing the transcriptome as well as the extracellular nucleic acid population. The mixture that is obtained after contacting the cell-containing biological sample with formamide and optionally further additives may comprise formamide in a concentration of at least 0.1% (v/v), at least 0.25% (v/v), at least 0.5% (v/v), at least 0.75% (v/v), at least 1% (v/v), at least 1.25% (v/v), at least 1.5% (v/v) or at least 2% (v/v). Formamide is used in a concentration, wherein it exerts a stabilizing effect on the cell-containing biological sample, in particular the extracellular nucleic acid population that is contained in the cell-free portion of the cell-containing sample and/or the transcriptome. As is shown by the examples, formamide is effective in various concentrations. Suitable concentrations of formamide for different sample types can also be determined by the skilled person using routine experiments, e.g. by testing different concentrations of formamide in the test assays described in the examples. As is shown by the examples, the suitable concentration range for formamide also depends on whether one or more additional stabilizers are used in combination with formamide. E.g. lower concentrations of formamide can be used if one or more additional stabilizing additives as described herein, preferably at least one caspase inhibitor, are used in combination with formamide for stabilizing a cell-containing biological sample such as e.g. blood. Suitable concentration ranges for formamide when mixed with the cell-containing biological sample and optionally further additives, include but are not limited to 0.25% (v/v) to 20% (v/v), 0.5% (v/v) to 15% (v/v), 0.7% (v/v) to 10% (v/v), 0.8% (v/v) to 7.5% (v/v), 0.9% (v/v) to 6% (v/v) and 1% (v/v) to 5% (v/v). According to one embodiment, said mixture that is obtained after contacting the cell-containing biological sample with formamide and optionally further additives, comprises formamide in a concentration that lies in the range of 0.5% (v/v) to 15% (w/v), preferably 0.7% (v/v) to 10% (v/v). Such concentrations are particularly suitable for stabilizing blood samples. As is shown by the examples, using formamide in a concentration that lies in these ranges provides an excellent stabilizing effect on blood samples. For stabilizing the transcriptome, the concentration of formamide in the resulting mixture with the cell-containing sample is preferably at least 2% (v/v), preferably at least 3% (v/v). As is shown by the examples, a concentration of approx. 5% (v/v) is particularly effective. Thus, preferably, the concentration lies in a range of 2% (v/v) to 7.5% (v/v) for this purpose.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA. Examples of typical extracellular nucleic acids that are found in the cell-free fraction (respectively portion) of biological samples such as body fluids such as e.g. blood plasma include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. The extracellular nucleic acid population usually comprises certain amounts of intracellular nucleic acids that were released from damaged or dying cells. E.g. the extracellular nucleic acid population present in blood usually comprises intracellular globin mRNA that was released from damaged or dying cells. This is a natural process that occurs in vivo. Such intracellular nucleic acid present in the extracellular nucleic acid population can even serve the purpose of a control in a subsequent nucleic acid detection method. The stabilization method described herein in particular reduces the risk that the amount of intracellular nucleic acids, such as genomic DNA, that is comprised in the extracellular nucleic acid population is significantly increased after the cell-containing sample was collected due to the ex vivo handling of the sample. Thus, alterations of the extracellular nucleic acid population because of the ex vivo handling are reduced and can even be prevented. According to one embodiment, the extracellular nucleic acid is obtained from respectively is comprised in a body fluid as cell-containing biological sample such as e.g. blood, plasma, serum, saliva, urine, liquor, cerebrospinal fluid, sputum, lachrymal fluid, sweat, amniotic or lymphatic fluid. Herein, we refer to extracellular nucleic acids that are obtained from circulating body fluids as circulating extracellular or circulating cell-free nucleic acids. According to one embodiment, the term extracellular nucleic acid in particular refers to mammalian extracellular nucleic acids. Examples include, but are not limited to disease-associated or disease-derived extracellular nucleic acids such as tumor-associated or tumor-derived extracellular nucleic acids, extracellular nucleic acids released due to inflammations or injuries, in particular traumata, extracellular nucleic acids related to and/or released due to other diseases, or extracellular nucleic acids derived from a foetus. The term "extracellular nucleic acids" or "extracellular nucleic acid" as described herein also refers to extracellular nucleic acids obtained from other samples, in particular biological samples other than body fluids. Usually, more than one extracellular nucleic acid is comprised in a sample. Usually, a sample comprises more than one kind or type of extracellular nucleic acids. The term "extracellular nucleic acid population" as used herein in particular refers to the collective of different extracellular nucleic acids that are comprised in a cell-containing sample. A cell-containing sample usually comprises a characteristic and thus unique extracellular nucleic acid population. Thus, the type, kind and/or the amount of one or more extracellular nucleic acids comprised in the extracellular nucleic acid population of a specific sample are important sample characteristics. As discussed above, it is therefore important to stabilize and thus to substantially preserve said extracellular nucleic acid population as its composition and/or the amount of one or more extracellular nucleic acids comprised in the extracellular nucleic acid population of a sample, can provide valuable information in the medical, prognostic or diagnostic field. Therefore, it is advantageous if the profile of the extracellular nucleic acid population is efficiently stabilized. The stabilization technologies described herein reduce contaminations and hence a dilution of the extracellular nucleic acid population by intracellular nucleic acids, in particular by genomic DNA, after sample collection and stabilization. Thus, a substantial preservation of the extracellular nucleic acid population is achieved. As is shown by the examples, changes in the extracellular nucleic acid population with respect to the quantity, the quality and/or the composition of the comprised extracellular nucleic acids, in particular changes attributable to an increase of released genomic DNA, are over the stabilization period considerably reduced compared to an unstabilized sample or a corresponding sample that is e.g. stabilized by EDTA in case of a blood sample or a sample derived from blood. According to one embodiment the increase in genomic DNA from $T_0$ (stabilization point) to the end of the stabilization period (preferably 48 h, 72 h or 96 h after $T_0$) is reduced by at least 60%, at least 70%, at least 75%, at least 80%, at least 85%, at least 90% or at least 95% compared to an unstabilized sample or a corresponding sample that is e.g. stabilized by EDTA in case of a blood sample (e.g. 1.5 mg EDTA/ml stabilized blood sample) or a sample derived from blood.

Furthermore, as described above, the method of the invention is also suitable for stabilizing intracellular nucleic acids, in particular intracellular RNA. Contacting the cell-containing sample with primary and/or secondary carboxylic acid amides as described herein results in that gene transcript levels of contained cells are stabilized. Thus, the generation of new transcripts and the degradation of existing transcripts in the stabilized sample are inhibited compared to an unstabilized sample, thereby substantially "freezing" the gene transcription profile of contained cells upon stabilization. Therefore, the stabilization is also suitable for stabilizing the transcriptome by maintaining transcript levels at the state they had shown at sample collection and stabilization. The term transcriptome in particular refers to the set of all RNA molecules, including mRNA, rRNA, tRNA and other non-coding RNA such as miRNA, produced in one or a population of cells. As is demonstrated by the examples, cell-containing biological samples such as blood samples could be stabilized for at least three days and even longer without substantial changes of transcript levels. The gene transcription profile is in particular stabilized by reducing RNA degradation and minimizing alterations of the gene expression such as in particular gene induction or down-regulation. Without being bound in theory, it is believed that primary and/or secondary carboxylic acid amides used herein for stabilization inhibit cellular processes whereby the new synthesis of transcripts as well as the degradation of existing transcripts is inhibited. It is believed that they enter the cell and are thus cell-permeable to achieve these effects. Thus, after collection and stabilization of the cell-containing sample, the in vivo gene expression profile existing at collection, respectively stabilization is preserved. Furthermore, the quality and integrity of the RNA is maintained, thereby providing an accurate representation of the in vivo transcript levels at the time of sample collection, respectively sample stabilization, and allowing to obtain a true and accurate transcript level. The preservation of the in vivo gene transcription profile upon stabilization allows performing e.g. gene expression profiling or other analytical methods that require an accurate representation of the transcript levels using respectively stabilized samples. However, even though desired, it is often not necessary that all transcript levels are stabilized or are stabilized equally well. The stabilization and thus performance characteristics for a specific or new target transcript should be validated as is also usual with the prior art technologies which stabilize gene transcription profiles. That stabilization of the gene transcription profile or of specific transcript levels was achieved can be determined e.g.

based on marker genes that are established for analyzing the stabilization of the gene transcription profile. According to one embodiment, the stabilization of the gene transcription profile or the transcript level of contained cells achieved by the method results in that one or more, preferably two or more marker genes selected from c-fos, IL-1 beta, IL-8 and p53 is/are stabilized for at least 48 h upon stabilization. These marker genes were identified as providing very unstable transcripts during storage and thus are in the absence of appropriate stabilization up- or downregulated after sample collection. Therefore, the transcript levels of these genes are suitable as marker to analyse whether a stabilization of the gene transcription level was achieved. The stabilization effect can be analysed using the real time RT-PCR assays described in the examples. According to one embodiment, the transcript levels of one or more of these marker genes is not altered by more than 1.5 CT values, preferably not more than 1.25CT values, more preferred not more than 1CT value between $T_0$ (stabilization point) and the end of the stabilization period. Preferably, a respective stabilization effect is achieved for at least 48 h, at least 72 h or at least 96 h. Preferably, respective stabilization characteristics are achieved at least with the marker genes c-fos, IL8 and IL-1 beta and preferably with all of the aforementioned marker genes. As is shown by the examples, various primary and/or secondary carboxylic acid amides, in particular formamide, achieve a respective stabilization performance.

Furthermore, as the method according to the present invention is not based on cell lysis, cells can be separated from the stabilized sample after the stabilization period and cells isolated from the stabilized sample are suitable for analysis. E.g. as described above, intracellular nucleic acids such as RNA can be isolated from the comprised cells and can be analyzed. Furthermore, the preservation of cells in the stabilized samples opens the possibility to sort or capture cells and even to enrich specific cells such as e.g. tumor cells that can then be analyzed specifically. E.g. circulating tumor cells can be isolated and their gene expression profile can be analyzed. Furthermore, the cell morphology and/or cell markers in particular cell surface markers can be analyzed in order to characterize the obtained cells. Furthermore, intracellular nucleic acids can be isolated from said enriched specific cells. E.g. RNA can be isolated from said cells. The transcript level stabilizing properties of the stabilizing method described herein advantageously allows using the isolated RNA for gene expression profiling and other important analyses. The stabilisation method described herein is thus advantageous for example in the molecular diagnostic of cancer or other diseases, because it allows an enrichment of cells prior to the extraction of the nucleic acids from the enriched cells and thereby increases e.g. the chance to detect rare events of circulating tumor cells in the cell-containing samples, for example in a blood sample. This also increases the chance that a specific biomarker, in particular a rare biomarker, is identified in the sample.

According to one embodiment, the cell-containing sample is a blood sample and wherein white blood cells are stabilized. This allows separating white blood cells from the stabilized sample. White blood cells are stabilized, if at least one type of the contained blood cells is stabilized during the stabilization period which preferably, is at least 48 h. According to one embodiment, lymphocytes and/or monocytes contained in the blood sample are stabilized. The stabilization described herein does not induce or promote the lysis of nucleated cells contained in the cell-containing sample. Thus, stabilization is not based on cell lysis.

Preferably, when the cell containing sample is blood and the nucleic acid of interest is extracellular nucleic acid, in particular extracellular RNA, the stabilization used herein prevents hemolysis. Most causes of in vitro hemolysis are related to specimen collection. However, in vitro hemolysis usually also occurs in a blood sample during ex vivo storage if no proper stabilization method is used. Depending on the extracellular nucleic acid of interest, hemolysis can be a considerable problem. If the extracellular nucleic acid of interest is DNA, hemolysis is less of a problem because red blood cells do not contain a nucleus and consequently, do not contain genomic DNA. Therefore, no intracellular DNA is released from the red blood cells during hemolysis. When the extracellular nucleic acid of interest is DNA, in particular the lysis or decay of white blood cells is a problem because in this case genomic DNA is released in addition to intracellular RNA. Therefore, when the extracellular nucleic acid of interest is extracellular DNA, in particular the lysis of white blood cells must be prevented. White blood cells may differ among each other in their stability characteristics. Thus, some types of white blood cells are more stable than others. However, generally, white blood cells are significantly more stable than red blood cells. Therefore, the lysis of red blood cells does not necessarily indicate that white blood cells were lysed. The different susceptibility of white blood cells and red blood cells to lysis is also used in the art to e.g. specifically lyse red blood cells, while preserving white cells in order to allow e. g. the collection of white blood cells. However, if the extracellular nucleic acid of interest is RNA, hemolysis and thus the lysis of red blood cells does constitute a problem. Mature red blood cells also do not contain RNA, however, their precursors (reticulocytes) do. Reticulocytes make up approximately 0.5% to 1% of the red blood cells and contain large amounts of globin RNA. Therefore, in particular when the extracellular nucleic acid of interest is RNA, a lysis of red blood cells and thus reticulocytes during storage should be prevented/reduced in order to reduce a dilution of the extracellular nucleic acid population, in particular the extracellular RNA population, with globin mRNA. Furthermore, as described above, it is important to maintain the composition and thus profile of the extracellular nucleic acid population what is achieved using stabilization methods described herein as this is important for many diagnostic applications. Hemolysis can be efficiently prevented/reduced when using the stabilization method according to the present invention. Thereby, the extracellular nucleic acid population is substantially preserved and furthermore, the stabilized blood sample, in particular the plasma or serum obtained from the stabilized blood sample, is due to the prevention of hemolysis and cell lysis in general also suitable for other standard laboratory analyses. Furthermore, prevention of lysis of white blood cells allows to isolate and analyse the respective cells. In particular, it allows isolating intracellular nucleic acids such as intracellular RNA from white blood cells or other preserved cells contained in the stabilized sample.

According to one embodiment, the morphology of cells is preserved during the stabilization period which preferably is at least 48 h. This allows analyzing and optionally characterizing contained cells based on their morphology. According to one embodiment, the morphology of nucleated cells is preserved. According to one embodiment, the morphology of lymphocytes contained in a blood sample is preserved during stabilization.

According to one embodiment, cell surface epitopes of cells are preserved. According to one embodiment, cell surface proteins such as CD proteins are preserved. The preservation of cell surface epitopes and cell surface proteins is an advantage as it allows characterizing and/or isolating contained cells based on these cell surface characteristics. In particular, it allows the analysis of tumor markers present on the cell surface or the isolation of specific cells based on said markers.

According to one embodiment, the stabilization method comprises contacting a blood sample with a primary and/or secondary carboxylic acid amide and an anticoagulant, wherein transcript levels in contained cells are stabilized. Furthermore, as is shown in the examples, the extracellular nucleic acid population is additionally stabilized. This is advantageous, as it allows to analyse the extracellular nucleic acids population separately from the intracellular nucleic acid population from the same stabilized sample. According to one embodiment, formamide is used for that purpose. According to one embodiment, butanamide is used for stabilizing the extracellular nucleic acid population.

According to one embodiment, a combination of stabilizing agents is used which comprises using at least one primary and/or secondary carboxylic acid amide and an apoptosis inhibitor. Already the apoptosis inhibitor alone is effective in stabilizing a cell-containing sample and to substantially preserve the extracellular nucleic acid population from changes in its composition in particular arising from contaminations with fragmented genomic DNA. Thus, the stabilization effect that is obtained when additionally using an apoptosis inhibitor is enhanced. The sample can be contacted with the apoptosis inhibitor, e.g. by adding the apoptosis inhibitor to the sample, or vice versa. Preferably, a stabilization composition comprising at least one primary and/or secondary carboxylic acid amide and an apoptosis inhibitor is used, in particular for stabilizing the extracellular nucleic acid population. The at least one apoptosis inhibitor present in the resulting mixture supports the stabilization of cells contained in the sample and inhibits the degradation of nucleic acids comprised in the sample thereby contributing to substantially preserving the extracellular nucleic acid population.

The term "apoptosis inhibitor" as used herein in particular refers to a compound whose presence in a cell-containing biological sample provides a reduction, prevention and/or inhibition of apoptotic processes in the cells and/or makes the cells more resistant to apoptotic stimuli. Apoptosis inhibitors include but are not limited to proteins, peptides or protein- or peptide-like molecules, organic and inorganic molecules. Apoptosis inhibitors include compounds that act as metabolic inhibitors, inhibitors of nucleic acid degradation respectively nucleic acid pathways, enzyme inhibitors, in particular caspase inhibitors, calpain inhibitors and inhibitors of other enzymes involved in apoptotic processes. Respective apoptosis inhibitors are listed in Table 1. Preferably, the at least one apoptosis inhibitor that is used for stabilizing the cell-containing biological sample is selected from the group consisting of metabolic inhibitors, caspase inhibitors and calpain inhibitors. Suitable examples for each class are listed in Table 1 in the respective category. Preferably, the apoptosis inhibitor is cell-permeable.

It is also within the scope of the present invention to use a combination of different apoptosis inhibitors, either from the same or a different class of apoptosis inhibitors, respectively to use a combination of different apoptosis inhibitors which inhibit apoptosis either by the same or a different working mechanism.

In an advantageous embodiment, the apoptosis inhibitor is a caspase inhibitor. Members of the caspase gene family play a significant role in apoptosis. The substrate preferences or specificities of individual caspases have been exploited for the development of peptides that successfully compete caspase binding. It is possible to generate reversible or irreversible inhibitors of caspase activation by coupling caspase-specific peptides to e.g. aldehyde, nitrile or ketone compounds. E.g. fluoromethyl ketone (FMK) derivatized peptides such as Z-VAD-FMK act as effective irreversible inhibitors with no added cytotoxic effects. Inhibitors synthesized with a benzyloxycarbonyl group (BOC) at the N-terminus and O-methyl side chains exhibit enhanced cellular permeability. Further suitable caspase inhibitors are synthesized with a phenoxy group at the C-terminus. An example is Q-VD-OPh which is a cell permeable, irreversible broad-spectrum caspase inhibitor that is even more effective in preventing apoptosis than the caspase inhibitor Z-VAD-FMK.

According to one embodiment, the caspase inhibitor used in addition to the at least one primary and/or secondary carboxylic acid amide is a pancaspase inhibitor and thus is a broad spectrum caspase inhibitor. According to one embodiment, the caspase inhibitor comprises a modified caspase-specific peptide. Preferably, said caspase-specific peptide is modified by an aldehyde, nitrile or ketone compound. According to a preferred embodiment, the caspase specific peptide is modified preferably at the carboxyl terminus with an O-Phenoxy or a fluoromethyl ketone (FMK) group. According to one embodiment, the caspase inhibitor is selected from the group consisting of Q-VD-OPh and Z-VAD(OMe)-FMK. In one embodiment, Z-VAD(OMe)-FMK, a pancaspase inhibitor, is used, which is a competitive irreversible peptide inhibitor and blocks caspase-1 family and caspase-3 family enzymes. In a preferred embodiment, Q-VD-OPh, which is a broad spectrum inhibitor for caspases, is used. Q-VD-OPh is cell permeable and inhibits cell death by apoptosis. Q-VD-OPh is not toxic to cells even at extremely high concentrations and consists of a carboxy terminal phenoxy group conjugated to the amino acids valine and aspartate. It is equally effective in preventing apoptosis mediated by the three major apoptotic pathways, caspase-9 and caspase-3, caspase-8 and caspase-10, and caspase-12 (Caserta et al, 2003). Further caspase inhibitors are listed in Table 1. According to one embodiment, the caspase inhibitor that is used as apoptosis inhibitor for stabilizing the cell-containing sample is one which acts upon one or more caspases located downstream in the intracellular cell death pathway of the cell, such as caspase-3. In one embodiment the caspase inhibitor is an inhibitor for one or more caspases selected from the group consisting of caspase-3, caspase-8, caspase-9, caspase-10 and caspase-12. It is also within the scope of the present invention to use a combination of caspase inhibitors.

When using a caspase inhibitor in addition to the at least one primary and/or secondary carboxylic acid amide, the mixture that is obtained after contacting the biological sample with the at least one apoptosis inhibitor may comprise the apoptosis inhibitor (or combination of apoptosis inhibitors) in a concentration selected from the group of at least 0.01 µM, at least 0.05 µM, at least 0.1 µM, at least 0.5 µM, at least 1 µM, at least 2.5 µM or at least 3.5 µM. Of course, also higher concentrations can be used. Suitable concentration ranges for the apoptosis inhibitor(s) when mixed with the cell-containing biological sample, include but are not limited to 0.01 µM to 100 µM, 0.05 µM to 100 µM, 0.1 µM to 50 µM, 0.5 µM to 50 µM, 1 µM to 40 µM, more preferably 1 µM to 30 µM or 2.5 µM to 25 µM. The higher concentrations were found to be more effective, however, good stabilizing results were also achieved at lower concentrations. Hence, an efficient stabilization is also achieved at lower concentrations e.g. in a range selected from 0.1 µM to 10 µM, 0.5 µM to 7.5 µM or 1 µM to 5 µM, in particular if the apoptosis inhibitor is used in combination. The above mentioned concentrations apply to the use of a single apoptosis inhibitor as well as to the use of a combination of caspase inhibitors. If a combination of caspase inhibitors is used, the concentration of an individual apoptosis inhibitor that is used in said mixture of apoptosis inhibitors may also lie below the above mentioned concentrations, if the overall concentration of the combination of apoptosis inhibitors fulfills the above mentioned features. Using a lower concentration that still efficiently stabilizes the cells and/or reduce the degradation of nucleic acids in present in the sample has the advantage that the costs for stabilisation can be lowered. Lower concentrations can be used because the apoptosis inhibitor is used in combination with one or more stabilizers as described herein. The aforementioned concentrations are in particular suitable when using a caspase inhibitor, in particular a modified caspase specific peptide such as Q-VD-OPh and/or Z-VAD(OMe)-FMK as apoptosis inhibitor. The above mentioned concentrations are e.g. very suitable for stabilizing whole blood, in particular 10 ml blood. Suitable concentration ranges for other apoptosis inhibitors and/or for other cell-containing biological samples can be determined by the skilled person using routine experiments, e.g. by testing the apoptosis inhibitors, respectively the different concentrations in the test assays described in the examples.

According to one embodiment, the apoptosis inhibitor will, in an effective amount, decrease or reduce apoptosis in a cell-containing biological sample by at least 25 percent, at least 30 percent, at least 40 percent, at least 50 percent, preferably, by at least 75 percent, more preferably, by at least 85 percent as compared to a control sample which does not contain a respective apoptosis inhibitor.

Thus, according to one embodiment, a combination of stabilizing agents is used which comprises at least one apoptosis inhibitor and at least one primary and/or secondary carboxylic acid amide, preferably selected from formamide and butanamide. A respective combination may also comprise additional additives that enhance the stabilizing effect such as e.g. anticoagulants and chelating agents. According to one embodiment, the combination of stabilizing agents comprises a caspase inhibitor and an anticoagulant, preferably a chelating agent such as EDTA. Respective combinations can be advantageously used in a method suitable for stabilizing an extracellular nucleic acid population comprised in a cell-containing sample according to the first aspect. The stabilizing effect observed with combinations of stabilizing agents is stronger than the effect observed for any of the individual stabilizing agents when used alone and/or allows using lower concentrations, thereby making combinatorial use of stabilizing agents an attractive option. Suitable and preferred embodiments of the apoptosis inhibitor and the at least one primary and/or secondary carboxylic acid amide, as well as suitable and preferred concentrations of the respective agents suitable for achieving an efficient stabilization of the sample are described in detail above.

As discussed in the background of the invention, extracellular nucleic acids are usually not present "naked" in the sample but are e.g. stabilized to a certain extent by being released protected in complexes or by being contained in vesicles and the like. This has the effect that extracellular nucleic acids are already to a certain extent stabilized by nature and thus, are usually not degraded rapidly by nucleases in cell-containing samples such as whole blood, plasma or serum. Thus, when intending to stabilize extracellular nucleic acids that are comprised in a biological sample, one of the primary problems is the dilution, respectively the contamination of the extracellular nucleic acid population by intracellular nucleic acids, in particular fragmented genomic DNA, that originates from damaged or dying cells that are contained in the sample. This also poses a problem when processing cell-depleted samples such as plasma or serum (which are sometimes also describes as being "cell-free" even though they may comprise minor amounts of cells). The stabilization technology according to the present invention is of particular advantage in this respect because it not only substantially preserves the extracellular nucleic acids present in the sample and e.g. inhibits degradation of the comprised extracellular nucleic acids (preferably at least by 60%, at least by 70%, at least by 75%, at least by 80%, at least by 85%, at least by 90% or most preferably at least by 95% over the stabilization period compared to an unstabilized sample or an EDTA stabilized sample) but furthermore, efficiently reduces the release of genomic DNA from cells contained in the sample and/or reduces the fragmentation of respective genomic DNA. According to one embodiment, using at least one primary and/or secondary carboxylic acid amide and optionally an apoptosis inhibitor for stabilizing the cell-containing sample according to the teachings of the present invention has the effect that the increase of DNA that results from a release of DNA from cells contained in the sample is reduced compared to a non-stabilized sample. According to one embodiment, said release of genomic DNA is reduced by at least 3-fold, at least 4-fold, at least 5-fold, at least 6-fold, at least 7-fold, at least 10-fold, at least 12-fold, at least 15-fold, at least 17-fold or at least 20-fold over the stabilization period compared to the non-stabilized sample or a corresponding sample that is stabilized with EDTA (in particular in case of a blood sample or a sample derived from blood such as plasma or serum). According to one embodiment, said release of genomic DNA is reduced by at least 60%, at least 70%, at least 75%, at least 80%, at least 85%, at least 90% or at least 95% over the stabilization period compared to the non-stabilized sample or a corresponding sample that is stabilized with EDTA (in particular in case of a blood sample or a sample derived from blood such as plasma or serum). The release of DNA can be determined e.g. by quantifying the ribosomal 18S DNA as is described herein in the example section. Thus, the extracellular nucleic acid population contained in the sample is considerably stabilized compared to samples stabilized in standard EDTA tubes. Thus, according to one embodiment, the stabilization effect that is achieved the compound according to formula 1 as taught by the present invention, which may be used in combination with an apoptosis inhibitor, results in that the release of DNA from cells contained in the sample is at least reduced to a maximum of 10-fold, preferably 7-fold, more preferably 5-fold and most preferably is at least reduced to a maximum of 4-fold, as is e.g. determinable in the 18S DNA assay described in the examples. As is shown by the examples, an effective stabilization of the extracellular nucleic acid population is achievable for a period of at least up to 6 days. During a shorter storage of the samples, e.g. up to three days, the DNA release can be reduced at least to a maximum of two-fold as e.g. determinable in the 18S DNA assay described in the examples. Thus, the DNA release can be reduced to 2fold or less up to three days of storage when using the stabilizing methods according to the present invention. This is a remarkable improvement in the stabilization of the extracellular nucleic acid population compared to the prior art methods. This significantly enhances the accuracy of any subsequent tests. In certain cases, for example if the sample material has to be transported for long distances or stored for longer periods e.g. at room temperature (as can be e.g. the case in certain countries), the process according to the invention makes it possible for the first time for these tests to be carried out after such a period of time. However, of course, the samples may also be further processed earlier, if desired. It is not necessary to make use of the full achievable stabilization period. The stabilization that is achieved with the present invention reduces variations in the extracellular nucleic acid population that may result from a different handling/processing of the samples (e.g. storage conditions and periods) after they were collected. This greatly improves the standardization of handling and molecular analysis.

Further additives may be used in addition to the at least one primary and/or secondary carboxylic acid amide in order to further stabilize the cell-containing sample. They may be used in addition to or as alternative to the apoptosis inhibitor. The selection of suitable additives that may also contribute to the stabilization effect may also depend on the type of cell-containing sample to be stabilized. E.g. when processing whole blood as cell-containing biological sample, it is advantageous and also common to include an anticoagulant e.g. selected from the group consisting of heparin, ethylenediamine tetraacetic acid, citrate, oxalate, and any combination thereof. In an advantageous embodiment, the anticoagulant is a chelating agent. A chelating agent is an organic compound that is capable of forming coordinate bonds with metals through two or more atoms of the organic compound. Chelating agents according to the present invention include, but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2EDTA$, $K_3EDTA$ or $Na_2EDTA$. Using a chelating agent such as EDTA also has the advantageous effect that nucleases such as DNases are inhibited, thereby e.g. preventing a degradation of extracellular DNA by DNases. Furthermore, it was found that EDTA used/added in higher concentrations is capable of reducing the release of intracellular nucleic acids, in particular genomic DNA, from the cells thereby supporting the stabilizing effect that is achieved by the at least one compound according to formula 1. However, EDTA alone is not capable of efficiently inhibiting the fragmentation of e.g. genomic DNA that is released from the cells contained in the sample. Thus, EDTA does not achieve a sufficient stabilization effect. But used in combination with the teachings of the present invention, in particular in combination with the apoptosis inhibitor, in particular the caspase inhibitor, it can further improve the stabilization for the above discussed reasons. Furthermore, it also appears to increase the chemical stability of RNA. According to one embodiment, the concentration of the chelating agent, preferably EDTA, in the biological sample that is mixed with one or more of the stabilizing compounds described above is in the range selected from the group consisting of 0.05 mM to 100 mM, 0.05 mM to 50 mM, 0.1 mM to 30 mM, 1 mM to 20 mM and 2 mM to 15 mM after the contacting step. Respective concentrations are particularly effective when stabilising blood, plasma and/or serum samples, in particular 10 ml blood samples.

Additional additives can also be used in order to further support the stabilization of the cell-containing sample, respectively support the preservation of the extracellular nucleic acid population. Examples of respective additives include but are not limited to nuclease inhibitors, in particular RNase and DNase inhibiting compounds. Examples of RNase inhibitors include but are not limited to anti-nuclease antibodies or ribonucleoside-vanadyl-complexes. When choosing a respective further additive, care should be taken not to compromise and/or counteract the stabilizing effect of the at least one primary and/or secondary carboxylic acid amide used as stabilizing agent. Thus, no additives should be used in concentrations that result in or support the lysis and/or degradation of the cells contained in the biological sample and/or which support the degradation of the nucleic acids contained in the cell-free fraction of the biological sample. Thus, no chaotropic salts should be used. Furthermore, also no additives should be used in concentration which counteract and overrule the transcriptome stabilizing effect of the at least one primary and/or secondary carboxylic acid amide that is used for stabilization.

According to one embodiment, the cell-containing sample is additionally contacted with at least one tertiary amide which is a compound according to formula 1

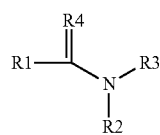

formula 1 wherein R1 is a hydrogen residue or an alkyl residue, wherein R2 and R3 are identical or different hydrocarbon residues with a length of the carbon chain of 1-20 atoms arranged in a linear or branched manner, and wherein R4 is an oxygen, sulphur or selenium residue, preferably R4 is oxygen.

R1 and R2 have the same meaning as R1 and R2 in the formula 1 describing the primary and secondary carboxylic acid amides (see above). Furthermore, in the tertiary amides, R3 may have the same meaning and thus is a hydrocarbon residue with a length of the carbon chain of 1-20 atoms arranged in a linear or branched manner. Suitable and preferred embodiments described for R2 also apply for R3 in the tertiary amides.

According to one embodiment, the tertiary amide according to formula 1 is a carboxylic acid amide. According to one embodiment, the tertiary amide according to formula 1 is a N,N-dialkylpropanamide, preferably N,N-dimethylpropanamide. According to one embodiment, the tertiary amide according to formula 1 is selected from the group consisting of N,N-dimethylformamide, N,N-dimethylacetamide, N,N-dimethylpropanamide, N,N-dimethylbutanamide.

According to one embodiment, after the cell-containing biological sample has been contacted with at least one primary or secondary carboxylic acid amide and a tertiary amide according to formula 1 and optionally further additives used for stabilization, the resulting mixture comprises the tertiary amide according to formula 1
i) in a concentration of at least 0.1%, at least 0.25%, at least 0.5%, at least 0.75%, at least 1%, at least 1.25% or at least 1.5%; and/or
ii) in a concentration that lies in the range of 0.1% to 30%, 0.25% to 20%, 0.5% to 15%, 0.7% to 10%, 0.8% to 7.5%, 0.9% to 6% or 1% to 5%.

According to one embodiment, the cell-containing biological sample to be stabilized is additionally contacted with at least one poly(oxyethylene) polymer as stabilizing agent. The term poly(oxyethylene) polymer in particular refers to an an oligomer or polymer of ethylene oxide. It comprises at least two ethylene oxide units. Poly(oxyethylene) polymers are known in low and high molecular weights. According to one embodiment, the molecular weight lies in a range of 200 to 20000 Da. The poly(oxyethylene) polymer may be linear or branched or may have other geometries. A linear poly(oxyethylene) polymer is preferred. The poly(oxyethylene) polymer may be unsubstituted or substituted and preferably is a polyethylene glycol. The polyethylene glycol preferably is unbranched and may be unsubstituted or substituted. Known substituted forms of polyethylene glycol include alkylpolyethylene glycols that are e.g. substituted at one or both ends with a C1-C5 alkyl group. Preferably, unsubstituted polyethylene glycol of the formula HO—$(CH_2CH_2O)_n$—H is used. All disclosures described in this application for the poly(oxyethylene) polymer in general, specifically apply and particularly refer to the preferred embodiment polyethylene glycol even if not explicitly stated. The poly(oxyethylene) polymer can be used in various molecular weights. Preferably, the term polyethylene glycol refers to oligomers or polymers as is also evident from the molecular weights specified herein as suitable and preferred for the poly(oxyethylene) polymer which specifically also apply to the preferred embodiment polyethylene glycol. The additional use of a poly(oxyethylene) polymer such as polyethylene glycol is advantageous as it was found that such polymers, in particular polyethylene glycol, stabilize cells and therefore can be used to support the stabilization effect on the cell-containing sample which preferably is a blood sample.

The stabilization methods as disclosed herein, provide a significant advantage over state-of-the-art stabilization methods that are based on the use of cross-linking reagents, such as formaldehyde, formaldehyde releasers and the like. Crosslinking reagents cause inter- or intra-molecular covalent bonds between nucleic acid molecules or between nucleic acids and proteins. This cross-linking effect can hamper the subsequent isolation of nucleic acids from such stabilized samples. As, for example, the concentration of circulating nucleic acids in a whole blood sample is already relatively low, any measure which further reduces the yield of such nucleic acids should be avoided. This may be of particular importance when detecting and analyzing very rare nucleic acid molecules derived e.g. from malignant tumors or from a developing fetus in the first trimester of pregnancy. As is shown by the examples, the method of the invention does not require cross-linking agents for stabilization. Therefore, according to one embodiment, the stabilization method according to the present invention does not involve the use of a cross-linking agent that induces protein-nucleic acid and/or protein-protein crosslinks. In particular, the stabilization does not involve the use of formaldehyde, formaline, paraformaldehyde or a formaldehyde releaser. Furthermore, the stabilization method according to the invention does not involve the use of additives that result in a lysis of nucleated cells.

In an advantageous embodiment of the present invention, the cell-containing biological sample, which preferably is a blood sample or a sample derived from blood such as plasma or serum, is contacted with:
a) at least one primary and/or secondary carboxylic acid amide, preferably formamide or butanamide (preferred concentrations are described above), and
b) at least one caspase inhibitor, preferably with Q-VD-OPh, preferably in a concentration range of 1 µM to 30 µM; and
c) a further additive, preferably a chelating agent preferably in a concentration range of 2 mM to 100 mM or 4 mM to 50 mM, preferably 4 mM to 20 mM, most preferably EDTA.

The components of the stabilizing composition can be comprised, respectively dissolved in a buffer, e.g. a biological buffer such as MOPS, TRIS, PBS and the like. Furthermore, they can be dissolved in water or any other suitable solvent. According to one embodiment, the stabilizing composition comprises a solvent such as DMSO.

The at least one primary and/or secondary carboxylic acid amide as well as the optionally present further additives can be e.g. present in a device, preferably a container, for collecting the sample or can be added to a respective collection device immediately prior to collection of the biological sample; or can be added to the collection device immediately after the sample was collected therein. Suitable and preferred primary and secondary carboxylic acid amides were described above and it is referred to the above disclosure which also applies here. According to one embodiment, formamide or butanamide is used for stabilization. It is also within the scope of the present invention to add the stabilizing agent(s) and optionally, the further additive(s) separately to the cell containing biological sample. However, for the ease of handling, it is preferred that the one or more stabilizing agents and optionally the further additives are provided in the respective collection device, e.g. in form of one composition. However, they may also be present as separate components or compositions in the collection device. Furthermore, in an advantageous embodiment, the at least one primary and/or secondary carboxylic acid amide and optionally the further additive(s) are present in the collection device prior to adding the sample. This ensures that the cell-containing biological sample is immediately stabilized upon contact with the stabilizing agent(s). The stabilisation agent(s) are present in the container in an amount effective to provide the stabilisation of the amount of cell containing sample to be collected, respectively comprised in said container. As described, the sample can be mixed with the stabilization agent(s) directly after and/or during collection of the sample thereby providing a stabilized sample. According to one embodiment, the stabilization involves the use of at least one poly(oxyethylene) polymer, preferably polyethylene glycol in, order to support the stabilization of the cells.

Preferably, the sample is mixed with the stabilization agent(s) directly after and/or during the collection of the sample. Therefore, preferably, the stabilization agent(s) and additives described above are provided in form of a stabilizing composition. Preferably, said stabilizing composition is provided in liquid form. It can be e.g. pre-filled in the sample collection device so that the sample is immediately stabilized during collection. According to one embodiment, the stabilizing composition is contacted with the cell-containing sample in a volumetric ratio selected from 10:1 to 1:20, 5:1 to 1:15, 1:1 to 1:10 and 1:2 to 1:5. It is a particular advantage of the teachings of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

The term "cell-containing sample" as used herein, in particular refers to a sample which comprises at least one cell. The cell-containing sample may comprise at least two, at least 10, at least 50, at least 100, at least 250, at least 500, at least 1000, at least 1500, at least 2000 or at least 5000 cells. Furthermore, also cell-containing samples comprising considerably more cells are encompassed by said term and can be stabilized with the teachings according to the present invention. However, the term "cell-containing sample" also refers to and thus encompasses cell-depleted samples, including cell-depleted samples that are commonly referred to as "cell-free" such as e.g. blood plasma as respective samples often include residual cells. At least, it can often not be fully excluded that even so-called "cell-free" samples such as blood plasma comprise residual amounts of cells which accordingly, pose a risk that the extracellular nucleic acid population becomes contaminated with intracellular nucleic acids released from said residual cells. Therefore, respective cell-depleted and "cell-free" samples are according to one embodiment also encompassed by the term "cell-containing sample". Thus, the "cell-containing sample" may comprise large amounts of cells, as is the case e.g. with whole blood, but may also only comprise merely minor amounts of cells. Hence, the term "cell containing sample" also encompasses samples that may only be suspected of or pose a risk of containing cells. As discussed above, also with respect to biological samples which only comprise minor, respectively residual amounts of cells such as e.g. blood plasma (blood plasma contains—depending on the preparation method—usually small residual amounts of cells, even though it is commonly referred to as being cell-free), the method according to the present invention has considerable advantages as these residual cells may also result in a undesired contamination of the comprised extracellular nucleic acids. Using the stabilizing technology of the present invention also ensures that respective samples which only comprise residual amounts of cells or are merely suspected of or pose a risk of residual amounts of cells, are efficiently stabilized as is also described in detail above. According to one embodiment, the cellular portion makes up at least 1%, at least 2%, at least 2.5%, at least 5%, preferably at least 10%, at least 15%, at least 20%, more preferably at least 25%, at least 30%, at least 35% or at least 40% of the cell-containing biological sample. Cell-containing samples wherein the cellular fraction makes up more than 40% can also be stabilized using teachings described herein. Using the stabilizing method according to the present invention has the advantage that irrespective of the composition of the sample and the number of cells contained therein, the extracellular nucleic acid population contained therein is substantially preserved, respectively stabilized, thereby allowing for standardizing the subsequent isolation and/or analysis of the contained extracellular nucleic acids.

According to one embodiment, the cell-containing biological sample is selected from the group consisting of whole blood, samples derived from blood, plasma, serum, sputum, lachrymal fluid, lymphatic fluid, urine, sweat, liquor, cerebrospinal fluid, ascites, milk, stool, bronchial lavage, saliva, amniotic fluid, nasal secretions, vaginal secretions, semen/seminal fluid, wound secretions, and cell culture supernatants and supernatants obtained from other swab samples. According to one embodiment, the cell-containing biological sample is a body fluid, a body secretion or body excretion, preferably a body fluid, most preferably whole blood, plasma or serum. The cell-containing biological sample comprises extracellular nucleic acids. According to another embodiment, the cell-containing biological sample is a non-fluid sample derived from a human or animal, such as e.g. stool, tissue or a biopsy sample. Other examples of cell-containing biological samples that can be stabilized with the method according to the present invention include but are not limited to biological samples cell suspensions, cell cultures, supernatant of cell cultures and the like, which comprise extracellular nucleic acids.

As is described above and as is demonstrated by the examples, using the methods of the present invention allows for stabilizing the cell-containing sample without refrigeration or freezing for a prolonged period of time period. Thus, the samples can be kept at room temperature or even at elevated temperatures e.g. up to 30° C. or up to 40° C. According to one embodiment, a stabilization effect is achieved for at least two days, preferably at least three days; more preferred at least one day to six days, most preferred for at least one day to at least seven days at room temperature. As is shown in the examples, the samples that were stabilized according to the method of the present invention were not substantially compromised when stored for 3 days at room temperature. Even during longer storages for up to 6 or even 7 days at room temperature the extracellular nucleic acid population was substantially more stabilized compared to non-stabilized samples or e.g. compared to samples that were stabilized using standard method such as an EDTA treatment. Even though the stabilization effect may decrease over time, it is still sufficient to preserve the composition of the extracellular nucleic acid population to allow the analysis and/or further processing. Thus, samples that were stabilized according to the methods of the present invention were still suitable for isolating and optionally analyzing the extracellular nucleic acids contained therein even after longer storage at room temperature. Furthermore, the transcriptome was efficiently stabilized. Thus, as the samples were not compromised in particular when using the preferred combination of stabilisation agents, even longer storage/shipping times are conceivable. However, usually, longer periods are not necessary, as the regular storage and e.g. shipping time to the laboratory, wherein the nucleic acid isolation and optionally analysis is performed, usually does not exceed 6 or 7 days, but usually is even completed after two or three days. As is shown in the examples, the stabilisation efficiency is particularly good during this time period. However, the extraordinary long stabilisation times and stabilisation efficiencies that are achievable with the method according to the present invention provides an important safety factor.

The methods and also the subsequently described compositions according to the present invention allow the stabilization also of large volumes of biological samples with small volumes of added substances because the additives that are used according to the teachings of the present invention are highly active. This is an important advantage because the size/volume of the sample poses considerable restrains on the subsequent isolation procedure in particular when intending to use automated processes for isolating the extracellular nucleic acids contained in the samples. Furthermore, one has to consider that extracellular nucleic acids are often only comprised in small amounts in the contained sample. Thus, processing larger volumes of a cell-containing sample such as e.g. a blood sample has the advantage that more circulating nucleic acids can be isolated from the sample and thus are available for a subsequent analysis.

The stabilization of the biological sample may either be followed directly by techniques for analysing nucleic acids, or the nucleic acids may be purified from the sample. Hence, the sample that was stabilized according to the method of the present invention can be analysed in a nucleic acid analytic and/or detection method and or may be further processed. E.g. extracellular nucleic acid can be isolated from the stabilized sample and can then be analysed in a nucleic acid analytic and/or detection method or may be further processed. Furthermore, cells can be removed from the stabilized sample and analysed and/or nucleic acids can be isolated from the obtained cells. Details regarding the nucleic acid isolation and analysis are described below in conjunction with the second aspect of the present invention and it is referred to said disclosure. As described, one important advantage of the stabilizing method according to the invention lies in that the subsequent isolation of nucleic acids is not hampered due to the stabilization as is, e.g., the case when using a cross-linking agent such as a formaldehyde releaser for stabilization. Furthermore, the cells can be analysed for their morphology or cell surface characteristics. This allows e.g. to identify tumor cells. According to one embodiment, intracellular RNA is isolated from the cells contained in the stabilized sample and analysed. According to one embodiment, the method comprises performing a qualitative or quantitative analysis of one or more gene transcripts.

Method for Isolating Nucleic Acids

Furthermore, according to a second aspect, a method for isolating nucleic acids from a biological sample is provided comprising the steps of:
 a) stabilizing a cell-containing sample according to the method according to the first aspect;
 b) isolating nucleic acids from the stabilized sample.
 According to one embodiment, said method comprises
 a) stabilizing a cell-containing sample according to the method according to the first aspect;
 b) isolating intracellular nucleic acids from the stabilized sample.

According to one embodiment, said method is for isolating extracellular nucleic acids from a cell-containing biological sample, wherein said method comprises the steps of:
 a) stabilizing the extracellular nucleic acid population comprised in a cell-containing sample according to the method defined in the first aspect of the present invention;
 b) isolating extracellular nucleic acids.

As discussed above, the stabilization according to the present invention has the effect that the extracellular nucleic acid population contained in the sample is substantially preserved in the state it had shown at the time the biological sample was obtained, respectively drawn. In particular, the usually observed high increase in nucleic acids that results from intracellular nucleic acids, in particular genomic DNA, more specifically fragmented genomic DNA, released from damaged or dying cells is efficiently reduced as is demonstrated in the examples. Therefore, the extracellular nucleic acids obtained from a respectively stabilized sample comprise fewer contaminations with intracellular nucleic acids originating from degraded or dying cells comprised in the sample and in particular comprise less amounts of fragmented genomic DNA compared to non-stabilized samples. Furthermore, the unique stabilization step allows to increase the amount of recoverable extracellular nucleic acids. The stabilization method according to the present invention can be performed without the crosslinking of the sample. This is an important advantage over the use of cross-linking agents such as formaldehyde or formaldehyde releasers, as these reagents might reduce the recoverable amount of extracellular nucleic acids due to cross-linking. Thus, the method according to the present invention improves the diagnostic and prognostic capability of the extracellular nucleic acids. Furthermore, said stabilization allows the sample to be stored and/or handled, e.g. transported,—even at room temperature—for a prolonged period of time prior to separating the cells contained in the sample and/or prior to isolating the extracellular nucleic acids comprised therein in step b). With respect to the details of the stabilization that is performed in step a), it is referred to the above disclosure which also applies here.

According to one embodiment, the cell-containing biological sample such as e.g. a whole blood sample is stabilized in step a) as is described in detail above using at least one primary or secondary carboxylic acid amide, and optionally, further additives. Suitable and preferred embodiments were described above. Particularly preferred is the additional use of a caspase inhibitor in combination with an anticoagulant, preferably a chelating agent as described above, for stabilizing whole blood samples.

If the sample comprises large amounts of cells as is e.g. the case with whole blood, the cells are separated from the remaining sample in order to obtain a cell-free, respectively cell-reduced or cell-depleted fraction of the sample which comprises the extracellular nucleic acids. Thus, according to one embodiment, cells are removed from the cell-containing sample between step a) and step b). This intermediate step is only optional and e.g. may be obsolete if samples are processed which merely comprise minor amounts of residual cells such as e.g. plasma or serum and/or wherein the extracellular nucleic acid of interest is DNA. Due to the stabilization of the invention, the release of genomic DNA during the stabilization period from the contained cells is reduced or even prevented and furthermore, in particular when using a caspase inhibitor in addition to butanamide, the fragmentation of genomic DNA is reduced. As described herein due to its considerably larger size, unfragmented genomic DNA can be distinguished from the smaller extracellular DNA. This allows to selectively isolate extracellular DNA even in the presence of unfragmented genomic DNA by using a size selective isolation protocol. However, in order improve the results, it is preferred that cells (or potentially remaining cells) are removed from the stabilized sample prior to isolating the extracellular nucleic acids in step b) in order to reduce contaminations of the extracellular nucleic acid population with intracellular nucleic acids that would otherwise be released from the cells during nucleic acid isolation. To remove the contained cells is in particular advantageous if the extracellular nucleic acids of interest are RNA, because it can be difficult to distinguish intracellular RNA from extracellular RNA and furthermore, a dilution of the extracellular RNA can thereby be prevented. However, a cell removal step prior to step b) is generally advantageous and thus preferred, also if the extracellular nucleic acid of interest is DNA, because this allows to use standard nucleic acid isolation procedures in step b). Depending on the type of cell-containing biological sample, cells, including residual cells, can be separated and removed e.g. by centrifugation, preferably high speed centrifugation, or by using means other than centrifugation, such as e.g. filtration, sedimentation or binding to surfaces e.g. on (optionally magnetic) particles if a centrifugation step is to be avoided. Respective cell separation methods are well-known in the prior art and thus, do not need to be described in detail. Respective cell removal steps can also be easily included into an automated sample preparation protocol. Respectively removed cells may also be processed further if desired. The cells can e.g. be stored, analysed and/or biomolecules such as e.g.

nucleic acids or proteins can be isolated from the removed cells. Furthermore, it was found that intracellular nucleic acids such as intracellular RNA can be stabilized using the methods described herein (see above). The additional stabilization of the transcriptome is advantageous as it allows e.g. to analyse profiles of transcripts in the isolated intracellular nucleic acids which can also be important biomarkers for in vitro diagnostics.

Furthermore, it is also within the scope of the present invention to include further intermediate steps to work up the sample.

Extracellular nucleic acids are then isolated in step b), e.g. from the cell-free, respectively cell-depleted fraction, e.g. from supernatants, plasma and/or serum. For isolating extracellular nucleic acids, any known nucleic acid isolation method can be used that is suitable for isolating nucleic acids from the respective sample, respectively the cell-depleted sample. Examples for respective purification methods include but are not limited to extraction, solid-phase extraction, silica-based purification, magnetic particle-based purification, phenol-chloroform extraction, chromatography, anion-exchange chromatography (using anion-exchange surfaces), electrophoresis, filtration, precipitation, chromatin immunoprecipitation and combinations thereof. It is also within the scope of the present invention to specifically isolate specific target extracellular nucleic acids, e.g. by using appropriate probes that enable a sequence specific binding and are coupled to a solid support. Also any other nucleic acid isolating technique known by the skilled person can be used. According to one embodiment, the nucleic acids are isolated using a chaotropic agent and/or alcohol. Preferably, the nucleic acids are isolated by binding them to a solid phase, preferably a solid phase comprising silica or anion exchange functional groups. Suitable methods and kits are also commercially available such as the QIAamp® Circulating Nucleic Acid Kit (QIAGEN), the Chemagic Circulating NA Kit (Chemagen), the NucleoSpin Plasma XS Kit (Macherey-Nagel), the Plasma/Serum Circulating DNA Purification Kit (Norgen Biotek), the Plasma/Serum Circulating RNA Purification Kit (Norgen Biotek), the High Pure Viral Nucleic Acid Large Volume Kit (Roche) and other commercially available kits suitable for extracting and purifying circulating nucleic acids.

According to one embodiment, total nucleic acids comprised in the sample that is obtained after step a) or optionally obtained after the cells have been removed in the intermediate step are isolated, e.g. are isolated from the, or a cell-free, respectively cell-depleted fraction. E.g. total nucleic acids can be isolated from plasma or serum and the extracellular nucleic acids will be comprised as a portion in these extracted nucleic acids. If the cells are efficiently removed, the total nucleic acids isolated will predominantly comprise or even consist of extracellular nucleic acids.

It is also within the scope of the present invention to isolate at least predominantly a specific target nucleic acid. A target nucleic acid can be e.g. a certain type of extracellular nucleic acid, e.g. DNA or RNA, including mRNA, microRNA, other non-coding nucleic acids, epigenetically modified nucleic acids, and other nucleic acids. E.g. the target extracellular nucleic acid can be DNA and the non-target extracellular nucleic acid can be RNA or vice versa. Target specific nucleic acid isolation methods which specifically aim at isolating DNA or RNA are also well known in the prior art and thus, do not need any detailed description herein. According to one embodiment, the non-target nucleic acid is destroyed by adding an appropriate enzyme which specifically destroys the non-target nucleic acid, e.g. a RNase if the target nucleic acid is DNA or a DNase if the target nucleic acid is RNA. Said enzyme can be added to the lysis or binding mixture or can be added after extracellular nucleic acids were bound to a solid phase. Suitable embodiments for performing a respective non-target nucleic acid digestion step are known in the prior art and thus, do not need any further description herein. According to one embodiment which is feasible if DNA and RNA are bound to a solid support, elution conditions selective for the target nucleic acid can be applied to predominantly and thus selectively recover the target nucleic acid from the solid support. According to one embodiment, an isolation method is used, wherein the target nucleic acid, e.g. DNA, is selectively bound to a solid phase under conditions wherein non-target nucleic acids, e.g. RNA do not bind. Suitable binding conditions are well-known in the prior art and are e.g. described in WO 95/21849. According to one embodiment, the non-target nucleic acid is removed by binding at least a portion of the non-target nucleic acid under appropriate conditions to a solid phase and then separating the non-target nucleic acid bound to the solid phase from the remaining sample comprising the target extracellular nucleic acid. This can be achieved e.g. by the addition of a suitable solid phase under conditions wherein mainly the non-target nucleic acids e. g. DNA are bound to the solid phase while the non-target nucleic acid, e.g. RNA, remains in the sample and is recovered therefrom in a separate step. Suitable methods for selectively removing a non-target nucleic acid from a target nucleic acid are for example described in EP 0 880 537 and WO 95/21849, herein incorporated by reference. If desired, said non-target nucleic acid may also be further used, e.g. further processed such as e.g. eluted from the solid phase. However, it may also be discarded. It is also within the scope of the present invention to e.g. digest the non-target nucleic acid or remainders thereof using nucleases after isolation of the target nucleic acid.

The term target nucleic acid may also refer to a specific kind of nucleic acid, e.g. a specific extracellular nucleic acid that is known to be a certain disease marker. As discussed above, the isolation of extracellular nucleic acids may also comprise the specific isolation of a respective target nucleic acid e.g. by using appropriate capture probes which support the selective isolation of the target nucleic acid.

The term target nucleic acid may also refer to nucleic acids having a certain length, e.g. a nucleic acid having a length of 5000 nt or less, 2000 nt or less, 1000 nt or less, 900 nt or less, 800 nt or less, 700 nt or less, 600 nt or less, 500 nt or less, 400 nt or less or 350 nt or less. Isolating target nucleic acids of a certain maximum size can be advantageous in the context of the present invention. It is known that extracellular nucleic acids usually have a size of less than 2000 nt, less than 1000 nt and often even less than 500 nt. The sizes, respectively size ranges indicated herein refer to the chain length. I.e. in case of double-stranded nucleic acids such as double-stranded DNA it refers to bp. Selectively isolating smaller nucleic acids in step b) can increase the portion of extracellular nucleic acids obtained in the isolated nucleic acids. The stabilization methods according to the present invention allow, in particular due to the inhibition of the release of genomic DNA and/or the inhibition of the fragmentation of released genomic DNA, for a more efficient separation of such high molecular weight genomic DNA from the smaller extracellular nucleic acid population. As the substantial size difference between genomic DNA and extracellular nucleic acids is essentially preserved using the stabilization technology according to the present invention, genomic DNA can be removed more efficiently e.g. using a size selective nucleic acid isolation protocol. As the size difference between genomic DNA (usually larger than >10,000 bp) and extracellular nucleic acids (usually <1000 nt/bp) in a sample stabilized as described herein is usually relatively large due to the efficient stabilization, known methods for selectively isolating nucleic acids of a certain target length can be used. Thus, according to one embodiment, step b) comprises selectively isolating target nucleic acids having a length of 5000 nt or less, 2000 nt or less, 1500 nt or less, 1000 nt or less, 900 nt or less, 800 nt or less, 700 nt or less, 600 nt or less or 500 nt or less. Suitable methods to achieve a respective size selective isolation of nucleic acids e.g. by depleting high molecular weight genomic DNA, are known in the prior art and thus, need no detailed description herein. A classic method for isolating DNA of a target size involves the separation of the DNA in a gel, cutting out the desired gel band(s) and then isolating the DNA of the target size from the gel fragment(s). Another widely used technology is the size selective precipitation with polyethylene glycol based buffers (Lis and Schleif Nucleic Acids Res. 1975 Mar;2(3):383-9) or the binding/precipitation on carboxyl-functionalized beads (DeAngelis et al, Nuc. Acid. Res. 1995, Vol 23(22), 4742-3; U.S. Pat. Nos. 5,898,071 and 5,705,628, commercialized by Beckman-Coulter (AmPure XP; SPRIselect) and U.S. Pat. No. 6,534,262). Furthermore, size selective isolation methods that are based on the use of solid supports comprising anion exchange groups and varying pH values are known. A size selective isolation provides further opportunities in order to reduce the amount of intracellular nucleic acids in the isolated extracellular nucleic acids. For example, when the target extracellular nucleic acid of interest is DNA, the removal of genomic DNA during nucleic acid isolation step b) could also supplement or even replace a separate high g-force centrifugation of a plasma sample before starting the nucleic acid extraction in order to remove residual cells. Genomic DNA that is released from said residual cells is prevented from becoming massively degraded due to the stabilization according to the present invention, in particular if a caspase inhibitor is used in addition to the at least one primary and/or secondary carboxylic acid amide, and accordingly, said unfragmented or less fragmented genomic DNA can be depleted by using a size-selective nucleic acid isolation protocol in step b). This option is of particular advantage, as many clinical laboratories do not have a centrifuge capable of performing such a high g-force centrifugation or other means for removing in particular trace amounts of residual cells.

Furthermore, intracellular nucleic acids can be isolated from contained cells, e.g. after the cells were separated from the remaining sample. E.g. RNA can be isolated and used for gene expression analysis.

The isolated nucleic acids can then be analyzed and/or further processed in a step c) using suitable assay and/or analytical methods. E.g. they can be identified, modified, contacted with at least one enzyme, amplified, reverse transcribed, cloned, sequenced, contacted with a probe, be detected (their presence or absence) and/or be quantified. Respective methods are well-known in the prior art and are commonly applied in the medical, diagnostic and/or prognostic field in order to analyze extracellular nucleic acids (see also the detailed description in the background of the present invention). Thus, after extracellular nucleic acids were isolated, optionally as part of total nucleic acid, total RNA and/or total DNA (see above), they can be analyzed to identify the presence, absence or severity of a disease state including but not being limited to a multitude of neoplastic diseases, in particular premalignancies and malignancies such as different forms of cancers. E.g. the isolated extracellular nucleic acids can be analyzed in order to detect diagnostic and/or prognostic markers (e.g., fetal- or tumor-derived extracellular nucleic acids) in many fields of application, including but not limited to non-invasive prenatal genetic testing respectively screening, disease screening, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease or a fetal characteristic. Thus, as discussed above, the isolation method described herein may further comprise a step c) of nucleic acid analysis and/or processing. Therefore, according to one embodiment, the isolated extracellular nucleic acids are analyzed in step c) to identify, detect, screen for, monitor or exclude a disease and/or at least one fetal characteristic.

The analysis/further processing of the nucleic acids can be performed using any nucleic acid' analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

According to one embodiment, either or both of the isolating or analyzing steps b) and c) occurs at least one day up to 7 days after the sample has been collected, respectively stabilized according to the teachings of the present invention. Suitable time periods for which the sample, in particular a blood sample, respectively the extracellular nucleic acid population contained therein can be stabilized using the method according to the present invention are also described above and also apply here. According to one embodiment, the isolation step is performed at least one day, at least 2 days, at least 3 days, at least 4 days, at least 5 days or at least 6 days after the sample was collected and stabilized according to the method according to the present invention. According to one embodiment, either or both of the isolating or analyzing steps occur without freezing the sample and/or without the use of formaldehyde or a formaldehyde releaser for preserving the cell-containing biological sample. The biological sample is stabilized after the contact with the at least one primary or secondary carboxylic acid amide which preferably is a compound according to formula 1 as defined above, preferably in combination with a further additive such as an anticoagulant like EDTA. An anticoagulant is preferably used when stabilizing blood or a sample derived from blood. The respectively stabilized samples can be handled, e.g. stored and/or shipped at room temperature. As described above, according to one embodiment, an apoptosis inhibitor, preferably a caspase inhibitor is additionally used for stabilization.

Composition

Furthermore, according to a third aspect of the present invention a composition suitable for stabilizing a biological sample is provided, comprising:
  a) at least one carboxylic acid amide, preferably in a concentration of at least 1%, wherein the carboxylic acid amide is selected from primary carboxylic acid amides and secondary carboxylic acid amides; and
  b) at least one anticoagulant.

As discussed above, a respective stabilizing composition is particularly effective in stabilizing a cell-containing biological sample, in particular whole blood, plasma and/or serum by stabilizing the comprised cells, transcript levels and the comprised extracellular nucleic acids thereby substantially preserving, respectively stabilizing the extracellular nucleic acid population. A respective stabilizing composition allows the storage and/or handling, e.g. shipping, of the sample, which preferably is whole blood, at room temperature for at least two, preferably at least three days without substantially compromising the quality of the sample, respectively the extracellular nucleic acid population contained therein. Furthermore, the gene expression profile on thus the transcriptome of contained cells is preserved. Of course, it is not mandatory to make use of the full possible stabilization period; the samples may also be processed earlier if desired. Contacting the biological sample with the stabilizing composition allows the sample to be stored, and or handled, e.g. shipped, even at room temperature prior to isolating and optionally analyzing and/or processing the contained nucleic acids. Thus, the time between the collection or stabilization of the sample and the nucleic acid extraction can vary without substantially affecting the population, respectively the composition of the extracellular nucleic acid population contained therein. In particular, dilutions, respectively contaminations with intracellular nucleic acids, in particular fragmented genomic DNA, are reduced. Furthermore, as the gene transcription profile of contained cells is stabilized, intracellular RNA can be isolated and e.g. used in methods that analyze gene expression and can be used for gene expression profiling. Preferably, the stabilization composition is contacted with the sample immediately after or during collection of the sample. The stabilization composition may also comprise further stabilizing agents as described herein, e.g. an apoptosis inhibitor, which preferably is a caspase inhibitor.

Suitable and preferred embodiments of primary and secondary carboxylic acid amides and the apoptosis inhibitor as well as suitable and preferred concentrations of the respective compounds when mixed with the cell-containing sample are described in detail above in conjunction with the stabilization method. It is referred to the above disclosure which also applies with respect to the stabilization composition. Said compound can also be used in combination with an apoptosis inhibitor, preferably a caspase inhibitor (preferred embodiments are described above, it is referred to the above disclosure). Furthermore, a tertiary amide as described can be used in combination. Preferred and suitable embodiments as well as suitable concentrations were described above and it is referred to the above disclosure which also applies here. According to one embodiment, the stabilizing agent is a primary carboxylic acid amide selected from butanamide and formamide. As butanamide is non-toxic, it is particularly preferred. As described herein, butanamide is particularly effective for stabilizing the extracellular nucleic acid population. According to one embodiment, formamide is used as stabilizing agent. As is shown by the examples, formamide is highly effective in stabilizing the extracellular nucleic acid population as well as the transcriptome of contained cells. Thus, advantageously, formamide can be used for both stabilization purposes. According to one embodiment, the primary carboxylic acid amide is not propanamide.

According to one embodiment, the composition additionally comprises at least one poly(oxyethylene) polymer, preferably a polyethylene glycol. The molecular weight may lie in a range of e.g. 200 to 20000 Da. Including a polyethylene glycol in the stabilization composition is advantageous, because it supports and thus assists the stabilization of the cells contained in the sample to be stabilized.

Furthermore, it is preferred that the stabilization composition comprises further additives, e.g. an anticoagulant such as a chelating agent in particular if the composition is used for stabilizing whole blood, plasma or serum.

The stabilizing composition provided by the present invention stabilizes the cell-containing biological sample and thus, does not induce the lysis and/or disruption of nucleated cells and preferably also anucleated cells, contained in the sample. Therefore, the stabilization composition does not comprise additives in a concentration wherein said additives would induce or promote cell lysis of respective cells and preferably cells in general. The stabilizing composition may reduce the damage of cells comprised in the sample as can be e.g. determined by the assay methods described in the example section. In particular, the stabilization composition described herein is according to one embodiment capable of reducing the release of genomic DNA from cells contained in the cell-containing biological sample into the cell-free portion of the sample. Furthermore, in particular when comprising a caspase inhibitor, the stabilization composition may be capable of reducing the degradation of nucleic acids, in particular genomic DNA, present in the stabilized sample. As described, the stabilization composition is capable of reducing or preventing the contamination of the extracellular DNA population comprised in the biological sample with genomic DNA originating from cells contained in the stabilized sample. Preferably, it is capable of reducing or preventing the contamination of the extracellular nucleic acid population comprised in the biological sample with intracellular nucleic acids, in particular DNA and RNA, originating from cells contained in the stabilized sample. Preferably, the stabilization composition does not comprise a cross-linking agent that induces protein-DNA and/or protein-protein crosslinks. In particular, the stabilization composition does not comprise formaldehyde, formaline, paraformaldehyde or a formaldehyde releaser or similar crosslinking agents. Furthermore, as described herein and shown by the examples, according to one embodiment the stabilization composition results in a stabilization of the transcriptome.

According to one embodiment, the stabilizing composition consists essentially of the mentioned stabilizers and optional additives and optionally, buffering agents. The stabilizing composition stabilizes the sample and thus, does not promote the lysis and/or disruption of the cells contained in the sample. The stabilizing composition may reduce the damage of the cells comprised in the sample as can be e.g. determined by the assay methods described in the example section.

The composition may be provided in a solid form. This is e.g. a suitable option if the biological sample to be stabilized contains liquid to dissolve the solid (such as for example cell-containing body fluids, cells in medium, urine) or if liquid, e.g. water is added thereto to dissolve the solid. The advantage of using a solid stabilizing composition is that solids are usually chemically more stable. However, also a liquid composition may be used. Liquid compositions often have the advantage that the mixture with the sample to be stabilised can be quickly achieved, thereby basically providing an immediate stabilising effect as soon as the sample comes into contact with the liquid stabilizing composition. Preferably, stabilising agent(s) present in the liquid stabilizing composition remain stable in solution and require no pre-treatment-such as for example the dissolving of precipitates of limited solubility-by the user because pre-treatments of this kind pose a risk of variations in the stabilising efficiency.

Also provided is a mixture comprising the stabilizing composition according to the present invention mixed with a biological sample. Suitable and preferred examples of biological samples as well as suitable concentrations of the stabilizing agent(s) when mixed with the biological sample are described above in conjunction with the stabilizing method. It is referred to the above disclosure which also applies here. Preferably, the stabilizing composition is pre-filled in a sample collection device so that the sample is immediately stabilized during collection. According to one embodiment, the stabilizing composition is contacted with the biological sample, preferably a blood sample, in a volumetric ratio selected from 10:1 to 1:20, 5:1 to 1:15, 1:1 to 1:10 and 1:2 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

Uses

The stabilizing composition according to the third aspect of the present invention can be used to stabilize the extracellular nucleic acid population comprised in a cell-containing sample. Furthermore, the stabilizing composition according to the third aspect of the present invention may also be used for stabilizing cells contained in a sample. As described above, the stabilizing composition inter alia reduces the release of genomic DNA from cells that results from decaying cells. Thus, a respective use is also an advantageous and provided by the teachings according to the present invention. Furthermore, the stabilizing composition according to the third aspect of the present invention may also be used for stabilizing transcript levels in contained cells.

Manufacturing Method

Also provided is a method of manufacturing a composition according to the third aspect of the present invention is provided, wherein the components of the composition are mixed, preferably in an aqueous solution.

The composition of the present invention may also be incorporated into a sample collection device, in particular blood collection assembly, thereby providing for a new and useful version of such a device. Such devices typically include a container having an open and a closed end. The container is preferably a blood collection tube. The container type also depends on the sample to be collected, other suitable formats are described below.

Container

Furthermore, the present invention provides a container for collecting a cell-containing biological sample, preferably a blood sample, which comprises a) at least one carboxylic acid amide, preferably in a concentration of at least 1%, wherein the carboxylic acid amide is selected from primary carboxylic acid amides and secondary carboxylic acid amides; and b) at least one anticoagulant.

The container for collecting a cell-containing biological sample, preferably a blood sample, may comprise a stabilizing composition according to the present invention. Providing a respective container, e.g. a sample collection tube, which comprises the mentioned components or the stabilizing composition according to the present invention, has the advantage that the sample is quickly stabilized when the sample is collected in the respective container. Details with respect to the use of the agents used for stabilizing and the stabilizing composition were described above, it is referred to the above disclosure which also applies here.

According to one embodiment, a collection container for receiving and collecting a biological sample is provided wherein the container comprises:

a) at least one carboxylic acid amide, preferably in a concentration of at least 1%, wherein the carboxylic acid amide is selected from primary carboxylic acid amides and secondary carboxylic acid amides; and b) at least one anticoagulant.

Suitable embodiments and concentrations are also described above in conjunction with the method and it is referred to the above disclosure. According to one embodiment, the primary carboxylic acid amide is selected from butanamide and formamide. According to one embodiment, the container additionally comprises at least one apoptosis inhibitor such that when the sample is collected, the concentration of the apoptosis inhibitor or combination of two or more apoptosis inhibitors in the resulting mixture is selected from at least 0.01 µM, at least 0.05 µM, at least 0.1 µM, at least 0.5 µM, at least 1 µM, at least 2.5 µM or at least 3.5 µM and preferably is present in a concentration range selected from 0.01 µM to 100 µM, 0.05 µM to 100 µM, 0.1 µM to 50 µM, 1 µM to 40 µM, 1.0 µM to 30 µM or 2.5 µM to 25 µM. According to one embodiment, the container additionally comprises at least one poly(oxyethylene) polymer, preferably at least one polyethylene glycol. Details were described above and it is referred to the above disclosure.

The pre-filled components can be provided in a liquid or in a dry form. According to one embodiment, the stabilizing components are provided as a stabilizing composition. A dry form is e.g. a suitable option if the biological sample to be stabilized contains liquid to dissolve the solid (such as for example cell-containing body fluids, cells in medium, urine) or if liquid, e.g. water is added thereto to dissolve the solid. The advantage of using a solid stabilizing composition is that solids are usually chemically more stable than liquids. According to one embodiment, the inner wall of the container is treated/covered with a stabilizing composition according to the present invention. Said composition can be applied to the inner walls using e.g. a spray-dry-method. Liquid removal techniques can be performed on the stabilising composition in order to obtain a substantially solid state protective composition. Liquid removal conditions may be such that they result in removal of at least about 50% by weight, at least about 75% by weight, or at least about 85% by weight of the original amount of the dispensed liquid stabilising composition. Liquid removal conditions may be such that they result in removal of sufficient liquid so that the resulting composition is in the form of a film, gel or other substantially solid or highly viscous layer. For example it may result in a substantially immobile coating (preferably a coating that can be re-dissolved or otherwise dispersed upon contact with the cell-containing sample which preferably is a blood product sample). It is possible that lyophilization or other techniques may be employed for realizing a substantially solid form of the protective agent (e.g., in the form of one or more pellet). Thus, liquid removal conditions may be such that they result in a material that upon contact with the sample under consideration (e.g., a whole blood sample) the protective agent will disperse in the sample, and substantially preserve components (e.g., extracellular nucleic acids) in the sample. Liquid removal conditions may be such that they result in a remaining composition that is substantially free of crystallinity, has a viscosity that is sufficiently high that the remaining composition is substantially immobile at ambient temperature; or both.

According to one embodiment, a liquid composition is used. Liquid compositions often have the advantage that the mixture with the sample to be stabilised can be quickly achieved, thereby basically providing an immediate stabilising effect as soon as the sample comes into contact with the liquid stabilizing composition. Preferably, the stabilising agent(s) present in the liquid stabilizing composition remain stable in solution and require no pre-treatment-such as for example the dissolving of precipitates of limited solubility-by the user because pre-treatments of this kind pose a risk of variations in the stabilising efficiency.

The stabilizing composition is comprised in the container in an amount effective to provide the stabilisation of the amount of sample to be collected in said container. According to one embodiment, the liquid stabilizing composition is contacted with the biological sample in a volumetric ratio selected from 10:1 to 1:20, 5:1 to 1:15, 1:1 to 1:10 and 1:2 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

According to one embodiment, the container is evacuated. The evacuation is preferably effective for drawing a specific volume of a fluid sample into the interior. Thereby, it is ensured that the correct amount of sample is contacted with the pre-filled amount of the stabilizing composition comprised in the container, and accordingly, that the stabilization is efficient. According to one embodiment, the container comprises a tube having an open end sealed by a septum. E.g. the container is pre-filled with a defined amount of the stabilizing composition either in solid or liquid form and is provided with a defined vacuum and sealed with a septum. The septum is constructed such that it is compatible with the standard sampling accessories (e.g. cannula, etc.). When contacted with e.g. the canula, a sample amount that is predetermined by the vacuum is collected in the container. A respective embodiment is in particular advantageous for collecting blood. A suitable container is e.g. disclosed in U.S. Pat. No. 6,776,959.

The container according to the present invention can be made of glass, plastic or other suitable materials. Plastic materials can be oxygen impermeable materials or may contain an oxygen impermeable layer. Alternatively, the container can be made of water- and air-permeable plastic material. The container according to the present invention preferably is made of a transparent material. Examples of suitable transparent thermoplastic materials include polycarbonates, polyethylene, polypropylene and polyethyleneterephthalate. The container may have a suitable dimension selected according to the required volume of the biological sample being collected. As described above, preferably, the container is evacuated to an internal pressure below atmospheric pressure. Such an embodiment is particularly suitable for collecting body fluids such as whole blood. The pressure is preferably selected to draw a predetermined volume of a biological sample into the container. In addition to such vacuum tubes also non-vacuum tubes, mechanical separator tubes or gel-barrier tubes can be used as sample containers, in particular for the collection of blood samples. Examples of suitable containers and capping devices are disclosed in U.S. Pat. No. 5,860,397 and US 2004/0043505. As container for collecting the cell-containing sample also further collection devices, for example a syringe, a urine collection device or other collection devices can be used. The type of the container may also depend on the sample type to be collected and suitable containers are also available to the skilled person.

Beneficial results are obtained when the container respectively the device is filled or is pre-filled with at least one compound according to formula 1 as defined above as stabilizing agent. Preferably, an anticoagulant is encompassed in addition to the primary or secondary carboxylic acid amide described above which preferably is selected from formamide and butanamide. The anticoagulant is preferably a chelating agent such as EDTA. Furthermore, the stabilizing composition comprised in the container may also comprise an apoptosis inhibitor, preferably a caspase inhibitor and optionally further additives. According to one embodiment, the stabilizing composition comprised in the container comprises a caspase inhibitor and an anticoagulant. According to one embodiment, the stabilizing composition comprises a tertiary amide as described above.

According to one embodiment, the container has an open top, a bottom, and a sidewall extending therebetween defining a chamber, wherein the stabilizing agents and/or the stabilization composition according to the present invention is comprised in the chamber. It may be comprised therein in liquid or solid form. According to one embodiment the container is a tube, the bottom is a closed bottom, the container further comprises a closure in the open top, and the chamber is at a reduced pressure. The advantages of a reduced pressure in the chamber were described above. Preferably, the closure is capable of being pierced with a needle or cannula, and the reduced pressure is selected to draw a specified volume of a liquid sample into the chamber. According to one embodiment, the chamber is at a reduced pressure selected to draw a specified volume of a liquid sample into the chamber, and the stabilizing composition is a liquid and is disposed in the chamber such that the volumetric ratio of the stabilising composition to the specified volume of the cell-containing sample is selected from 10:1 to 1:20, 5:1 to 1:15, 1:1 to 1:10 and 1:2 to 1:5. The associated advantages were described above.

Preferably, the container is for drawing blood from a patient.

Collection Method

According to a fifth aspect, a method is provided comprising the step of collecting a sample from a patient directly into a chamber of a container according to the fourth aspect of the present invention. Details with respect to the container and the sample were described above. It is referred to the respective disclosure. According to one embodiment, a blood sample is collected, preferably it is withdrawn from the patient.

The methods and compositions disclosed herein allow for the efficient preservation and isolation of extracellular nucleic acids while reducing possible mixing with nucleic acids, in particular fragmented genomic DNA, which originates from cells comprised in the biological sample and which may enter a biological sample due to cell damage, respectively cell lysis. The methods according to the present invention, as well as the compositions and the disclosed devices (e.g. the collection containers) reduce the degradation of extracellular nucleic acids and also reduce cell lysis and/or release of genomic nucleic acids, in particular fragmented genomic DNA, so that the extracellular nucleic acids contained in the sample do not become contaminated with intracellular nucleic acids, respectively a respective contamination is reduced by the teachings according to the present invention. As discussed above, an intermixing of extracellular nucleic acids and intracellular nucleic acids, in particular fragmented genomic DNA, may reduce the accuracy of any measurement of the amount of extracellular nucleic acids in a biological sample. As discussed above, an important advantage of the present invention is the possibility for essentially simultaneous stabilizing of both the cells contained in the sample (in particular white blood cells or types of white blood cells in case of whole blood, plasma or serum) and the extracellular nucleic acids. This helps to prevent cellular nucleic acids such as genomic DNA from being released into the cell-free portion of the sample, and further diluting the comprised extracellular nucleic acids (and associated biomarkers) of interest, while also maintaining the structural integrity of the extracellular nucleic acids. As discussed herein, contacting the cell-containing biological sample such as whole blood or plasma with the stabilising agent(s) allows the sample to be stored for a period of time prior to isolating the extracellular nucleic acids. More preferably, the cell-containing biological sample, e.g. blood or plasma, may be drawn at one location (e.g., a health care facility), contacted with the stabilising agent(s), and later transported to a different remote location (e.g., a laboratory) for the nucleic acid isolation and testing process. Furthermore, the stabilization technologies described herein allow to stabilize intracellular nucleic acids and in particular transcript levels as was described in detail above. The stabilization of the transcriptome that can be achieved with the methods and composition described herein is a further important advantage. According to one embodiment, formamide is used for stabilizing the transcriptome. As described above and shown in the examples, formamide is highly effective in stabilizing the transcriptome as well as the extracellular nucleic acid population. Furthermore, cells can be isolated from the sample thereby allowing the analysis of specific cell populations such as e.g. tumor cells, e.g. circulating tumor cells in blood samples. The advantages and technical effects were described in detail above and it is referred to the above disclosure.

Furthermore, the stabilization reagents and methods, as disclosed in herein, provide an advantage over known state-of-the-art stabilization reagents and methods which involve the use of cross-linking reagents, such as formaldehyde, formaldehyde releasers and the like, as the stabilization of samples according to the present invention does not involve the use to such crosslinking reagents. Crosslinking reagents cause inter- or intra-molecular covalent bonds between nucleic acid molecules or between nucleic acids and proteins. This effect can lead to a reduced recovery of such stabilized and partially crosslinked nucleic acids after a purification or extraction from a complex biological sample. As, for example, the concentration of circulating nucleic acids in a whole blood samples is already relatively low, any measure which further reduces the yield of such nucleic acids should be avoided. This may be of particular importance when detecting and analyzing very rare nucleic acid molecules derived from malignant tumors or from a developing fetus in the first trimester of pregnancy. Therefore, no formaldehyde releaser is comprised in the stabilizing composition, respectively is not additionally used for stabilization. Thus, according to one embodiment, no cross-linking agents such as formaldehyde or formaldehyde releasers are comprised in the stabilizing composition, respectively are not additionally used for stabilization. Thus, here the stabilization composition does not comprise a cross-linking agent that induces nucleic acid-nucleic acid, nucleic-acid-protein, in particular protein DNA and/or protein-protein crosslinks. In particular, the stabilization composition does not comprise formaldehyde, formaline, paraformaldehyde or a formaldehyde releaser. Furthermore, as described, the stabilizing composition does preferably not comprise any additives that would induce the lysis of cells, such as e.g. chaotropic salts. Furthermore, according to one embodiment, the stabilization method according to the invention does not involve the use of additives that classify as toxic agents.

Particularly preferred aspects and embodiments are described again in the following.

In a first aspect, the present invention is in particular directed to a method for stabilizing a cell-containing biological sample by contacting the sample with at least one carboxylic acid amide, wherein the carboxylic acid amide is selected from primary carboxylic acid amides and secondary carboxylic acid amides. Preferably, the resulting composition comprising the cell-containing biological sample and the at least one carboxylic acid amide comprises the carboxylic acid amide in a concentration of at least 0.25%. According to one embodiment, the stabilization results in a stabilization of intracellular RNA and/or wherein the extracellular nucleic acid population comprised in the cell-containing sample is stabilized. As described herein, the method is not based on cell lysis and wherein the stabilization does not involve the use of a cross-linking agent that induces protein-nucleic acid and/or protein-protein crosslinks and does not involve the use of a formaldehyde releaser.

According to one embodiment, the carboxylic acid amide which is selected from primary carboxylic acid amides and secondary carboxylic acid amides has the formula 1

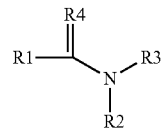

formula 1 wherein R1 is a hydrogen residue or an alkyl residue, wherein R2 is selected from a hydrogen residue and a hydrocarbon residue with a length of the carbon chain of 1-20 atoms arranged in a linear or branched manner, wherein R3 is a hydrogen residue, and wherein R4 is oxygen.

According to one embodiment, the cell-containing sample is contacted with at least one primary carboxylic acid amide which is selected from the group consisting of formamide, acetamide, propanamide and butanamide, preferably butanamide. According to another embodiment, the cell-containing biological sample is contacted with at least one secondary carboxylic acid amide which is selected from the group consisting of N-alkylformamide, N-alkylacetamide and N-alkylpropanamide, and preferably is selected from N-methylformamide, N-methylacetamide and N-methylpropanamide.

According to one embodiment, the method for stabilizing a cell-containing biological sample comprises contacting the sample with at least one carboxylic acid amide, wherein the carboxylic acid amide is formamide and wherein the resulting composition comprising the cell-containing biological sample and formamide comprises formamide in a concentration of at least 0.25% and wherein the stabilization results in a stabilization of intracellular RNA and/or wherein the extracellular nucleic acid population comprised in the cell-containing sample is stabilized and wherein said method is not based on cell lysis and wherein the stabilization does not involve the use of a cross-linking agent that induces protein-nucleic acid and/or protein-protein crosslinks and wherein said method does not involve the use of a formaldehyde releaser.

According to one embodiment, the mixture that is obtained when contacting the cell-containing biological sample with the at least one carboxylic acid amide which is selected from primary carboxylic acid amides and secondary carboxylic acid amides comprises said carboxylic acid amide in a concentration of at least 0.1%, at least 0.25%, at least 0.5%, at least 0.75%, at least 1%, at least 1.25%, at least 1.5% or at least 2%. Suitable concentration ranges were also described above. According to one embodiment, the carboxylic acid amide is formamide.

According to one embodiment, the cell-containing sample is a blood sample and is additionally contacted with an anticoagulant.

According to one embodiment, the degradation of nucleic acids present in the cell-containing sample is reduced due to the stabilization. In particular, intracellular RNA is stabilized. Preferably, the transcriptome and/or transcript levels in cells contained in the sample is stabilized. According to one embodiment, the transcript level of one or more marker genes selected from c-fos, IL-1 beta, IL-8 and p53 is stabilized for at least 24 h, preferably at least 48 h upon stabilization. According to one embodiment, the method is suitable for stabilizing an extracellular nucleic acid population comprised in the cell-containing sample. In particular, the release of genomic DNA from cells contained in the sample into the cell-free portion of the sample is reduced.

According to one embodiment, said method one or more of the following characteristics:
a) the stabilization allows the isolation of cells from the stabilized sample;
b) the cell-containing sample is a blood sample and wherein white blood cells are stabilized;
c) the morphology of cells is preserved;
d) the morphology of nucleated cells is preserved;
e) the sample is a blood sample and contained lymphocytes and/or monocytes are stabilized;
f) cell surface epitopes are preserved; and/or
g) cell surface proteins are preserved.

According to one embodiment, the cell-containing sample is additionally contacted with an apoptosis inhibitor for stabilization. Preferably, the apoptosis inhibitor is a caspase inhibitor, more preferably a pancaspase inhibitor. Suitable caspase inhibitors were described above and it is referred to the above disclosure.

According to one embodiment, the cell-containing sample is additionally contacted with at least one poly(oxyethylene) polymer for stabilization. Preferably, the poly(oxyethylene) polymer is a polyethylene glycol. Details were described above and it is referred to the above disclosure.

According to one embodiment, the method has one or more of the following characteristics:
a) the at least one carboxylic acid amide which is a primary or secondary carboxylic acid amide and optionally further additives are comprised in a stabilising composition and wherein the volumetric ratio of the stabilising composition to the specified volume of the cell-containing sample is selected from 10:1 to 1:20, 5:1 to 1:15, 1:1 to 1:10 and 1:2 to 1:5;
b) the stabilized cell-containing sample is subjected to a nucleic acid analysis and/or detection method;
c) intra- and/or extracellular nucleic acids are isolated from the stabilized sample and the isolated nucleic acids are analyzed and/or detected;
d) cells comprised in the stabilized sample are removed; and/or
e) (i) the stabilized cell-containing biological sample, (ii) the stabilized sample from which cells have been removed and/or (iii) cells removed from the sample are stored.

According to one embodiment, nucleic acids are isolated from the stabilized sample. E.g. RNA can be isolated from cells contained in the stabilized sample. According to one embodiment, cells are removed from the stabilized sample and wherein preferably, removed cells are analyzed and/or wherein biomolecules such as nucleic acids or proteins are isolated from removed cells.

According to one embodiment, the cell-containing sample is additionally contacted with at least one tertiary amide which is a compound according to formula 1

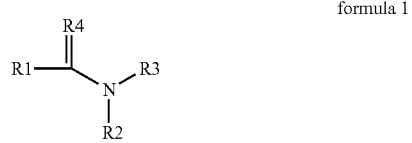

formula 1 wherein R1 is a hydrogen residue or an alkyl residue, wherein R2 and R3 are identical or different hydrocarbon residues with a length of the carbon chain of 1-20 atoms arranged in a linear or branched manner, and wherein R4 is an oxygen, sulphur or selenium residue, preferably R4 is oxygen. The tertiary amide according to formula 1 may be a carboxylic acid amide. It may be a N,N-dialkylpropanamide, preferably N,N-dimethylpropanamide. According to one embodiment, the tertiary amide according to formula 1 is selected from the group consisting of N,N-dimethylformamide, N,N-dimethylacetamide, N,N-dimethylpropanamide, N,N-dimethylbutanamide. According to one embodiment, after the cell-containing biological sample has been contacted with at least one primary or secondary carboxylic acid amide, preferably butanamide, and a tertiary amide according to formula 1 and optionally further additives used for stabilization, the resulting mixture comprises the tertiary amide according to formula 1
i) in a concentration of at least 0.1%, at least 0.25%, at least 0.5%, at least 0.75%, at least 1%, at least 1.25% or at least 1.5%; and/or
ii) in a concentration that lies in the range of 0.1% to 30%, 0.25% to 20%, 0.5% to 15%, 0.7% to 10%, 0.8% to 7.5%, 0.9% to 6% or 1% to 5%.

In a second aspect, the present disclosure pertains to a method for isolating nucleic acids from a biological sample comprising the steps of:
a) stabilizing a cell-containing sample according to the method according to the first aspect;
b) isolating nucleic acids from the stabilized sample.

According to one embodiment, step b) comprises isolating intracellular nucleic acids, preferably intracellular RNA. In particular, step b) may comprise removing cells from the stabilized sample and isolating nucleic acids from the removed cells.

According to one embodiment, step b) comprises isolating extracellular nucleic acids. In particular, cells may be separated from the remaining sample and wherein in step b) extracellular nucleic acids are isolated from the remaining sample and/or intracellular nucleic acids are isolated from the removed cells. Thus, as described above, the method allows to isolate extra- and intracellular nucleic acids in parallel if desired. Preferably, the sample is blood.

According to one embodiment, the isolated nucleic acids are in a further step c) processed and/or analyzed and preferably are:
i) modified;
ii) contacted with at least one enzyme;
iii) amplified;
iv) reverse transcribed;
v) cloned;
vi) sequenced;
vii) contacted with a probe;
viii) detected;
ix) quantified;
ix) identified; and/or
x) analysed for gene expression profiling.

According to a third aspect, a composition suitable for stabilizing a cell-containing biological sample is provided, comprising
a) at least one carboxylic acid amide preferably in a concentration of at least 1%, wherein the carboxylic acid amide is selected from primary carboxylic acid amides and secondary carboxylic acid amides; and
b) at least one anticoagulant.

Suitable and preferred embodiments for the at least one carboxylic acid amide were described above. According to one embodiment, the composition comprises at least one primary carboxylic acid amide which is selected from the group consisting of formamide, acetamide, propanamide and butanamide. Preferably, the primary carboxylic acid amide is selected from formamide and butanamide. According to another embodiment, the composition comprises at least one secondary carboxylic acid amide which is selected from the group consisting of N-alkylformamide, N-alkylacetamide and N-alkylpropanamide, and preferably is selected from N-methylformamide, N-methylacetamide and N-methylpropanamide. According to one embodiment, the anticoagulant is a chelating agent, preferably EDTA.

According to one embodiment, the composition comprises at least one poly(oxyethylene) polymer for stabilization. Preferably, the poly(oxyethylene) polymer is a polyethylene glycol. Details were described above and it is referred to the above disclosure.

According to one embodiment, the composition is for stabilizing a blood sample as cell-containing sample.

According to one embodiment, the composition comprises at least one tertiary amide according to formula 1 as described above in conjunction with the first aspect. Such tertiary amide can be e.g. used in combination with butanamide.

According to one embodiment, the composition comprises at least one apoptosis inhibitor, preferably a caspase inhibitor, more preferred a pancaspase inhibitor, wherein preferably, the pancaspase inhibitor is selected from the group consisting of Q-VD-OPh and Z-Val-Ala-Asp(OMe)-FMK, and the caspase inhibitor preferably is Q-VD-OPh.

According to one embodiment, the composition additionally comprises at least one poly(oxyethylene) polymer, preferably polyethylene glycol and an apoptosis inhibitor, preferably a caspase inhibitor.

According to one embodiment, the composition is capable of stabilizing the gene transcription profile of contained cells and/or is capable of stabilizing an extracellular nucleic acid population comprised in a cell-containing sample. According to one embodiment, the composition has one or more of the following characteristics:
  a) it is capable of stabilizing cells and reducing the release of genomic DNA from cells contained in the cell-containing biological sample into the cell-free portion of the sample;
  b) it is capable of reducing the dilution of the extracellular DNA population comprised in the biological sample with genomic DNA originating from cells contained in the stabilized sample;
  c) it is capable of reducing the dilution of the extracellular nucleic acid population comprised in the biological sample with intracellular nucleic acids originating from cells contained in the stabilized sample;
  d) the stabilization composition does not comprise additives in a concentration wherein said additives would induce or promote cell lysis;
  e) the stabilization composition does not comprise a cross-linking agent that induces protein-DNA and/or protein-protein crosslinks;
  f) the stabilization composition does not comprise formaldehyde, formaline, paraformaldehyde or a formaldehyde releaser;
  g) the stabilization composition does not comprise a toxic agent and/or
  h) the stabilization composition is capable of stabilizing extracellular nucleic acid population comprised in the cell-containing biological sample without refrigeration, preferably at room temperature, for a time period selected from at least two days, at least three days, at least two days to three days, at least two days to six days and/or at least two days to seven days.

According to one embodiment, upon contact of the stabilizing composition with a blood sample the transcript level of one or more marker genes selected from c-fos, IL-1beta, IL-8 and p53 is stabilized for at least 48 h upon stabilization, and wherein, preferably, the volumetric ratio of the stabilizing composition to the cell-containing sample is selected from 10:1 to 1:20, 5:1 to 1:15, 1:1 to 1:10 and 1:2 to 1:5. According to one embodiment, the sample is a blood sample and wherein the morphology of and/or cell surface epitopes on white blood cells, preferably lymphocytes, is preserved.

According to one embodiment, the stabilizing composition is provided as mixture with a biological sample. According to one embodiment, the stabilizing composition is provided as mixture with a biological sample and wherein said sample has one or more of the following characteristics:
  a) it comprises extracellular nucleic acids;
  b) it is whole blood.

The present invention also pertains to the use of a composition according to the third aspect in a stabilization method according to the first aspect.

According to a fourth aspect, a container for collecting a cell-containing biological sample, preferably a blood sample, is provided which comprises
  a) at least one carboxylic acid amide in a concentration of at least 1%, wherein the carboxylic acid amide is selected from primary carboxylic acid amides and secondary carboxylic acid amides; and
  b) at least one anticoagulant.

According to one embodiment, the container comprises at least one primary carboxylic acid amide which is selected from the group consisting of formamide, acetamide, propanamide and butanamide. Preferably, the primary carboxylic acid amide is selected from formamide and butanamide. According to another embodiment, the container comprises at least one secondary carboxylic acid amide which is selected from the group consisting of N-alkylformamide, N-alkylacetamide and N-alkylpropanamide, and preferably is selected from N-methylformamide, N-methylacetamide and N-methylpropanamide. According to one embodiment, the anticoagulant is a chelating agent, preferably EDTA.

According to one embodiment, the container additionally comprises at least one poly(oxyethylene) polymer for stabilization. Preferably, the poly(oxyethylene) polymer is a polyethylene glycol. Details were described above and it is referred to the above disclosure.

As described, the container may comprise a composition according to the third aspect of the present invention. Therefore, according to one embodiment, the aforementioned compounds may be comprised in a composition.

According to a fifth aspect, a method is provided comprising the step of collecting, preferably withdrawing, a biological sample, preferably blood, from a patient directly into a chamber of a container according to the fourth aspect of the present invention.

According to a sixth aspect, a method of producing a composition according to the third aspect of the present invention is provided, wherein the components of the composition are mixed, preferably are mixed in a solution.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The term "solution" as used herein in particular refers to a liquid composition, preferably an aqueous composition. It may be a homogenous mixture of only one phase but it is also within the scope of the present invention that a solution comprises solid additives such as e.g. precipitates, in particular of contained chemicals such as stabilizing agents.

The sizes, respectively size ranges indicated herein with reference to nucleotides (nt), refer to the chain length and thus are used in order to describe the length of single-stranded as well as double-stranded molecules. In double-stranded molecules said nucleotides are paired.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

TABLE 1

Overview of apoptosis inhibitors

| Apoptosis inhibitor | Description |
| --- | --- |
| 1. Metabolic inhibitors | |
| AICA-Riboside, Acadesine, AICAr, 5-Aminoinnidazole-4-carboxamide-1-β-riboside, Z-Riboside | Offers protection against cell death induced by glucose deprivation |
| Apoptosis Inhibitor II, diarylurea compound | prevents the active ~700-kDa apoptosome complex formation |
| Bax Channel Blocker, (±)-1-(3,6-Dibromocarbazol-9-yl)-3-piperazin-1-yl-propan-2-ol, bis TFA, iMAC1 | A cell-permeable dibromocarbazolo-piperaziny derivative that displays anti-apoptotic properties. Effectively blocks Bid-induced cyctochrome c release from HeLa cell mitochondria (~80% inhibition at 5 µM) by inhibiting Bax channel-forming activity (IC50 = 520 nM in a liposome channel assay). |
| Bax-Inhibiting Peptide, V5 Peptide sequence: H-Val-Pro-Met-Leu-Lys-OH | A cell-permeable pentapeptide based on the Ku70-Bax inhibiting domain that offers cytoprotection. Functions as effectively as the Caspase Inhibitor VI (Z-VAD-FMK; Cat. No. 219007) for Bax-mediated apoptosis (~50-200 µM). Also effectively blocks caspase-independent necrotic cell death. Shown to be Ku70 competitive, interact with Bax, prevent its conformational change and mitochondrial translocation. Displays extended stability in culture medium (~3 days). |
| Bcl-xL BH44-23, Human, Cell-Permeable | A cell-permeable peptide that prevents apoptotic cell death by directly binding to the voltage-dependent anion channel (VDAC) and blocking its activity. Leads to the inhibition of cytochrome c release and loss of mitochondrial membrane potential (ΔΨm). Contains the conserved N-terminal homology domain (BH4) of Bcl-xL (amino acids 4-23) that has been shown to be essential for inhibiting VDAC activity in liposomes and in isolated mitochondria. The BH4 domain is linked to a carrier peptide, a 10-amino acid HIV-TAT48-57 sequence with a β-alanine residue as a spacer for maximum flexibility. Following its uptake, it is mainly localized to the mitochondria |
| Bongkrekic Acid, Triammonium Salt | Acts as a ligand of the adenine nucleotide translocator. A potent inhibitor of mitochondrial megachannel (permeability transition pore). Significantly reduces signs of apoptosis induced by nitric oxide. Prevents the apoptotic breakdown of the inner mitochondrial transmembrane potential (ΔΨm), as well as a number of other phenomena linked to apoptosis |
| Daunorubicin, Hydrochloride | Potent cell-permeable anticancer agent whose potential target site may be mitochondrial cytochrome c oxidase. Has been shown to inhibit RNA and DNA synthesis. Inhibits eukaryotic topoisomerases I and II. Induces DNA single-strand breaks. Also induces apoptosis in HeLa S3 tumor cells. According to one embodiment, said compound is not used as stabilizer according to the present invention. |
| Humanin, Human, Synthetic | A 24-residue anti-apoptotic peptide that, when expressed intracellularly, offers protection against neuronal apoptosis induced by presenilin and APP (amyloid precursor protein) mutants associated with familial Alzheimer's disease (AD). Shown to reduce cytochrome c release in vitro by directly binding to Bax (Bcl-2-associated X protein; Kd~2 nM) and preventing its association with isolated mitochondria |
| Phorbol-12-myristate-13-acetate | Most commonly-used phorbol ester. Activates protein kinase C in vivo and in vitro, even at nM concentrations. Activates Ca2+-ATPase and potentiates forskolin-induced cAMP formation. Inhibits apoptosis induced by the Fas antigen, but induces apoptosis in HL-60 promyelocytic leukemia cells. |

TABLE 1-continued

Overview of apoptosis inhibitors

| Apoptosis inhibitor | Description |
| --- | --- |
| Pifithrin-α | A cell-permeable chemical inhibitor of p53. Reversibly inhibits p53-dependent transactivation of p53-responsive genes and reversibly blocks p53-mediated apoptosis. Inhibits p53-dependent growth arrest of human diploid fibroblasts in response to DNA damage but has no effect on p53-deficient fibroblasts. Protects normal tissues from the deleterious side effects of chemotherapy. Has been reported to protect neurons against β-amyloid peptide and glutamate-induced apoptosis |
| Pifithrin-μ | A cell-permeable sulfonamide that blocks p53 interaction with Bcl-xL and Bcl-2 proteins and selectively inhibits p53 translocation to mitochondria without affecting the transactivation function of p53. Effectively protects against γ radiation-induced cell death in vitro and animal lethality in vivo. Because Pifithrin-μ targets only the mitochondrial branch of the p53 pathway without affecting the important transcriptional functions of p53, it is superior to Pifithrin-α in in vivo studies. Shown to selectively interact with inducible HSP70 and disrupt its functions |
| Pifithrin-α, Cyclic- | A cell-permeable and very stable analog of Pifithrin-α, with similar biological function, but with reduced cytotoxicity. A chemical inhibitor of p53. Reversibly inhibits p53-dependent transactivation of p53-responsive genes; also reversibly blocks p53-mediated apoptosis. Acts as a P-gp modulator by changing relative substrate specificity of the transporter. This compound has been reported to be a potent STAT6 transcriptional inhibitor |
| Pifithrin-α, p-Nitro | A cell-permeable p53 inhibitor that serves as the prodrug form of Pifithrin-α, p-Nitro, Cyclic. Although its in vitro efficacy (ED50 = 0.3 μM in protecting etoposide-induced cortical neuron death) is similar to that of Pifithrin-α, it is 100-fold more potent than Pifithrin-α when administered in rats in vivo due to its long-lasting, steady conversion to the corresponding cyclic form of active compound in biological systems (t1/2 = 8h in neuron culture medium at 37° C.). |
| Pifithrin-α, p-Nitro, Cyclic | A cell-permeable p53 inhibitor that exhibits 10-fold higher potency (ED50 = 30 nM in protecting etoposide-induced cortical neuron death) and 50% longer half-life (t1/2 = 6h in neuron culture medium at 37° C.) than Pifithrin-α. It shows in vitro efficacy. |
| STAT3 Inhibitor Peptide<br>Peptide sequence:<br>Ac-Pro-Tyr(PO3H2)-Leu-Lys-Thr-Lys-OH | A Stat3-SH2 domain binding phosphopeptide that acts as a selective inhibitor of Stat3 (signal transducers and activators of transcription 3) signaling with a DB50 of 235 μM (concentration of peptide at which DNA-binding activity is inhibited by 50%). Significantly lowers the DNA-binding activity of Stat3 by forming an inactive Stat3:peptide complex and reduces the levels of active Stat3:Stat3 dimers that can bind DNA. Displays greater affinity for Stat3, and to a lesser extent Stat1, over Stat5. Supplied as a trifluoroacetate salt. |
| STAT3 Inhibitor Peptide, Cell-Permeable<br>Peptide sequence:<br>Ac-Pro-Tyr(PO3H2)-Leu-Lys-Thr-Lys-OH | A cell-permeable analog of the Stat3-SH2 domain-binding phosphopeptide that contains a C-terminal mts (membrane translocating sequence) and acts as a highly selective, potent blocker of Stat3 activation. Also suppresses constitutive Stat-3 dependent Src transformation with no effect on Stat-3 independent Ras transformation. The unphosphorylated inactive control peptide is also available. Supplied as a trifluoroacetate salt. |
| CAY10500, 6,7-dimethyl-3-{[methyl-[1-(3-trifluoromethyl-phenyl)-1H-indol-3-ylmethyl]-amino}-ethyl)-amino]-methyl}-chromen-4-one | Tumor necrosis factor α (TNFα) inhibitor that prevents binding to the TNF Receptor 1 (TNFR1). 6 Binds to the biologically active TNFα trimer and promotes accelerated displacement of a single subunit to rapidly inactivate the cytokine. In a cell based assay, compound inhibited TNFα-mediated stimulation of IKB degradation. |
| Gambogic amide | A selective agonist for TrkA which mimics the actions of NGF. This compound possesses robust neurotrophic actvity, while it prevents neuronal cell death 1. |
| Maslinic Acid | A pentacyclic triterpene with antioxidant and anti-inflammatory properties. Shown to block the generation of nitric oxide, and inhibits the secretion of IL-6 and TNF-α induced by lipopolysaccharides |
| Naringin hydrate | A citrus bioflavonoid found to inhibit cytochrome P450 monooxygenase activity in mouse liver. It prevents toxin-induced cytoskeletal disruption and apoptotic liver cell death. |
| Necrostatin-1 | An inhibitor of necroptosis, a non-apoptotic cell death pathway. Does not affect Fas/TNFR-triggered apoptosis. According to one embodiment, said compound is not used as stabilizer according to the present invention. |

TABLE 1-continued

Overview of apoptosis inhibitors

| Apoptosis inhibitor | Description |
| --- | --- |
| NSC348884 hydrate, N1,N2-bis((3-imino-6-methyl-3H-indol-2-yl)methyl)-N1,N2-bis((6-methyl-1H-benzo[d]imidazol-2-yl)methyl)ethane-1,2-diamine hydrate | This product is a nucleolar phosphoprotein that displays several biological activities in ribosome biogenesis, cell proliferation, cytoplasmic/nuclear shuttle transportation, nucleic acid binding, ribonucleic cleavage, centrosome duplication and molecular chaperoning, and is found in higher levels in tumor cells. Overexpression has been shown to lead to inhibition of apoptosis. NSC34884 upregulates p53. |
| Orsellinic acid | Benzoic acid. Blocks PAF-mediated neuronal apoptosis. Shows free radical scavenging activity. |
| tetramethyl Nordihydroguaiaretic Acid | A synthetic derivative of NDGA and a non-selective lipoxygenase inhibitor. It inhibits Sp1 transcription factor binding at the HIV long terminal repeat promoter and at the α-ICP4 promoter (a gene essential for HSV replication). |
| GW 4869, 3,3'-(1,4-phenylene)bis[N-[4-(4,5-dihydro-1H-imidazol-2-yl)phenyl]-hydrochloride-2-propenamide | A cell-permeable, symmetrical dihydroimidazolo-amide compound that acts as a potent, specific, non-competitive inhibitor of N-SMase (neutral sphingomyelinase) [IC50 = ~1 μM, rat brain; Km for sphingomyelin ~13 μM]. Does not inhibit human A-SMase (acid sphingomyelinase) even at 150 μM. Weakly inhibits the activities of bovine protein phosphatase 2A and mammalian lyso-PAF PLC, while no inhibition is observed for bacterial phosphatidylcholine-specific PLC. Reported to offer complete protection against TNF-α or diamine-induced cell death in MCF7 breast cancer cells at 20 μM. Does not modify the intracellular glutathione levels or interfere with TNF-α or diamine-mediated signaling effects. |
| SP 600125, 1,9-Pyrazoloanthrone, Anthrapyrazolone | SP600125 is a JNK inhibitor (IC50 = 40 nM for JNK-1 and JNK-2 and 90 nM for JNK-3). This agent exhibits greater than 300-fold selectivity for JNK against related MAP kinases ERK1 and p38-2, and the serine threonine kinase PKA. SP600125 is a reversible ATP-competitive inhibitor. |
| Mdivi-1, 3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone | Mdivi-1 is a selective inhibitor of mitochondrial division in yeast and mammalian cells which acts via inhibiting the mitochondrial division dynamin. In cells, Mdivi-1 inhibits apoptosis by inhibiting mitochondrial outer membrane permeabilization. |
| Minocycline. hydrochloride | Tetracycline derivative with antimicrobial activity. Inhibitor of angiogenesis, apoptosis and poly(ADP-ribose) polymerase-1 (PARP-1). Anti-inflammatory and neuroprotective |
| Ro 08-2750 (C13H10N4O3) | Inhibitor of NGF-induced apoptosis. |
| RKTS-33 (C7H8O4) | selective inhibition of Fas ligand-dependent pathway alone |
| 2. Nucleic acids | |
| 3,4-Dichloroisocoumarin | Inhibitor of serine proteases –> granzyme B and blocks apoptotic internucleosomal DNA cleavage in thymocytes without the involvement of endonucleases. Does not affect thiol proteases and metalloproteases |
| Actinomycin D, Streptomyces sp. | Also acts as a competitive inhibitor of serine proteases; Classical anti-neoplastic drug. Cytotoxic inducer of apoptosis against tumor cells. A DNA dependent inhibitor of RNA synthesis, actinomycin promotes induction of apoptosis by some specific stimuli, for example, TRAIL and Fas (CD95). Actinomycin D can also alleviate or block the apoptotic process and decrease the cytotoxicity induced by several stimuli such as the dihydrofolate reductase inhibitor aminopterin and the prostaglandin derivative 15-deoxy-D12,14-prostaglandin J2, thus it can have both pro and anti-apoptotic activities in some systems. According to one embodiment, said compound is not used as stabilizer according to the present invention. |
| Aurintricarboxylic Acid | Inhibitor of DNA topoisomerase II |
| Baicalein | A cell-permeable flavone that inhibits the activity of 12-lipoxygenase (IC50 = 120 nM) and reverse transcriptase. Protects cortical neurons from β-amyloid induced toxicity. Reduces leukotriene biosynthesis and inhibits the release of lysosomal enzymes. Also inhibits cellular Ca2+ uptake and mobilization, and adjuvant-induced arthritis. Reported to inhibit microsomal lipid peroxidation by forming an iron-baicalein complex. Inhibits topoisomerase II and induces cell death in hepatocellular carcinoma cell lines. Potentiates contractile responses to nerve stimulation. Inhibits protein tyrosine kinase and PMA-stimulated protein kinase C |
| Camptothecin, Camptotheca acuminata | A cell-permeable DNA topoisomerase I inhibitor. Exhibits anti-leukemic and antitumor properties. Induces apoptosis in HL-60 cells and mouse thymocytes. Arrests cells at the G2/M phase. According to one embodiment, said compound is not used. |

TABLE 1-continued

Overview of apoptosis inhibitors

| Apoptosis inhibitor | Description |
| --- | --- |
| Diisopropylfluorophosphate | serine protease inhibitor |
| Phenylmethylsulfonyl Fluoride (PMSF) | Irreversible inhibitor of serine proteases. Its mechanism of action is analogous to that of diisopropylfluorophosphate. PMSF causes sulfonylation of the active-site serine residues. Alsoreported to inhibit internucleosomal DNA fragmentation in immature thymocytes. For a related, more stable inhibitor, see AEBSF |
| (-)-Huperzine A | An inhibitor of AChE. Antagonist of NMDA receptors. Protects against glutamate-mediated excitotoxicity. |
| Razoxane | Inhibits topoisomerase II without inducing DNA strand breaks (topo II catalytic inhibitor). |
| Suptopin-2 | Suppressor of topoisomerase II inhibition. Reverses cell cycle arrest; bypass of checkpoint function. Has inherent fluorescence and a distinct advantage in identification of molecule targets; effective concentraion in the μM range. |
| 3. Enzymes | |
| 3.1. Caspases | |
| Apoptosis Inhibitor; 2-(p-Methoxybenzyl)-3,4-pyrrolidinediol-3-acetate | Effects attributable to the inhibition of caspase-3 activation |
| cIAP-1, Human, Recombinant, E. coli | Recombinant, human cIAP-1 (amino acids 1-618) fused to the peptide sequence MATVIDH10SSNG at the N-terminus and expressed in E. coli. cIAP is a member of the inhibitor of apoptosis family of proteins that inhibits proteolytic activity of mature caspases by interaction of the BIR domain with the active caspase |
| CrmA, Recombinant | CrmA (cowpox viral serpin cytokine response modifier A) is purified from E. coli transformed with a construct containing the full-length coding region of the CrmA gene and 7 additional amino acids that do not affect the activity. CrmA is a natural inhibitor of human caspase-1 and granzyme B, enzymes that are involved in apoptosis |
| Group III Caspase Inhibitor I Peptide sequence: Ac-Ile-Glu-Pro-Asp-CHO, IEPD-CHO, Caspase-8 inhibitor III | A potent, cell-permeable, and irreversible inhibitor of Group III caspases (caspase-6, -8, -9, and -10), although more effective towards caspases-6 and -8. Also inhibits caspase-1 and caspase-Ac- 3. When using with purified native or recombinant enzyme, pretreatment with an esterase is required. |
| Kaempferol | A cell-permeable phytoestrogen that inhibits topoisomerase I-catalyzed DNA religation in HL-60 cells. Offers protection against Aβ25-35-induced cell death in neonatal cortical neurons. Its protective effects are comparablet o that of estradiol. Blocks the Aβ-induced activation of caspase-2, -3, -8, and -9, and reduces NMDA-induced neuronal apoptosis. Reported to be a potent inhibitor of monoamine oxidases. Acts as an inhibitor of COX-1 activity (IC50 = 180 μM), and of transcriptional activation of COX-2 (IC50 < 15 μM |
| Q-VD-OPH | General, Pancaspase |
| Boc-D(OMe)-FMK | General, Pancaspase |
| Z-D(OMe)E(OMe)VD(OMe)-FMK | Caspase 3, 7 |
| Z-LE(OMe)TD(OMe)-FMK | Caspase 8 |
| Z-YVAD(OMe)-FMK | Caspase 1, 4 |
| Z-FA-FMK | Inhibits Cathepsin B |
| Z-FF-FMK | Cathepsin B, L |
| Mu-PheHphe-FMK | Cathepsin B, L |
| Z-AE(OMe)VD(OMe)-FMK | Caspase 10 |
| Z-ATAD(OMe)-FMK | Caspase 12 |
| Z-VK(Biotin)-D(OMe)-FMK | General Caspase |
| Z-LE(OMe)VD(OMe)-FMK | Caspase 4 |
| Z-VAM-FMK | Antiviral peptide inhibitor, Inhibits HRV2 and HRV14 |
| 4'-Azidocytidine | HCV Inhibitor |
| Caspase-13 Inhibitor I Peptide sequence: Ac-Leu-Glu-Glu-Asp-CHO | A potent, reversible inhibitor of caspase-13 (ERICE). |
| Caspase-13 Inhibitor II Peptide sequence: Z-Leu-Glu(OMe)-Glu(OMe)-Asp(OMe)-FMK | A cell-permeable, irreversible inhibitor of caspase-13. When using with purified native or recombinant enzyme, pretreatment with an esterase is required. |
| Caspase-1 Inhibitor I Peptide sequence: Ac-Tyr-Val-Ala-Asp-CHO | A potent, specific, and reversible inhibitor of caspase-1 (Ki = 200 pM for human recombinant caspase-1), caspase-4, and caspase-5. Strongly inhibits anti-APO-1 induced apoptosis in L929-APO-1 cells. |
| Caspase-1 Inhibitor I, Cell-Permeable Peptide sequence: Ac-Ala-Ala-Val-Ala-Leu-Leu-Pro-Ala-Val-Leu-Leu-Ala-Leu- | A cell-permeable inhibitor of caspase-1 (ICE; Interleukin-1β Converting Enzyme), caspase-4, and caspase-5. The C-terminal YVAD-CHO sequence of this peptide is a highly specific, potent, and reversible inhibitor of caspase-1 (Ki = 1 nM). The N-terminal sequence (amino acid residues 1-16) corresponds to the |

TABLE 1-continued

Overview of apoptosis inhibitors

| Apoptosis inhibitor | Description |
|---|---|
| Leu-Ala-Pro-Tyr-Val-Ala-Asp-CHO | hydrophobic region (h-region) of the signal peptide of the Kaposi fibroblast growth factor (K-FGF) and confers cell-permeability to the peptide |
| Caspase-1 Inhibitor II<br>Peptide sequence:<br>Ac-Tyr-Val-Ala-Asp-CMK | A cell-permeable and irreversible inhibitor of caspase-1 (Ki = 760 pM), caspase-4, and caspase-5. Inhibits Fas-mediated apoptosis and acidic sphingomyelinase activation |
| Caspase-1 Inhibitor IV<br>Peptide sequence:<br>Ac-Tyr-Val-Ala-Asp-AOM =<br>2,6-dimethylbenzoyloxymethyl ketone) | A highly selective, competitive, cell-permeable, and irreversible inhibitor of caspase-1, caspase-4, and caspase-5. Inactivates the enzyme with a rate limited by diffusion and is relatively inert toward (AOM other bionucleophiles such as glutathione, making it an excellent candidate for in vivo studies of enzyme inhibition |
| Caspase-1 Inhibitor V<br>Peptide sequence:<br>Z-Asp-CH2-DCB | A potent inhibitor of caspase-1-like proteases. Blocks apoptotic cell death in human myeloid leukemia U937 cells and blocks etoposide-induced DNA fragmentation |
| Caspase-1 Inhibitor VI<br>Peptide sequence:<br>Z-Tyr-Val-Ala-Asp(OMe)-CH2F* | A potent, cell-permeable, and irreversible inhibitor of caspase-1 c(ICE), caspase-4, and caspase-5 |
| Caspase-2 Inhibitor I<br>Peptide sequence:<br>Z-Val-Asp(OMe)-Val-Ala-Asp(OMe)-CH2F* | A cell-permeable and irreversible inhibitor of caspase-2 (ICH-1 |
| Caspase-2 Inhibitor II<br>Peptide sequence:<br>Ac-Leu-Asp-Glu-Ser-Asp-CHO | A reversible inhibitor of caspase-2 and caspase-3 |
| Caspase-3/7 Inhibitor I<br>Peptide sequence:<br>5-[(S)-(+)-2-(Methoxymethyppyrrolidino] sulfonylisatin | A potent, cell-permeable, and specific, reversible inhibitor of caspase-3 (Ki = 60 nM) and caspase-7 (Ki = 170 nM). |
| Caspase-3 Inhibitor I<br>Peptide sequence:<br>Ac-Asp-Glu-Val-Asp-CHO | A very potent, specific, and reversible inhibitor of caspase-3 (IC50 = 200 pM), caspase-6, caspase-7, caspase-8, and caspase-10. |
| Caspase-3 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Asp-Glu-Val-Asp-CHO | A cell-permeable inhibitor of caspase-3, as well as caspase-6, caspase-7, caspase-8, and caspase-10. The C-terminal DEVD-CHO sequence of this peptide is a highly specific, potent, and reversible inhibitor of caspase-3 (Ki < 1 nM) that has also been shown to strongly inhibit PARP cleavage in cultured human osteosarcoma cell extracts (IC50 = 200 pM). The N-terminal sequence (amino acid residues 1-16) corresponds to the hydrophobic region (h-region) of the signal peptide of Kaposi fibroblast growth factor (K-FGF) and confers cell-permeability to the peptide. A 5 mM (1 mg/100 µl) solution of Caspase-3 Inhibitor I, Cell-permeable (Cat. No. 235427) in DMSO is also available. |
| Caspase-3 Inhibitor II<br>Peptide sequence:<br>Z-Asp(OCH3)-Glu(OCH3)-Val-Asp(OCH3)-FMK | A potent, cell-permeable, and irreversible inhibitor of caspase-3 as well as caspase-6, caspase-7, caspase-8, and caspase-10. When using with purified native or recombinant enzyme, pretreatment with an esterase is required. A 5 mM (250 µg/75 µl) solution of Z-DEVD-FMK (Cat. No. 264156) in DMSO is also available |
| Caspase-3 Inhibitor III<br>Peptide sequence:<br>Ac-Asp-Glu-Val-Asp-CMK | A potent, cell-permeable, and irreversible inhibitor of caspase-3 as well as caspase-6, caspase-7, caspase-8, and caspase-10 |
| Caspase-3 Inhibitor IV<br>Peptide sequence.<br>Ac-Asp-Met-Gln-Asp-CHO | A specific inhibitor of caspase-3. This tetrapeptide inhibitor has been used with the caspase-6 inhibitor Ac-VEID-CHO to dissect the pathway of caspase activation in Fas-stimulated Jurkat cells |
| Caspase-3 Inhibitor V<br>Peptide sequence:<br>Z-Asp(OMe)-Gln-Met-Asp(OMe)-CH2F* | A potent, cell-permeable, and irreversible inhibitor of caspase-3, also recognizes caspase-1. When using with purified native or recombinant enzyme, pre-treatment with an esterase is required |
| Caspase-3 Inhibitor VII<br>Peptide sequence:<br>2-(4-Methyl-8-(morpholin-4-ylsulfonyl)-1,3-dioxo-1,3-dihydro-2H-pyrrolo[3,4-c]quinolin-2-yl)ethyl acetate | A cell-permeable, non-peptidyl pyrroloquinoline compound that acts as a potent, reversible, and non-competitive inhibitor of caspase-3 (IC50 = 23 nM) with 10-100-fold greater selectivity. Shown to display higher anti-apoptotic activity than Z-VAD-FMK (Cat. No. 627610) in a model of Staurosporine- (Cat. No. 569397) induced apoptosis in human Jurkat T cells. |
| Caspase-4 Inhibitor I<br>Peptide sequence:<br>Ac-Leu-Glu-Val-Asp-CHO | A reversible caspase-4 inhibitor |
| Caspase-4 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Leu-Glu-Val-Asp-CHO | A potent, cell-permeable, and reversible inhibitor of caspase-4. The N-terminal sequence (amino acid residues 1-16) corresponds to the hydrophobic region of the signal peptide of Kaposi fibroblast growth factor and confers cell permeability to the peptide. |

TABLE 1-continued

Overview of apoptosis inhibitors

| Apoptosis inhibitor | Description |
| --- | --- |
| Caspase-5 Inhibitor I<br>Peptide sequence:<br>Z-Trp-Glu(OMe)-His-Asp(OMe)-CH2F* | A potent, cell-permeable, and irreversible inhibitor of caspase-5. Strongly inhibits caspase-1. Also inhibits caspase-4 and caspase-8 |
| Caspase-6 Inhibitor I<br>Peptide sequence:<br>Z-Val-Glu(OMe)-Ile-Asp(OMe)-CH2F* | A cell-permeable, irreversible inhibitor of caspase-6. When using with purified native or recombinant enzyme, pretreatment with an esterase is required |
| Caspase-6 Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Val-Glu-Ile-Asp-CHO | A potent, cell-permeable, and reversible inhibitor of caspase-6. The N-terminal sequence (amino acids 1-16) corresponds to the hydrophobic region of the signal peptide of Kaposi fibroblast growth factor and confers cell permeability to the peptide |
| Caspase-8 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Ile-Glu-Thr-Asp-CHO | A potent, cell-permeable, and reversible inhibitor of caspase-8 and Granzyme B. The N-terminal sequence (amino acids 1-16) corresponds to the hydrophobic region of the signal peptide of Kaposi fibroblast growth factor and confers cell permeability to the peptide |
| Caspase-8 Inhibitor II<br>Peptide sequence:<br>Z-Ile-Glu(OMe)-Thr-Asp(OMe)-CH2F* | A potent, cell-permeable, and irreversible inhibitor of caspase-8 and granzyme B. Effectively inhibits influenza virus-induced apoptosis in HeLa cells. Also inhibits granzyme B. When using with purified native or recombinant enzyme, pretreatment with an esterase is required. A 5 mM (250 µg/76 µl) solution of Z-IETD-FMK (Cat. No. 218840) in DMSO is also available. |
| Caspase-9 Inhibitor I<br>Peptide sequence:<br>Z-Leu-Glu(OMe)-His-Asp(OMe)-CH2F* | A potent, cell-permeable, and irreversible inhibitor of caspase-9. May also inhibit caspase-4 and caspase-5. When using with purified native or recombinant enzyme, pretreatment with an esterase is required. A 5 mM (250 µg/72 µl) solution of Z-LEHD-FMK (Cat. No. 218841) in DMSO is also available |
| Caspase-9 Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Leu-Glu-His-Asp-CHO | A potent, cell-permeable, and reversible inhibitor of caspase-9. May also inhibit caspase-4 and caspase-5. The N-terminal sequence (amino acids 1-16) corresponds to the hydrophobic region of the signal peptide of Kaposi fibroblast growth factor and confers cell permeability to the peptide |
| Caspase-9 Inhibitor III<br>Peptide sequence:<br>Ac-Leu-Glu-His-Asp-CMK | A potent, irreversible inhibitor of caspase-9. Reported to reduce myocardial infarct size during reperfusion (~70 nM). |
| Caspase Inhibitor I<br>Peptide sequence:<br>Z-Val-Ala-Asp(OMe)-CH2F* | A cell-permeable, irreversible, pan-caspase inhibitor. Inhibits Fas-mediated apoptosis in Jurkat cells and staurosporine-induced cell death in corneal epithelial cells. When using with purified native or recombinant enzyme, pre-treatment with an esterase is required. |
| Caspase Inhibitor II<br>Peptide sequence:<br>Ac-Val-Ala-Asp-CHO | A potent and reversible pan-caspase inhibitor. |
| Caspase Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Val-Ala-Asp-CHO | A cell-permeable, reversible pan-caspase inhibitor produced by attaching the N-terminal sequence (amino acids 1-16) of the Kaposi fibroblast growth factor signaling peptide, which imparts cell-permeability to VAD peptide. |
| Caspase Inhibitor III<br>Peptide sequence:<br>Boc-Asp(OMe)-CH2F* | A cell-permeable, irreversible, broad-spectrum caspase inhibitor. |
| Caspase Inhibitor IV<br>Peptide sequence:<br>Boc-Asp(OBzl)-CMK | A general, irreversible caspase inhibitor. |
| Caspase Inhibitor VI<br>Peptide sequence:<br>Z-Val-Ala-Asp-CH2F* | An irreversible general caspase inhibitor. Useful for studies involving recombinant, isolated, and purified caspase enzymes. Unlike Caspase Inhibitor I (Cat. No. 627610), this inhibitor does not require pretreatment with esterase for in vitro studies. A 10 mM (1 mg/221 µl) solution of Caspase Inhibitor VI (Cat. No. 219011) in DMSO is also available |
| Caspase Inhibitor VIII<br>Peptide sequence:<br>Ac-Val-Asp-Val-Ala-Asp-CHO | A potent, reversible inhibitor of caspase-2 ($K_i$ =3.5 nM), caspase-3 ($K_i$ = 1 nM) and caspase-7 ($K_i$ = 7.5 nM). Also serves as an inhibitor of DRONC (Drosophila caspase), a glutamate/aspartate protease. |
| Caspase Inhibitor X<br>Peptide sequence:<br>BI-9B12 | A benzodioxane containing 2,4-disubstituted thiazolo compound that acts as a selective, reversible and competitive inhibitor of caspases ($K_i$ = 4.3 µM, 6.2 µM and 2.7 µM for caspase-3, -7 and -8, respectively). The benzodioxane moiety is shown to fit in the |

TABLE 1-continued

Overview of apoptosis inhibitors

| Apoptosis inhibitor | Description |
| --- | --- |
| Caspase-1 Inhibitors | 'aspartate hole' of the caspases and possibly disrupt caspase-8 assisted cleavage of BID, a proapoptotic protein. Weakly affects the activity of anthrax lethal factor, a metalloprotease, at ~20 μM Including, but not limited to<br>Ac-N-Me-Tyr-Val-Ala-Asp-aldehyde (pseudo acid)<br>Ac-Trp-Glu-His-Asp-aldehyde (pseudo acid)<br>Ac-Tyr-Val-Ala-Asp-aldehyde (pseudo acid)<br>Ac-Tyr-Val-Ala-Asp-chloromethylketone<br>Ac-Tyr-Val-Ala-Asp-2,6-dimethylbenzoyloxymethylketone<br>Ac-Tyr-Val-Ala-Asp(OtBu)-aldehyde-dimethylacetal<br>Ac-Tyr-Val-Lys-Asp-aldehyde(pseudo acid)<br>Ac-Tyr-Val-Lys(biotinyl)-Asp-2,6-dimethylbenzoyloxymethylketone<br>Biotinyl-Tyr-Val-Ala-Asp-chloromethylketone<br>Biotinyl-Val-Ala-DL-Asp-fluoromethylketone<br>Fluorescein-6-carbonyl-Tyr-Val-Ala-DL-Asp(OMe)-fluoromethylketone<br>Fluorescein-6-carbonyl-Val-Ala-DL-Asp(OMe)-fluoromethylketone<br>Z-Asp-2,6-dichlorobenzoyloxymethylketone<br>Z-Tyr-Val-Ala-Asp-chloromethylketone<br>Z-Val-Ala-DL-Asp-fluoromethylketone<br>Z-Val-Ala-DL-Asp(OMe)-fluoromethylketone |
| Caspase-2 Inhibitors | Including, but not limited to<br>Ac-Val-Asp-Val-Ala-Asp-aldehyde (pseudo acid)<br>Fluorescein-6-carbonyl-Val-Asp(OMe)-Val-Ala-DL-Asp(OMe)-fluoromethylketone<br>Z-Val-Asp(OMe)-Val-Ala-DL-Asp(OMe)-fluoromethylketone |
| Caspase-3 Precursor Protease Inhibitors | Including, but not limited to<br>Ac-Glu-Ser-Met-Asp-aldehyde (pseudo acid)<br>Ac-Ile-Glu-Thr-Asp-aldehyde (pseudo acid) |
| Caspase-3 Inhibitors | Including, but not limited to<br>Ac-Asp-Glu-Val-Asp-aldehyde (pseudo acid)<br>Ac-Asp-Met-Gln-Asp-aldehyde (pseudo acid)<br>Biotinyl-Asp-Glu-Val-Asp-aldehyde(pseudo acid)<br>Caspase-3/7 Inhibitor II<br>Fluorescein-6-carbonyl-Asp(OMe)-Glu(OMe)-Val-DL-Asp(OMe)-fluoromethylketone<br>Z-Asp(OMe)-Gln-Met-DL-Asp(OMe)-fluoromethylketone<br>Z-Asp-Glu-Val-Asp-chloromethylketone<br>Z-Asp(OMe)-Glu(OMe)-Val-DL-Asp(OMe)-fluoromethylketone |
| Caspase-4 Inhibitors | Including, but not limited to<br>Ac-Leu-Glu-Val-Asp-aldehyde (pseudo acid)<br>Z-Tyr-Val-Ala-DL-Asp-fluoromethylketone |
| Caspase-6 Inhibitors | Including, but not limited to<br>Ac-Val-Glu-Ile-Asp-aldehyde (pseudo acid)<br>Fluorescein-6-carbonyl-Val-Glu(OMe)-Ile-DL-Asp(OMe)-fluoromethylketone<br>Z-Val-Glu(OMe)-Ile-DL-Asp(OMe)-fluoromethylketone |
| Caspase-8 Inhibitors | Including, but not limited to<br>Ac-Ile-Glu-Pro-Asp-aldehyde (pseudo acid)<br>Boc-Ala-Glu-Val-Asp-aldehyde (pseudo acid)<br>Fluorescein-6-carbonyl-Ile-Glu(OMe)-Thr-DL-Asp(OMe)-fluoromethylketone<br>Fluorescein-6-carbonyl-Leu-Glu(OMe)-Thr-DL-Asp(OMe)-fluoromethylketone<br>Z-Ile-Glu(OMe)-Thr-DL-Asp(OMe)-fluoromethylketone<br>Z-Leu-Glu(OMe)-Thr-DL-Asp(OMe)-fluoromethylketone<br>Z-LE(OMe)TD(OMe)-FMK |
| Caspase-9 Inhibitors | Including, but not limited to<br>Ac-Leu-Glu-His-Asp-aldehyde (pseudo acid)<br>Ac-Leu-Glu-His-Asp-chloromethylketone<br>Fluorescein-6-carbonyl-Leu-Glu(OMe)-His-DL-Asp(OMe)-fluoromethylketone |
| Caspase-10 Inhibitors | Including, but not limited to<br>Fluorescein-6-carbonyl-Ala-Glu(OMe)-Val-DL-Asp(OMe)-fluoromethylketone<br>Z-Ala-Glu-Val-DL-Asp-fluoromethylketone |
| 3.2. Calpain | |
| Calpain Inhibitor III<br>Peptide sequence:<br>Z-Val-Phe-CHO | A potent, cell-permeable inhibitor of calpain I and II (Ki = 8 nM). Reduces capsaicin-mediated cell death in cultured dorsal root ganglion. Reported to block A23187-induced suppression of neurite outgrowth in isolated hippocampal pyramidal neurons. Exhibits neuroprotective effect in glutamate-induced toxicity. |
| Calpain Inhibitor IV<br>Peptide sequence:<br>Z-Leu-Leu-Tyr-CH2F | A potent, cell-permeable, and irreversible inhibitor of calpain II (k2 = 28,900 M-1s-1). Also acts as an inhibitor of cathepsin L (k2 = 680,000 M-1s-1). |

TABLE 1-continued

Overview of apoptosis inhibitors

| Apoptosis inhibitor | Description |
| --- | --- |
| Calpain Inhibitor V<br>Peptide sequence:<br>Mu-Val-HPh-CH2F<br>(Mu = morpholinoureidyl;<br>HPh = homophenylalanyl) | A potent, cell-permeable, and irreversible inhibitor of calpain |
| Ac-Leu-Leu-Nle-al | Cell-permeable, peptide aldehyde inhibitor of calpain I (Ki = 190 nM), calpain II (Ki = 150 nM), cathepsin L (Ki = 0.5 nM) and other neutral cysteine proteases. Inhibits cell cycle progression at G1/S and metaphase/anaphase in CHO cells by inhibiting cyclin B degradation. Also stimulates HMG-CoA synthase transcription by inhibiting degradation of active SREBP-1 (sterol regulatory element-binding protein 1). Protects against neuronal damage caused by hypoxia and ischemia. Inhibits apoptosis in thymocytes and metamyelocytes. Also prevents nitric oxide production by activated macrophages by interfering with the transcription of inducible nitric oxide synthase (iNOS; NOS II). Inhibits proteolytic degradation of IkBalpha and IkBβ in RAW macrophages induced with LPS. It also prolong association of MHC class I molecules with the transporters associated with antigen processing |
| Z-LLY-FMK | Calpain |
| N-Acetyl-Leu-Leu-Met | Calpain 1 |
| N-Acetyl-Leu-Leu-Nle-CHO | Calpain 1 |
| 3.3. others | |
| BAPTA/AM | Membrane-permeable form of BAPTA. Can be loaded into a wide variety of cells, where it is hydrolyzed by cytosolic esterases and is trapped intracellularly as the active chelator BAPTA. Prevents cocaine-induced ventricular fibrillations. Abolishes vitamin D3-induced increase in intracellular Ca2+. Induces inactivation of protein kinase C. Also inhibits thapsigargin-induced apoptosis in rat thymocytes. |
| Granzyme B Inhibitor I<br>Peptide sequence:<br>Z-Ala-Ala-Asp-CH2Cl | A weak inhibitor of the human and murine granzyme B. Also inhibits the apoptosis-related DNA fragmentation in lymphocytes by fragmentin 2, a rat lymphocyte granule protease homologous to granzyme B (ID50 = 300 nM). |
| Granzyme B Inhibitor II<br>Peptide sequence:<br>Ac-Ile-Glu-Thr-Asp-CHO | A potent, reversible inhibitor of granzyme B and caspase-8 (Ki = 1 nM). Also inhibits caspase-1 (<6 nM), caspase-6 (5.6 nM), and caspase-10 (27 nM). |
| Granzyme B Inhibitor IV<br>Peptide sequence:<br>Ac-Ile-Glu-Pro-Asp-CHO | A reversible inhibitor of granzyme B and caspase-8 |
| Leupeptin, Hemisulfate, Microbial | A reversible inhibitor of trypsin-like proteases and cysteine proteases. Also known to inhibit activation-induced programmed cell death and to restore defective immune responses of HIV+ donors |
| N-Ethylmaleimide | Sulfhydryl alkylating reagent that inhibits H+-ATPase and suppresses the short circuit current (IC50 = 22 μM) in pancreatic duct cells. Inactivates NADP-dependent isocitrate dehydrogenase. Also a potent inhibitor of both Mg2+ and Ca2+/Mg2+-stimulated DNA fragmentation in rat liver nuclei. Stimulates arachidonic acid release through activation of PLA2 in endothelial cells |
| Nα-Tosyl-Lys Chloromethyl Ketone, Hydrochloride (TLCK) | Inhibits trypsin-like serine proteinases. Irreversibly inactivates trypsin without affecting chymotrypsin. Prevents nitric oxide production by activated macrophages by interfering with transcription of the iNOS gene. Blocks cell-cell adhesion and binding of HIV-1 virus to the target cells. In macrophages, blocks nitric oxide synthase induced by interferon-γ and lipopolysaccharides (EC50 = 80 μM). Prevents endonucleolysis accompanying apoptotic death of HL-60 leukemia cells and normal thymocytes |
| Omi/HtrA2 Protease Inhibitor, Ucf-101 | A cell-permeable furfurylidine-thiobarbituric acid compound that acts as a potent, specific, competitive, and reversible inhibitor of the pro-apoptotic, heat-inducible, mitochondrial serine protease Omi/HtrA2 (IC50 = 9.5 μM for His-Omi134-458). Shows very little activity against various other serine proteases tested (IC50 ≥ 200 pM). Reported to block Omi/HtrA2 induced cell death in caspase-9 (-/-) null fibroblasts. |
| Phenylarsine Oxide | A membrane-permeable protein tyrosine phosphatase inhibitor (IC50 = 18 μM). Stimulates 2-deoxyglucose transport in insulin-resistant human skeletal muscle and activates p56Ick protein tyrosine kinase. Blocks TNF-α-dependent activation of NE-KB in human myeloid ML-1a cells. PAO inhibits the protease activities of recombinant human caspases as well as endogenous caspases that are active in extracts of pre-apoptotic chicken DU249 cells (S/M extracts). |

TABLE 1-continued

Overview of apoptosis inhibitors

| Apoptosis inhibitor | Description |
| --- | --- |
| Phorbol-12,13-dibutyrate | Activates protein kinase C. Stimulates the phosphorylation of Na+,K+− ATPase, thereby inhibiting its activity. Promotes the expression of inducible NOS in cultured hepatocytes. |
| Hypericin | Inhibits PKC, CKII, MAP Kinase, Insulin R, EGFR, PI-3 Kinase and also noted to possess antiviral activity. |
| Butyrolactone I | A cell-permeable and highly selective inhibitor of cyclin-dependent protein kinases (Cdks) that inhibits cell cycle progression at the G1/S and G2/M transitions. Inhibits p34cdk1/cyclinB (Cdk1; IC50 = 680 nM). Also selectively inhibits Cdk2 and Cdk5 kinases. Has little effect on casein kinase I, casein kinase II, EGF receptor kinase, MAP kinase, PKA, and PKC. Shown to prevent the phosphorylation of retinoblastoma protein and H1 histone. Also blocks Fas-induced apoptosis in HL-60 cells and shows antitumor effects on human lung cancer cell lines |
| Nilotinib | Specific BCR-ABL-Tyrosinkinase-Inhibitor |
| Quercetin(Sophoretin) | Quercetin is a PI3K and PKC inhibitor with IC50 of 3.8 µM and 15 µg/ml. It strongly abrogated PI3K and Src kinases, mildly inhibited Akt1/2, and slightly affected PKC, p38 and ERK1/2. [1][2] Quercetin is a naturally-occurring polar auxin transport inhibitor with IC50 of 0.8, 16.7, 6.1, 11.36 µM for the inhibition of LDH% release, the inhibition of TNF-induced PMN-EC adhesion, TNF-induced inhibition of DNA synthesis and proliferation |

EXAMPLES

In the following examples, materials and methods of the present invention are provided. It should be understood that these examples are for illustrative purpose only and are not to be construed as limiting this invention in any manner.

I. Cell and Transcript Level Stabilising Properties of Different Primary and Secondary Carboxylic Acid Amides 1. Materials and Methods A test system and study setup was established that allows the identification of reagent compositions that have gene transcript stabilisation capabilities, as indicated by constant levels of transcripts from selected genes (c-fos, IL-1 beta, IL-8, p53). These transcripts were identified in prior studies as very unstable transcripts during storage, which are induced or down regulated (gains and losses of transcripts) within minutes after blood collection and were therefore chosen as "worst case" markers for screening purposes.

Moreover to exclude any possible influence of the RNA preparation protocol on the analysis of transcript levels, the same RNA preparation technology used for the [+] control of sample stabilisation was also used for [−] control of samples stabilisation and for test samples.

Blood was collected from multiple donors into replicate EDTA blood tubes (BD, [−] control of sample stabilisation) and PAXgene Blood RNA Tubes (PreAnalytiX) serving as [+] control of sample stabilisation. PAXgene Blood RNA tubes contain a composition (see also background of the invention) that lysis cells and thereby "freeze" the gene transcription profile. PAXgene Blood RNA tubes are for stabilizing blood for gene expression analysis. One aim was to find stabilization method that not based on cell lysis but achieves the same or similar performance as the PAXgene Blood RNA tubes in transcript level stabilization. Therefore, samples collected in PAXgene Blood and thus treated with the stabilization composition contained therein were used as positive control in the experimental set up. Immediately after blood collection half of the EDTA blood samples were treated with RNA stabilisation test solution, resulting in blood test samples. 1 ml stabilisation additive was added to 9 ml EDTA blood. The blood and stabiliser solution was mixed by tube inversion for 8-10 times. All blood tubes were incubated at RT for 0, 24 and 72 hours. PAXgene Blood RNA Tubes defined as without incubation (test timepoint 0 h) were incubated for 2 h as this is the minimal cell lysis and RNA precipitation time required to isolate RNA from PAXgene Blood RNA Tubes. After incubation, PAXgene Blood RNA Tube samples were frozen at −20° C., while aliquots of 2.5 ml per EDTA blood and samples of EDTA blood mixed with stabiliser were transferred at test timepoint 0 h or after the stabilization period to PAXgene Blood RNA Tubes, mixed by tube inversion as described and incubated for 6 h in PAXgene Blood RNA Tubes for lysis followed by storage at −20° C.

RNA preparation was performed from all blood samples that were finally in PAXgene Blood RNA Tubes with the PAXgene 96 Blood RNA Kit (QIAGEN) according to the protocol described in the handbook after thawing and equilibration of tubes to room temperature Quantity (RNA yield) and quality (RNA purity, RNA integrity) of RNA was measured by UV spectroscopy and miniaturised capillary gel electrophoresis with RIN calculation (Nanochips on Agilent Bioanalyzer).

Transcript levels of all RNA samples were analysed by real time RT-PCR using monoplex assays of FOS, IL1B, IL8 and TP53, normalized to the amount of template input into the reaction. Resulting CT values reflecting the amount of transcripts were directly compared. Relative transcripts levels unaffected from blood sample incubation at RT were indicated by constant CT values, while gains of transcripts (e.g., by gene induction) were indicated by lower CT and loss of transcripts (e.g., by gene repression) by higher CT values.

Where indicated, cell morphology was investigated by microscopic evaluation of blood smears and cell integrity by flow cytometry (FC).

2. Tested Carboxylic Acid Amides

Example 1

Stabilization Using Formamide

Blood was collected from multiple donors into replicate EDTA blood tubes (BD, [−] control of sample stabilisation)

and PAXgene Blood RNA Tubes (PreAnalytiX) serving as [+] control of sample stabilisation. Immediately after blood collection half of the EDTA blood samples were treated with RNA stabilisation test solution, resulting in blood test samples. In detail, 1 ml stabilisation additive (50% v/v formamide, 5× MOPS buffer, pH5.5) was added to 9 ml EDTA blood. Blood mixing, incubation, transfer of blood sample aliquots to PAXgene Blood RNA Tubes, freezing, storage and RNA preparation was done as described above. RNA was subjected to transcript level analysis as described above in Material and methods. Quantity (RNA yield) and quality (RNA purity, RNA integrity) of RNA was measured by UV spectroscopy and miniaturised capillary gel electrophoresis with RIN calculation (Nanochips on Agilent Bioanalyzer). Transcript levels of all RNA samples were analysed by real time RT-PCR using monoplex assays of FOS, IL1B, IL8 and TP53, normalized to the amount of template input into the reaction. Resulting CT values reflecting the amount of transcripts were directly compared. Relative transcripts levels unaffected from blood sample incubation at RT were indicated by constant CT values, while gains of transcripts (e.g., by gene induction) were indicated by lower CT and loss of transcripts (e.g., by gene repression) by higher CT values. Cell morphology was investigated by microscopic evaluation of blood smears and cell integrity by flow cytometry (FC).

RNA could be isolated from all samples with high yield. Thus, it was confirmed that the stabilization did not impair the subsequent RNA isolation. Purity of RNA prepared from all samples was in the range of highly pure RNA (A260/A280 in the range of 2.0 to 2.2). Furthermore, RNA integrity of the isolated RNA was high (RIN>8).

As expected, the relative levels of transcripts from four selected marker genes stayed stable in the PAXgene Blood RNA Tubes and were altered in the EDTA tubes that did not receive the stabiliser (ex vivo gene induction/gain of transcripts of FOS, IL8 and gene repression/loss of transcripts of IL1B, TP53). EDTA blood samples mixed with the stabiliser formamide showed stabilised expression levels indicated by unchanged or by only minor minimal changes of CT values over time of blood sample storage. Thus, formamide is highly effective in stabilizing transcript levels and thus the gene transcription profile of cells contained in the blood sample. The results are shown in FIGS. 1 to 4.

Figure 5:
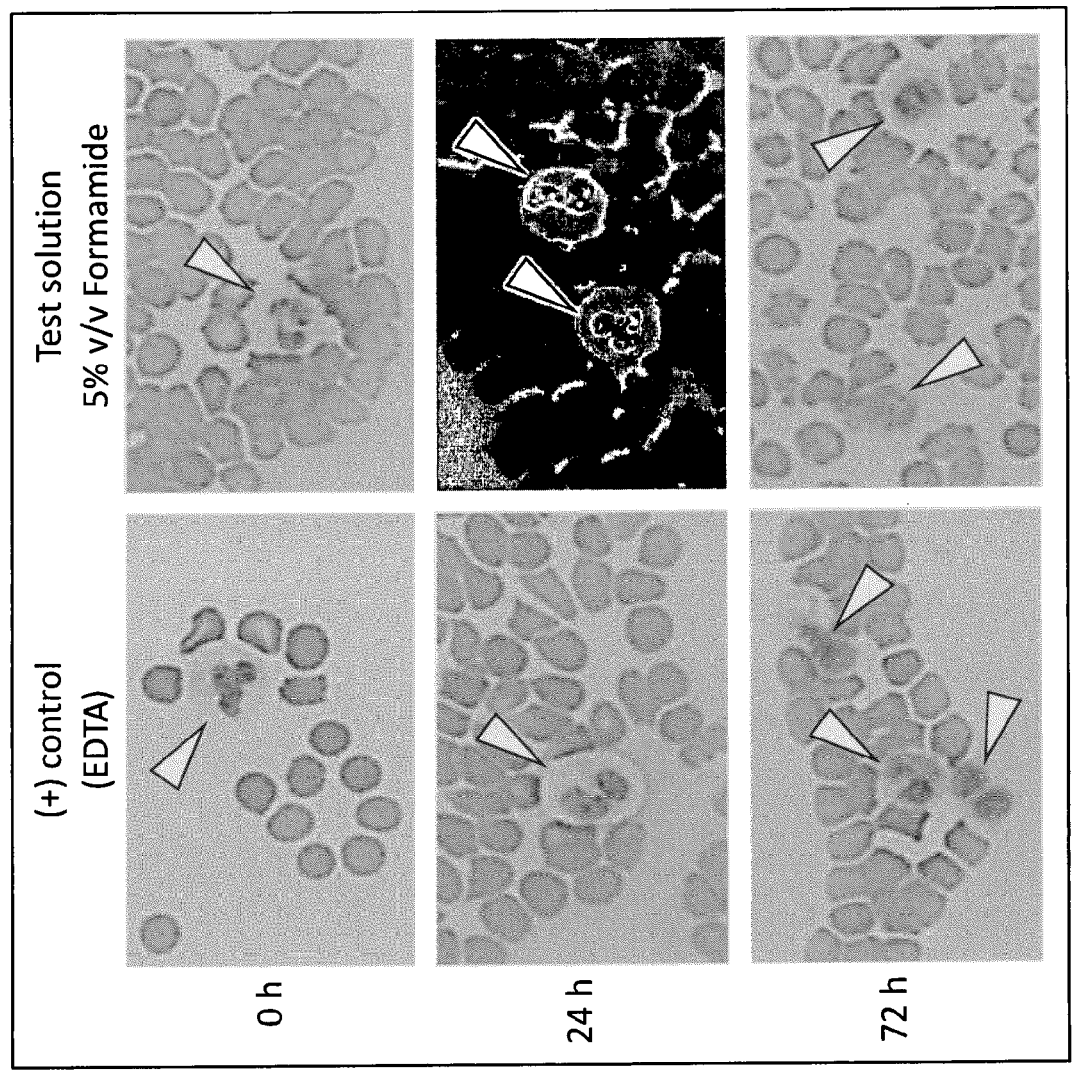
FIG. 5: Microscopic evaluation of H&E stained blood slides from aliquots of peripheral blood samples of one donor of example 1.

Intact white blood cells were detected in untreated EDTA blood and EDTA blood mixed with the stabilisation additive (test solution) that was incubated at RT for up to three days (see FIG. 5). This demonstrated that the stabilisation additive did not act lytic on WBC. Blood was directly drawn into BD EDTA tubes and replicate samples were kept untreated ([+] control [EDTA]) or were treated with test solution (final concentration of 5% v/v formamide and 0.5× MOPS buffer [pH5.5]) as described above. Immediately after collection and treatment of samples, blood aliquots were analysed without incubation (0 h samples), while remaining samples were incubated at RT for one and three days (24 h and 72 h samples) prior to microscopic cell integrity analysis. Blood smears were 40× magnified and microscopic images were taken to evaluate cell integrity. Image sections containing single WBC were digitally enlarged to document the presence of intact cells. Untreated EDTA blood samples ([+] control [EDTA]) served as positive control of blood samples containing intact cells. Indicated by white arrow heads within each picture are WBC (nucleus containing cells) surrounded by erythrocytes (nucleus-free cells).

Figure 6:
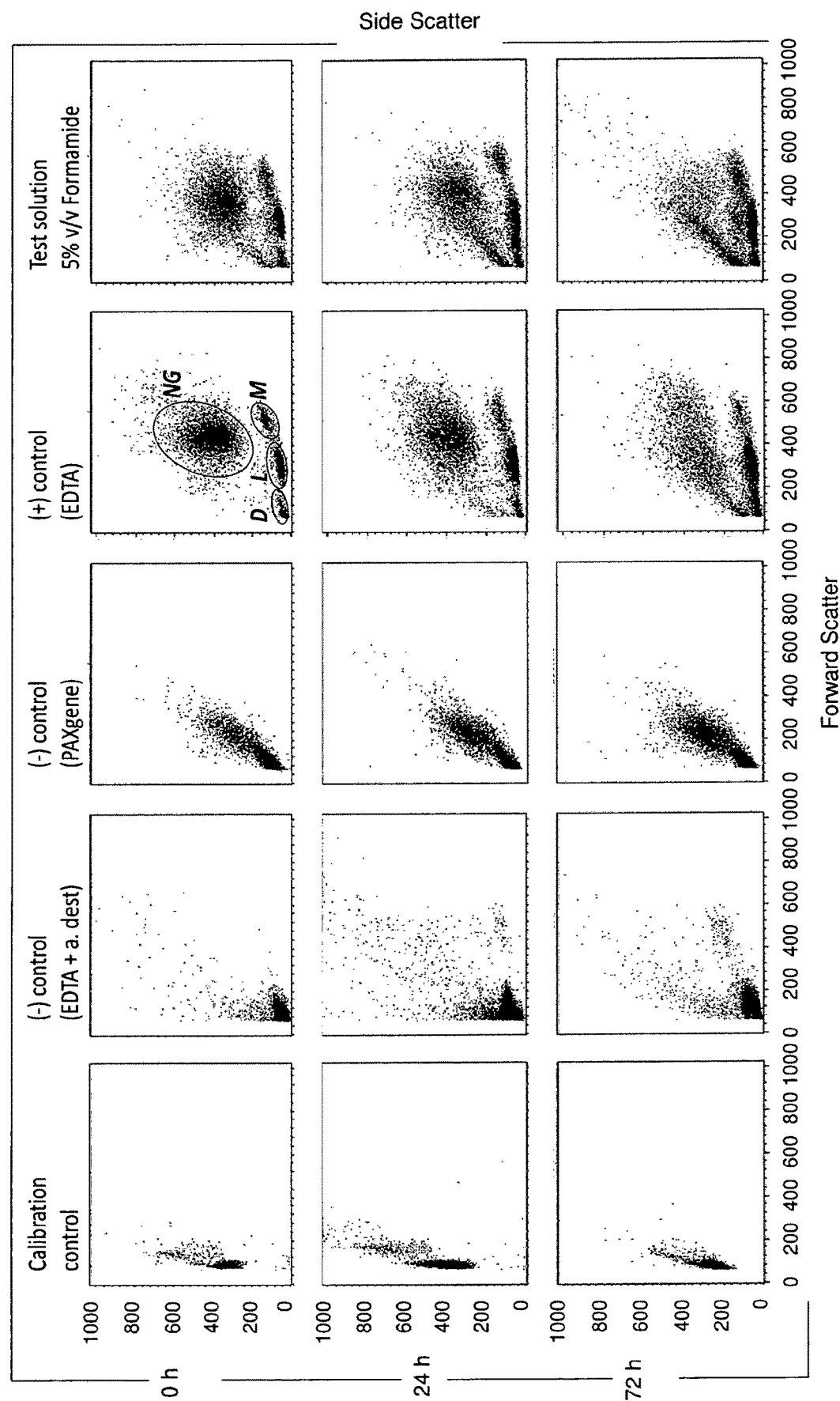
FIG. 6: Flow cytometry (FC) analysis of peripheral blood samples of one donor of example 1. Blood was directly drawn into BD EDTA tubes and PreAnalytiX PAXgene Blood RNA Tubes (PAXgene). Replicate EDTA blood samples were kept untreated ([+] control [EDTA], [−] control [EDTA+a. dest]) or were treated with final concentration of 5% v/v formamide and 0.5× MOPS buffer (pH5.5) as described in example 1. Immediately after collection and treatment of samples, blood aliquots were analysed without incubation (0 h samples), while remaining samples were incubated at RT for one and three days (24 h and 72 h samples) prior to FC analysis. Shown per picture are the size (x-axis=forward scatter) and granularity (y-axis=sideward scatter) of 10,000 events per sample aliquot tested that contain signals of cells, cell debris and particles. The different populations of white blood cells that are distinguishable from each other in FC analysis (L, M, NG) and the cell-free fraction (D) are indicated by circles for the (+) control (EDTA) sample. They are as follows:
D=Debris, subcellular components, fragments of cells
L=Lymphocytes
M=Monocytes
NG=Neutrophilic granulocytes
(+) control (EDTA): Untreated EDTA blood sample serving as a positive control of cell stabilisation.
(−) control (EDTA+a. dest): Untreated EDTA blood sample that was completely lysed by addition of deionized water serving as a negative control of cell stabilisation.
(−) control (PAXgene): PAXgene blood sample that contains completely lysed cells as all cells get directly lysed during blood collection into the tube as soon as blood gets into contact with the RNA stabilisation additive in the tube. This sample served as an additional negative control of cell stabilisation.
Calibration control: CALIBRITE Beads (BD) of known fluorescence and diameter serving to calibrate the BD FACSCalibur™ instrument.
Test solution 5% v/v Formamide: EDTA blood samples containing 5% v/v formamide and 0.5× MOPS buffer (pH5.5).
Figure 7:
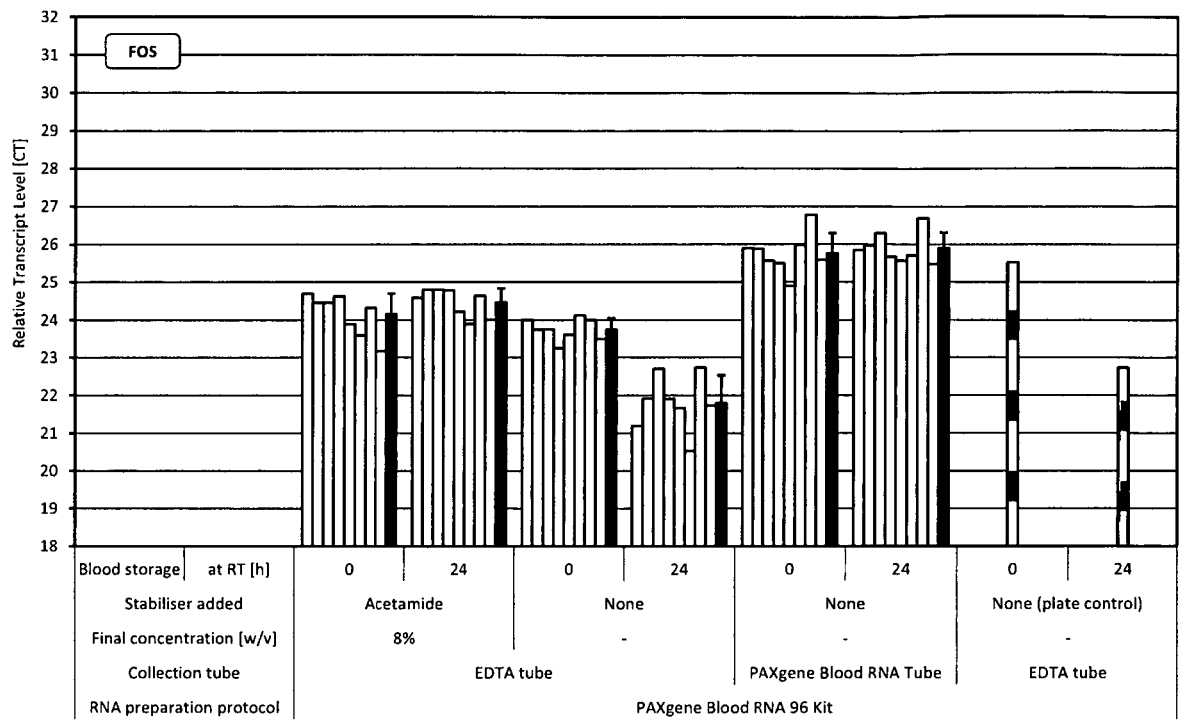
FIGS. 7 to 10: Relative transcript levels of FOS, IL1B, IL8 and TP53 (from FIGS. 7 to 10) in blood samples collected from eight donors into EDTA tubes and PAXgene Blood RNA Tubes. EDTA blood samples were kept untreated or mixed with final concentration of 8% w/v acetamide immediately after blood collection. RNA isolation was performed from blood samples without and from replicate tubes after incubation for one day at RT. Transcripts were analysed using real time monoplex RT-PCR assays. Transcript levels given as cycle thresholds (CT) of individual samples are shown as white bars, means as black solid bars with standard deviations and control samples of an additional donor of a different experiment serving as positive control of gene expression changes and successful RT-PCR within each PCR run (plate control) as shaded bars.
Figure 8:
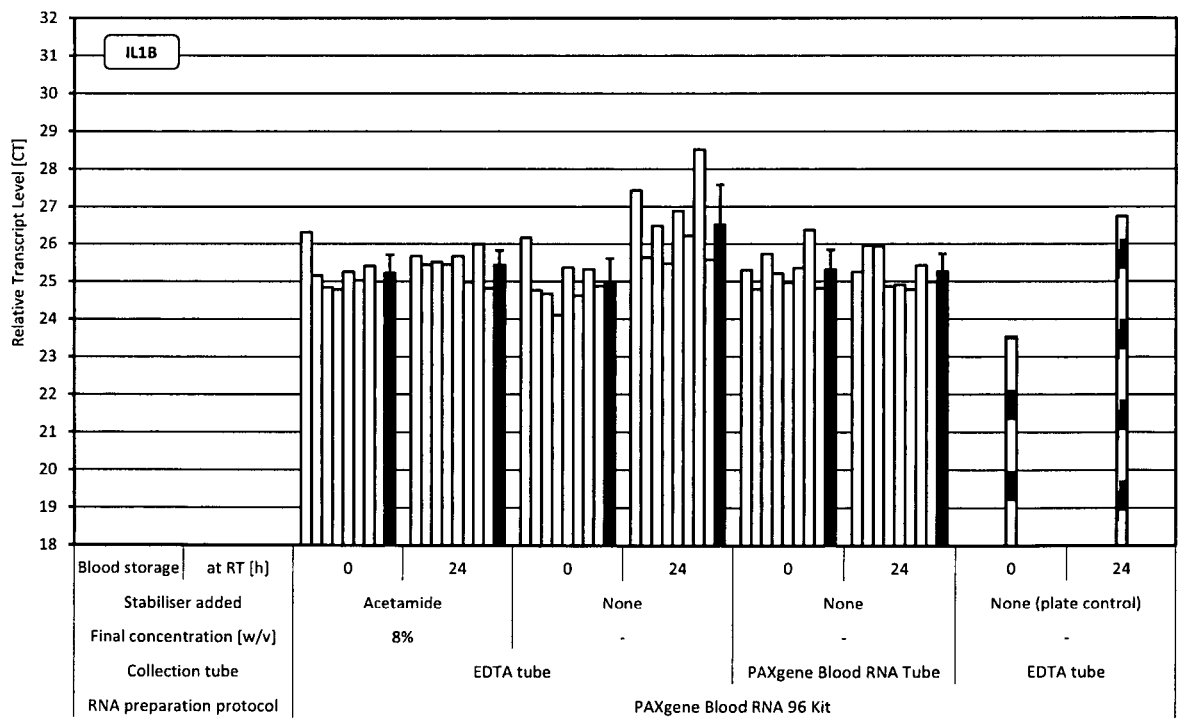
Figure 9:
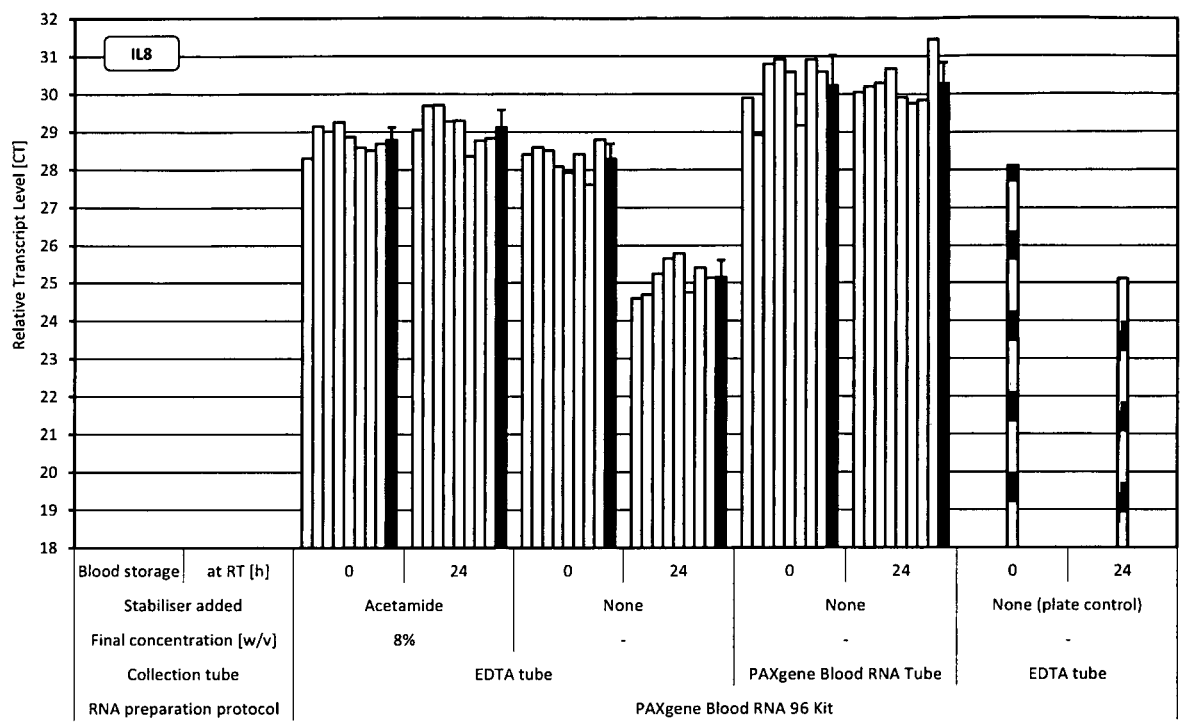
Figure 10:
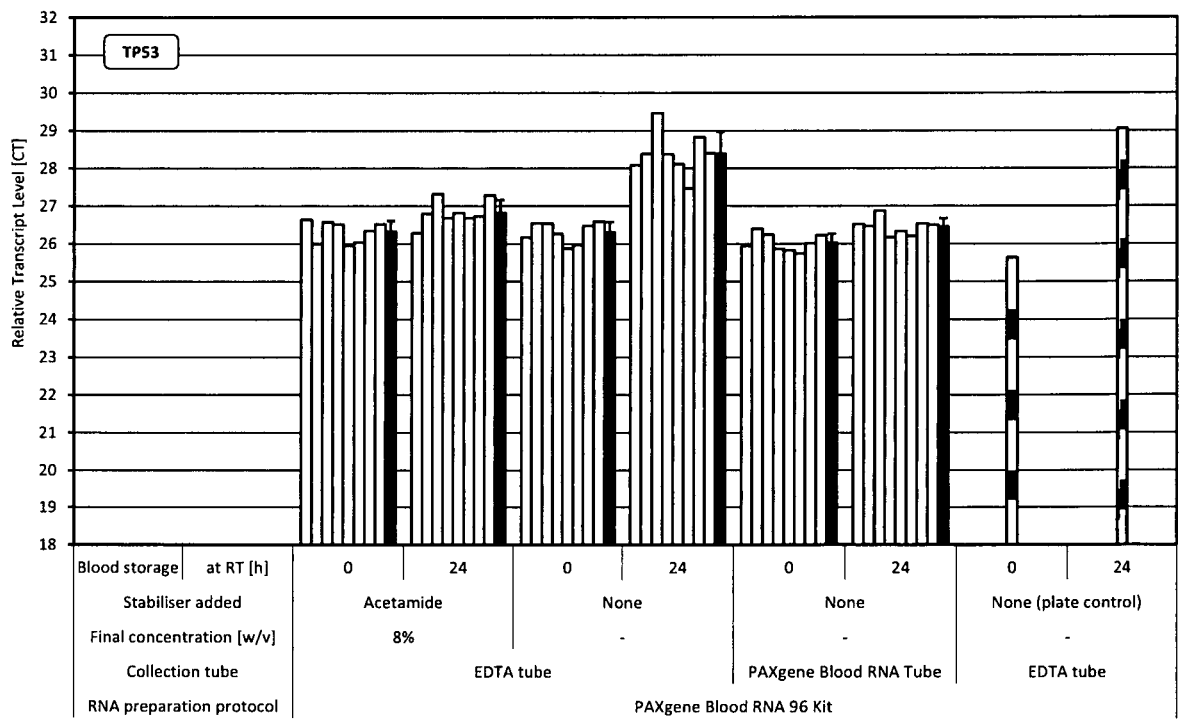
Figure 11:
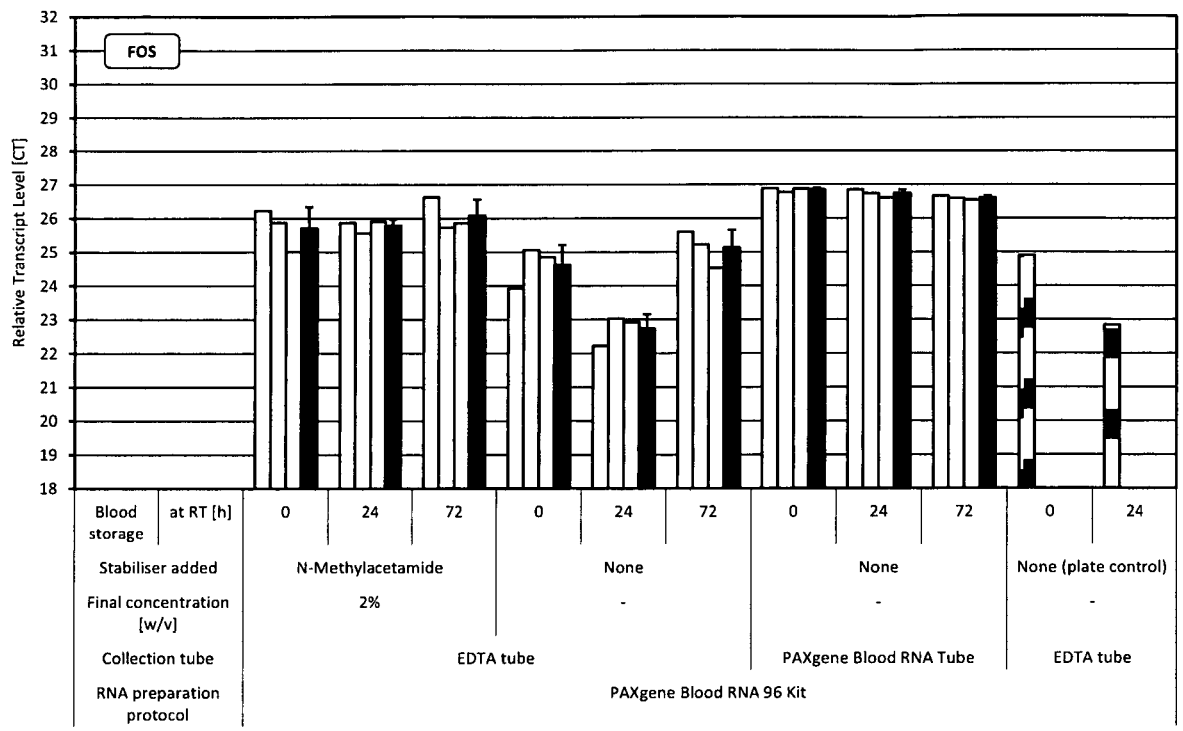
FIGS. 11 to 14: Relative transcript levels of FOS, IL1B, IL8 and TP53 (from FIGS. 11 to 14) in blood samples collected from three donors into EDTA tubes and PAXgene Blood RNA Tubes. EDTA blood samples were kept untreated or mixed with final concentration of 2% w/v N-methylacetamide (final concentration in the stabilized blood composition) immediately after blood collection. RNA isolation was performed from blood samples without and from replicate tubes after incubation for one and three days at RT. Transcripts were analysed using real time monoplex RT-PCR assays. Transcript levels given as cycle thresholds (CT) of individual samples are shown as white bars, means as black solid bars with standard deviations and control samples of an additional donor of a different experiment serving as positive control of gene expression changes and successful RT-PCR within each PCR run (plate control) as shaded bars.
Figure 12:
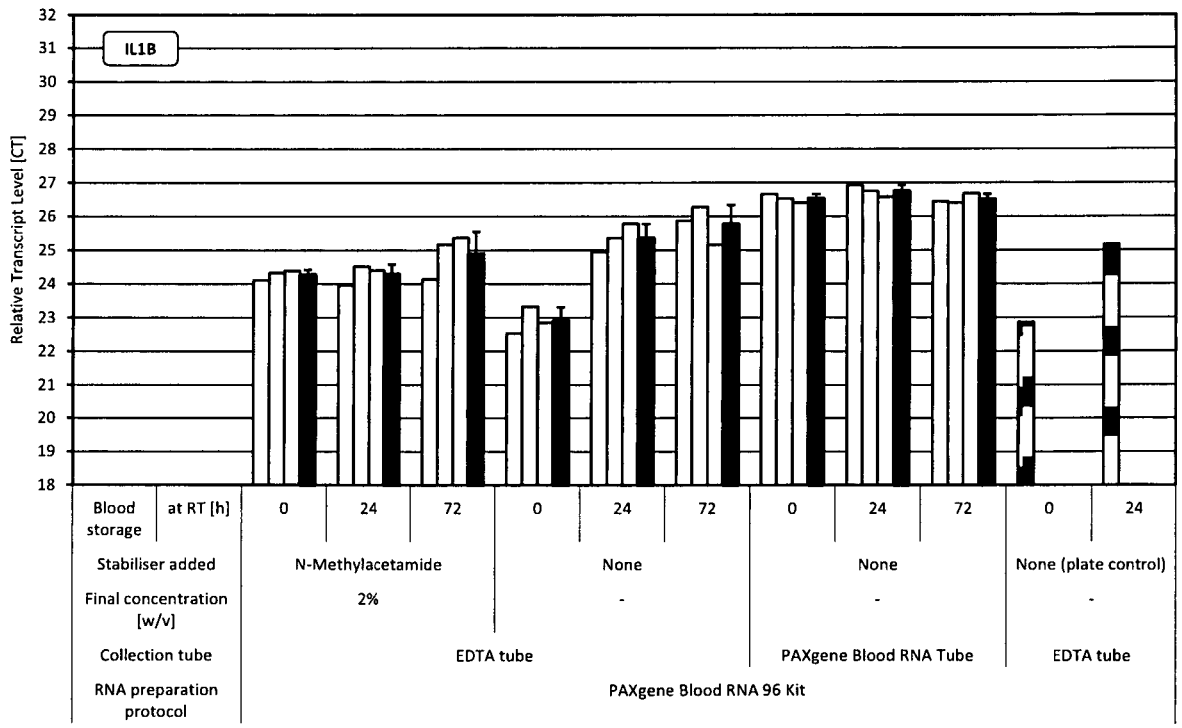
Figure 13:
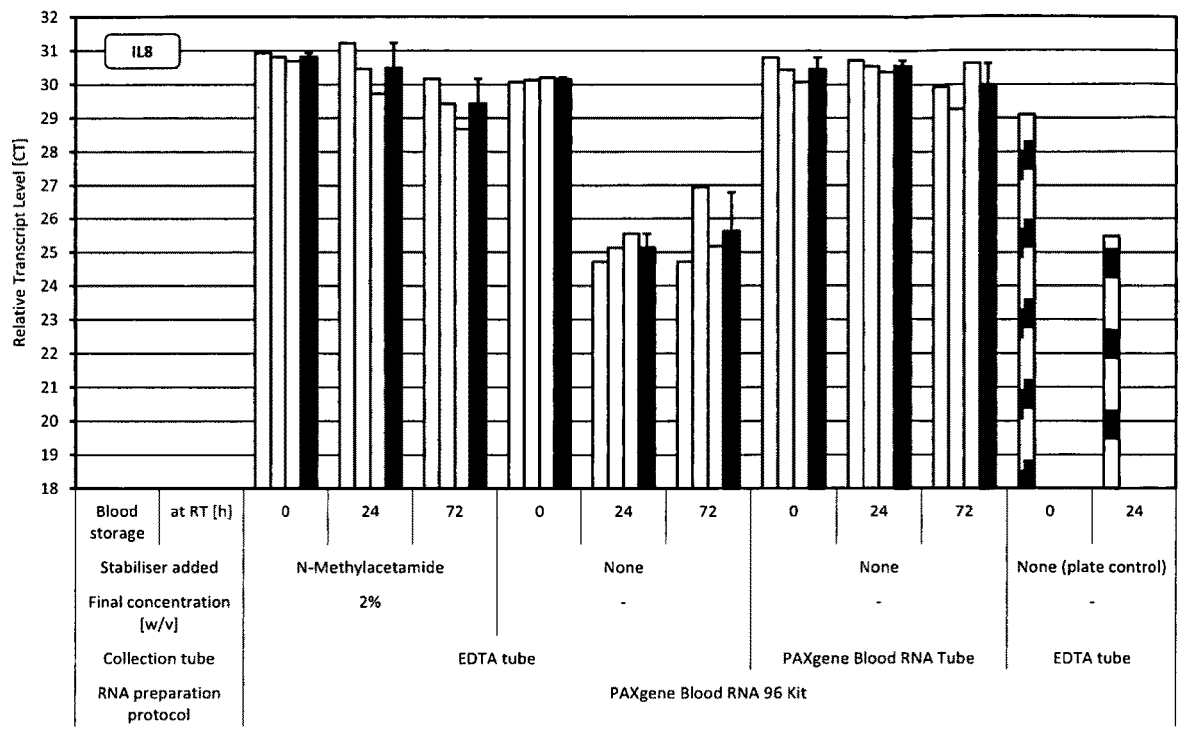
Figure 14:
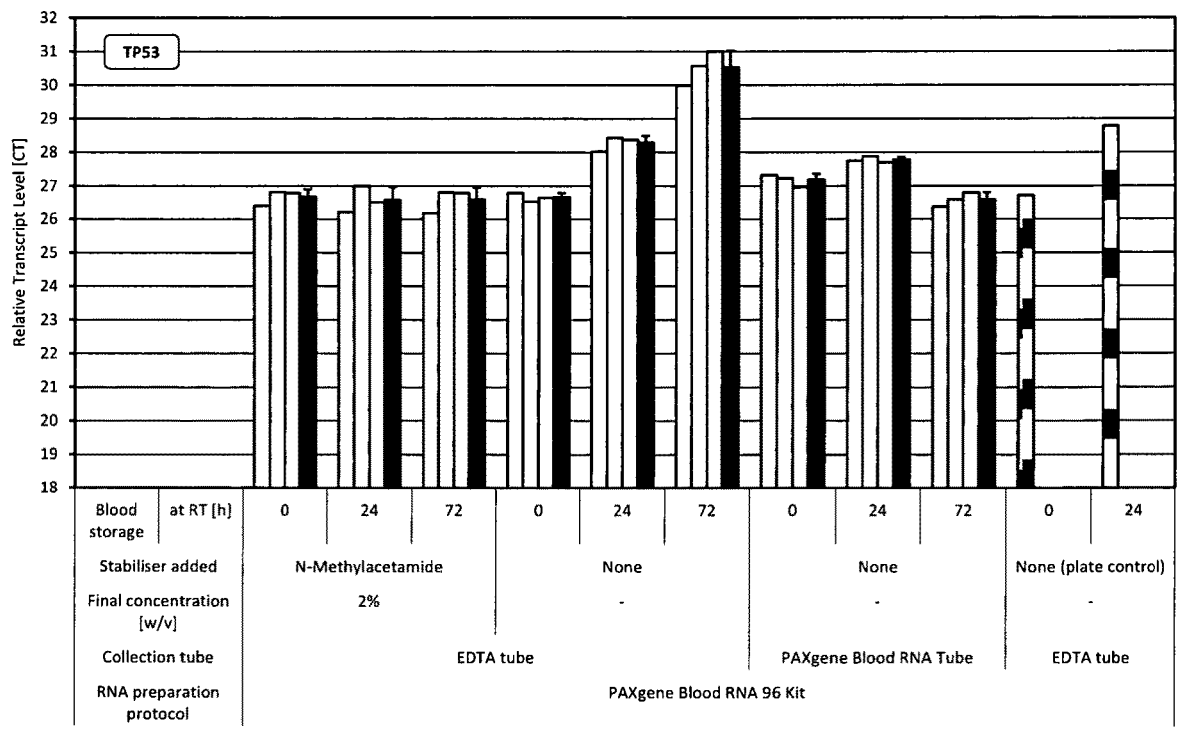
Figure 15:
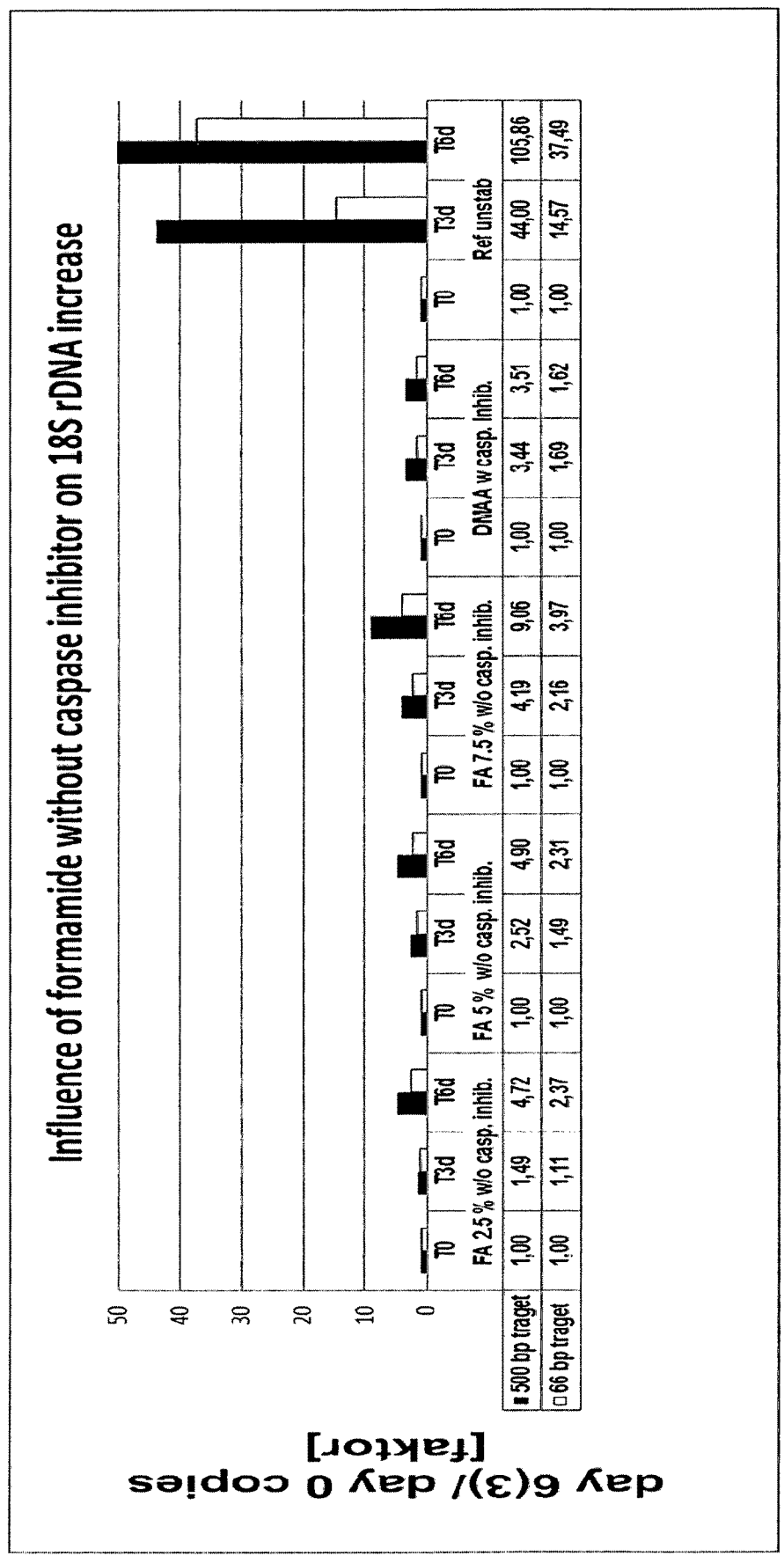
FIGS. 15 to 21: Stabilization of the extracellular nucleic acid population using formamide in different concentrations either alone or in combination with a caspase inhibitor.
Figure 16:
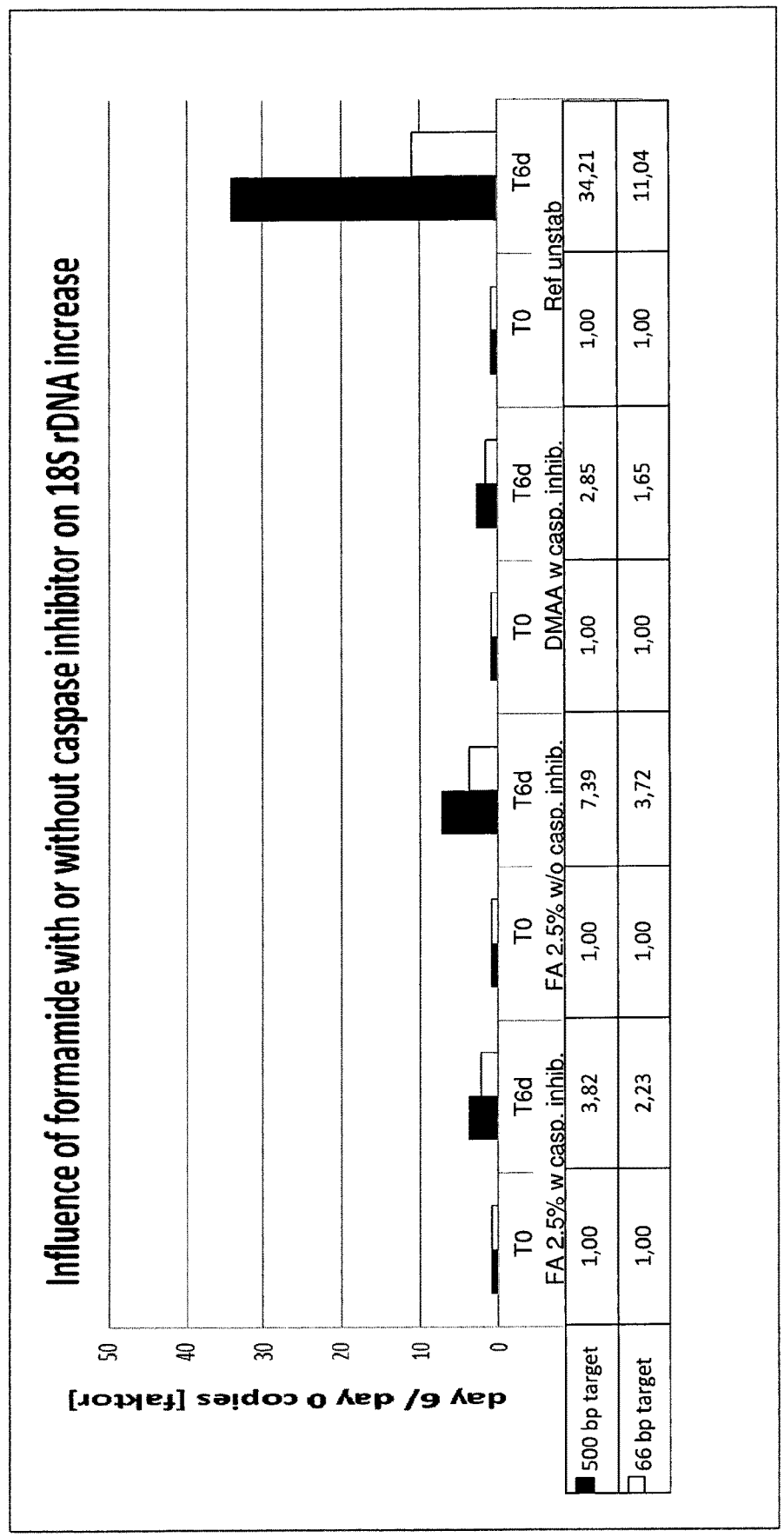
Figure 17:
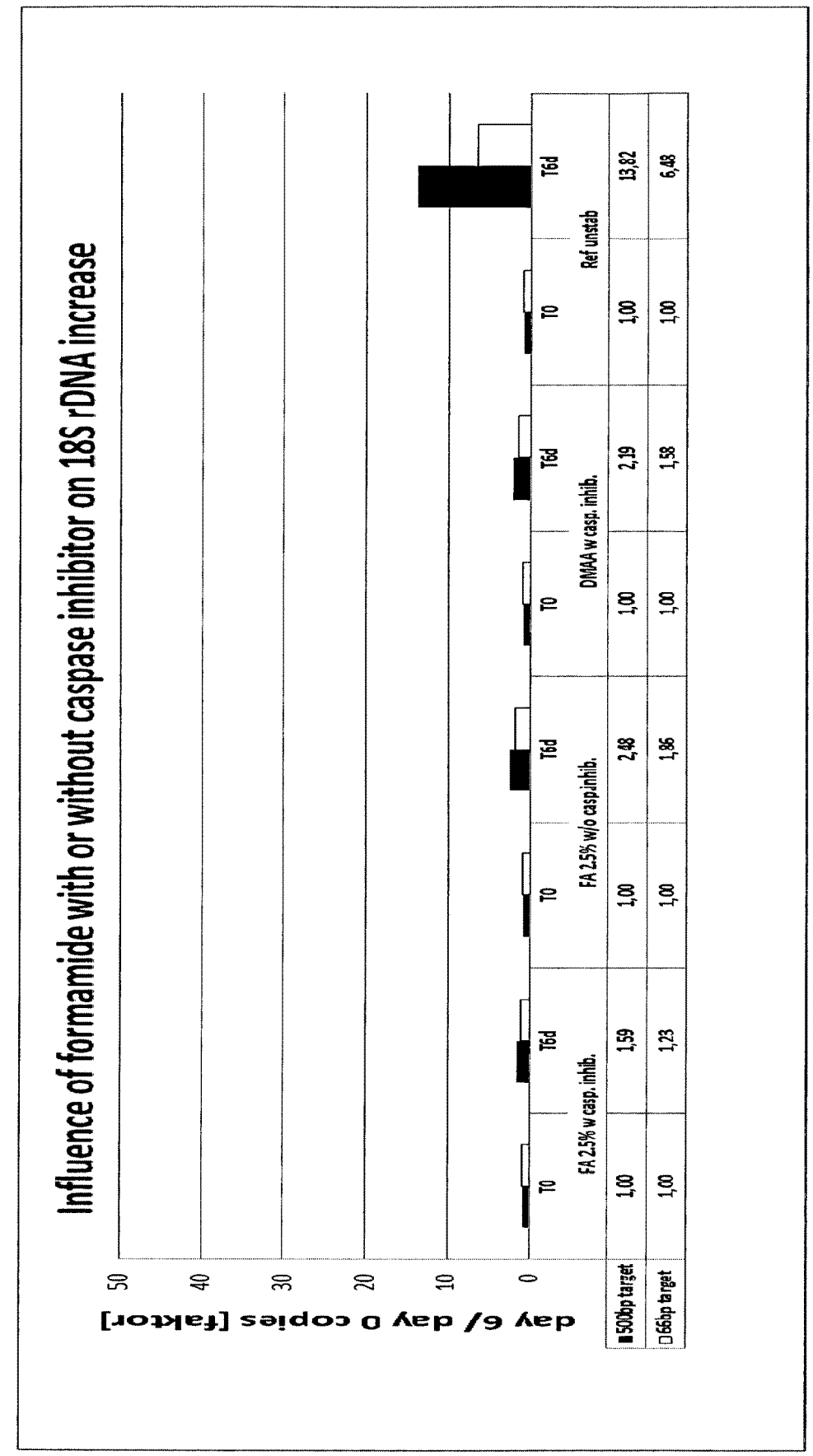
Figure 18:
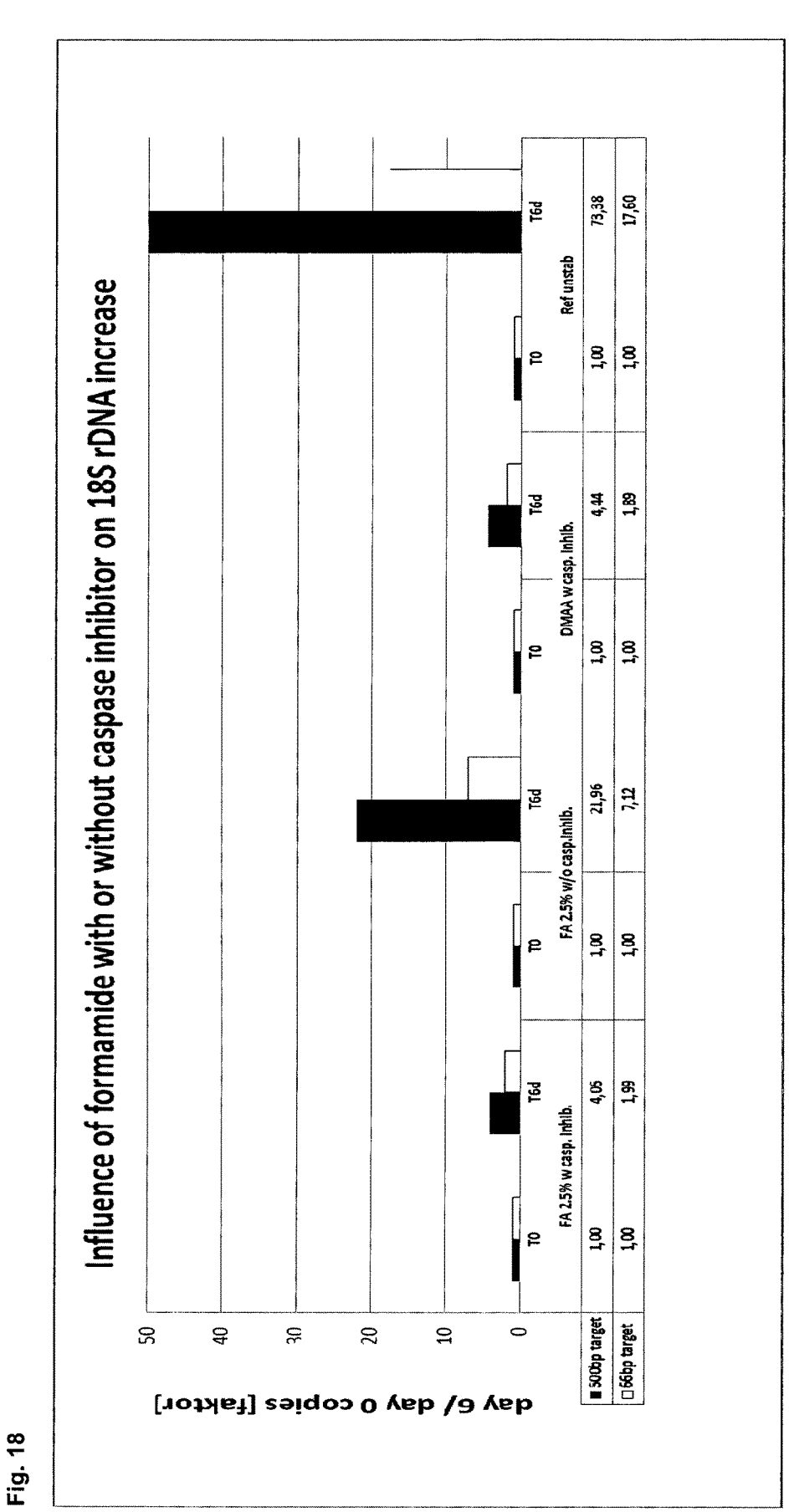

The results obtained by microscopic analysis were verified by the analysis of cell integrity with flow cytometry. FC showed the presence of intact WBC in untreated EDTA blood and EDTA blood mixed with the stabilisation additive (test solution) that was incubated at RT for up to three days (see FIG. 6). Lymphocytes and monocytes were not affected by lysis as the result of blood incubation in untreated and treated samples. Some lysis appeared to have occurred with neutrophilic granuloctes at longer storage. However, as the release of genomic DNA is still efficiently prevented (see examples in section II below), it may well be that the seen differences in the FC profiles have other reasons. However, not all white blood cells may be equally well stabilized during longer stabilization periods. However, intact cells were detected and the detected cell populations are important for certain diagnostic applications which aim e.g. at the analysis of lymphocytes.

The experiments performed in example 1 show that formamide is effective in stabilizing transcript levels and thus the transcriptome in blood samples. RNA could be isolated with good yield and purity suitable for RT-PCR analysis. Furthermore, cells could be isolated from the stabilized samples.

Example 2

Stabilization Using Acetamide

EDTA blood samples were kept untreated or mixed with 8% w/v acetamide immediately after blood collection. Blood samples collected in PAXgene RNA blood tubes served again as control. Sample handling and RNA isolation was performed from blood samples without and from replicate tubes after incubation for one day at RT as described in material and methods. Transcript levels of all RNA samples were analysed as described in material and methods by real time RT-PCR using monoplex assays of FOS, IL1B, IL8 and TP53, normalized to the amount of template input into the reaction. The results are shown in FIGS. 7 to 10. Resulting CT values reflecting the amount of transcripts were directly compared. Relative transcripts levels unaffected from blood sample incubation at RT were indicated by constant CT values, while gains of transcripts (e.g., by gene induction) were indicated by lower CT and losses of transcripts (e.g., by gene repression) by higher CT values. As can be seen, also the primary carboxylic acid amide acetamide was highly effective in stabilizing transcript levels.

Example 3

Stabilization Using N-Methylacetamide

Samples were prepared and processed as described in example 2, however using 2% (w/v) N-methylacetamide as stabilizer in the composition comprising the blood sample and the stabilising agent. The results are shown in FIGS. 11 to 14. As can be seen, the secondary carboxylic acid amide N-methylacetamide was effective in stabilizing transcript levels for up to three days.

Examples 1 to 3 show that different primary and secondary carboxylic acid amides are highly effective in stabilizing the gene transcription profile of cells in blood samples.

II. Stabilization of the Extracellular Nucleic Acid Population in Blood Samples Using Different Primary and Secondary Carboxylic Acid Amides Materials and Methods Different primary and secondary carboxylic acid amides were tested for their ability to stabilize a cell-containing biological sample, here a whole blood sample, either alone or in combination with a caspase inhibitor. As can be seen from the below examples, primary and secondary carboxylic acid amides were found to efficiently stabilize blood samples and in particular, were found to inhibit the release of genomic DNA from cells comprised in the stabilized blood sample. Thus, they were capable of stabilizing the extracellular nucleic acid population. Furthermore, it was found that using primary and secondary carboxylic acid amides in isolation using the QIAamp circulating nucleic acid kit (QIAGEN) according to the manufacturer's instructions.

The isolated extracellular DNA was analyzed using two different qPCR assays, targeting different fragment lengths of the 18S ribosomal DNA:

18S ribosomal DNA: 66 by amplicon 18S ribosomal DNA: 500 by amplicon

TABLE 2 summarizes the information of the used DNA target sequences detected by qPCR

| Target description | position | position | Sequence 5'-3' | dye |
|---|---|---|---|---|
| h 18S rDNA 66 bp amplicon | p12-region of chromosome 13, 14, 15, 21, 22 | Forward reverse probe | GCCGCTAGAGGTGAAATTCTTG CATTCTTGGCAAATGCTTTCG ACCGGCGCAAGACGGACCAGA | 5' Cy5-BHQ 3' |
| h18S rDNA 500 bp amplicon | p12-region of chromosome 13, 14, 15, 21, 22 | forward reverse probe | GTCGCTCGCTCCTCTCCTACTT GGCTGCTGGCACCAGACTT CTAATACATGCCGACGGGCGCTGAC | 5' FAM-BHQ 3' | combination with a caspase inhibitor advantageously improved the achieved stabilization effect. A respective combination resulted in a prolonged stabilization effect and furthermore, showed less variation in the stabilization effect achieved with blood samples obtained from different donors. This is an important advantage, as it provides a uniform, reliable stabilization method for blood samples which preserves the extracellular nucleic acid population.

Blood Collection and Stabilization

Blood obtained from donors was collected into 10 ml K2 EDTA tubes (BD). 4.5 ml of the respectively collected blood was mixed with 0.9 ml of different stabilization solutions (see below examples on the details of the tested stabilization solutions).

All stabilized blood samples were set up in triplicates per condition and test time point. At time point 0 (reference), immediately after mixing the stabilization solution and blood, plasma was generated and the circulating extracellular DNA was extracted. The residual stabilized blood sample was stored for three days and six days at room temperature.

As a reference control, the EDTA stabilized blood sample (collected in K2 EDTA tubes without further additives) was also stored for 3 and 6 days. Furthermore, where indicated in the examples, a stabilization solution comprising a caspase inhibitor and N,N-dimethylacetamide (DMAA) was included in the comparison (final concentration in the mixture that is obtained when adding said stabilization solution to the blood sample: 7.2 mg/ml K2 EDTA, 1 µM Quinoline-Val-Asp-CH2-OPH (caspase inhibitor) and 5% DMAA) (see unpublished PCT/EP2012/070211 and PCT/EP2012/068850). DMAA stabilized samples as tested herein always included additionally a caspase inhibitor. No DMAA containing stabilizing solutions without caspase inhibitor were tested in the subsequent examples.

Extracellular Nucleic Acid Isolation And Analysis

Plasma was generated from the stabilized and unstabilized (EDTA) blood samples by inverting the blood containing tubes for four times. Then, the tubes were centrifuged for 10 minutes at 1900×g at 4° C. 2.5 ml of the plasma fraction was transferred into a fresh 15 ml falcon tube and centrifuged for 10 minutes at 16.000×g at 4° C. 2 ml of the respectively cleared plasma was used for extracellular nucleic acid Cycle threshholds of the individual samples were translated into amount of gDNA in the eluate, according to a gDNA standard curve. The gDNA amount of the storage time points was compared to the time zero gDNA level from the same donor and is shown as fold increase in the figures. Especially the increase of the 500 bp fragment in the plasma fraction of the blood sample after storage is an indication for a lysis/destruction of white blood cells. Thus, the lower the amount of released 500 bp DNA, the better the performance of the stabilization method.

Results

The figures corresponding to the subsequently described examples show the increase of DNA relative to time point 0 with the different stabilization solutions (fold change) using different amplicon lengths of 18S rRNA gene. Bars indicate the mean of the triplicate samples per condition and test time point.

Example 4

Stabilization Using Formamide Without and With Caspase Inhibitor

In example 4, different concentrations of formamide were used either alone or in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

Stabilization Solutions Without Caspase Inhibitor

The stabilization solutions without the caspase inhibitor comprised formamide in different concentrations and EDTA. When adding these stabilization solutions to the blood sample, the following final concentrations were obtained in the blood/stabilization solution mixture: 7.2 mg/ml K2 EDTA and different concentrations of formamide (see figures for details)

Stabilization Solutions with Caspase Inhibitor

These stabilization solutions comprised formamide in different concentrations, a caspase inhibitor and EDTA. When adding these stabilization solutions to the blood sample, the following final concentrations were obtained in the blood/stabilization solution mixture:

7.2 mg/ml K2 EDTA, 1 µM Quinoline-Val-Asp-CH2-OPH (caspase inhibitor) and different concentrations of formamide (see figures for details).

FIGS. 15 to 18 show the stabilization results obtained for blood from different donors. FIGS. 15 to 18 compare the results that were achieved either with formamide alone or formamide in combination with the caspase inhibitor. As can be seen, formamide alone was in different concentrations effective to stabilize the extracellular nucleic acid population as can be seen from the significantly reduced increase in 18S rDNA in formamide stabilized samples.

However, variations in the stabilization effectivity were seen between different donors. Such variations did not occur when using a caspase inhibitor in addition to formamide. Therefore, it is preferred to use formamide in combination with a caspase inhibitor.

Figure 19:
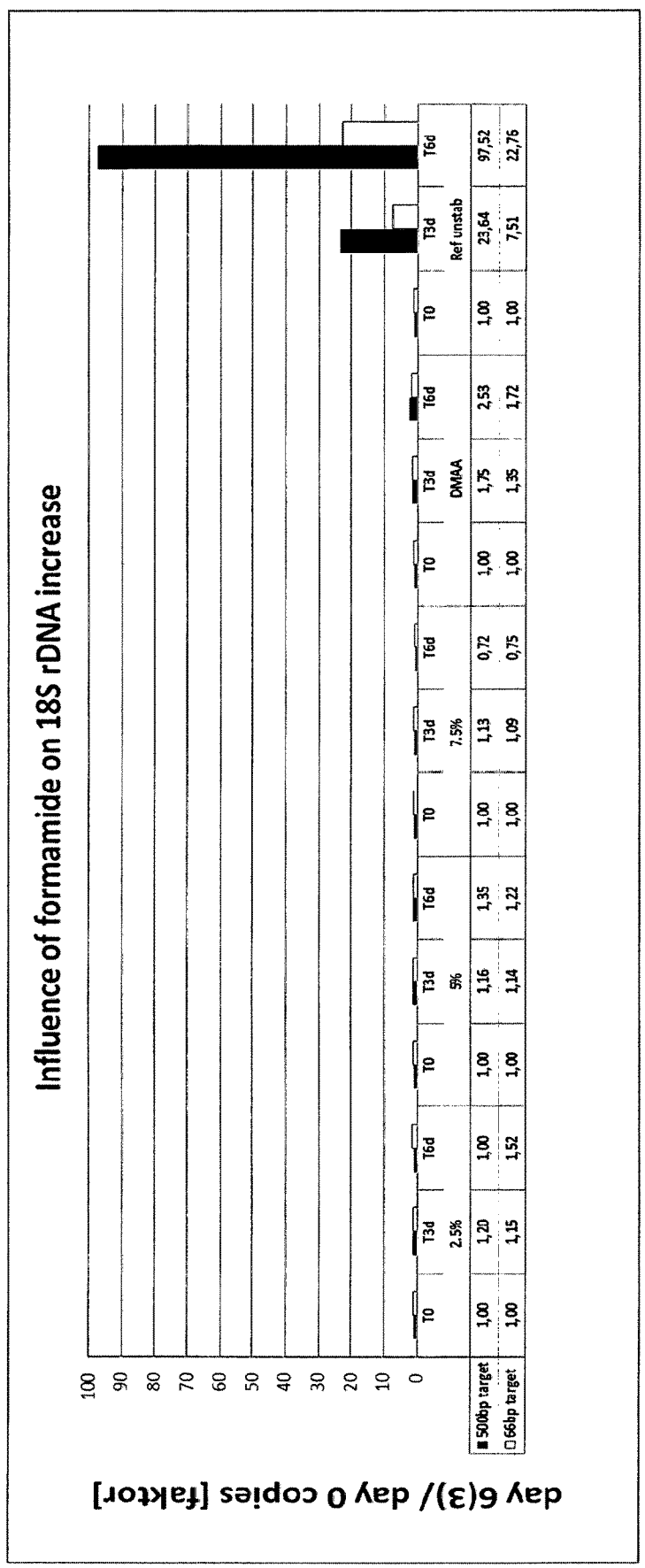
Figure 20:
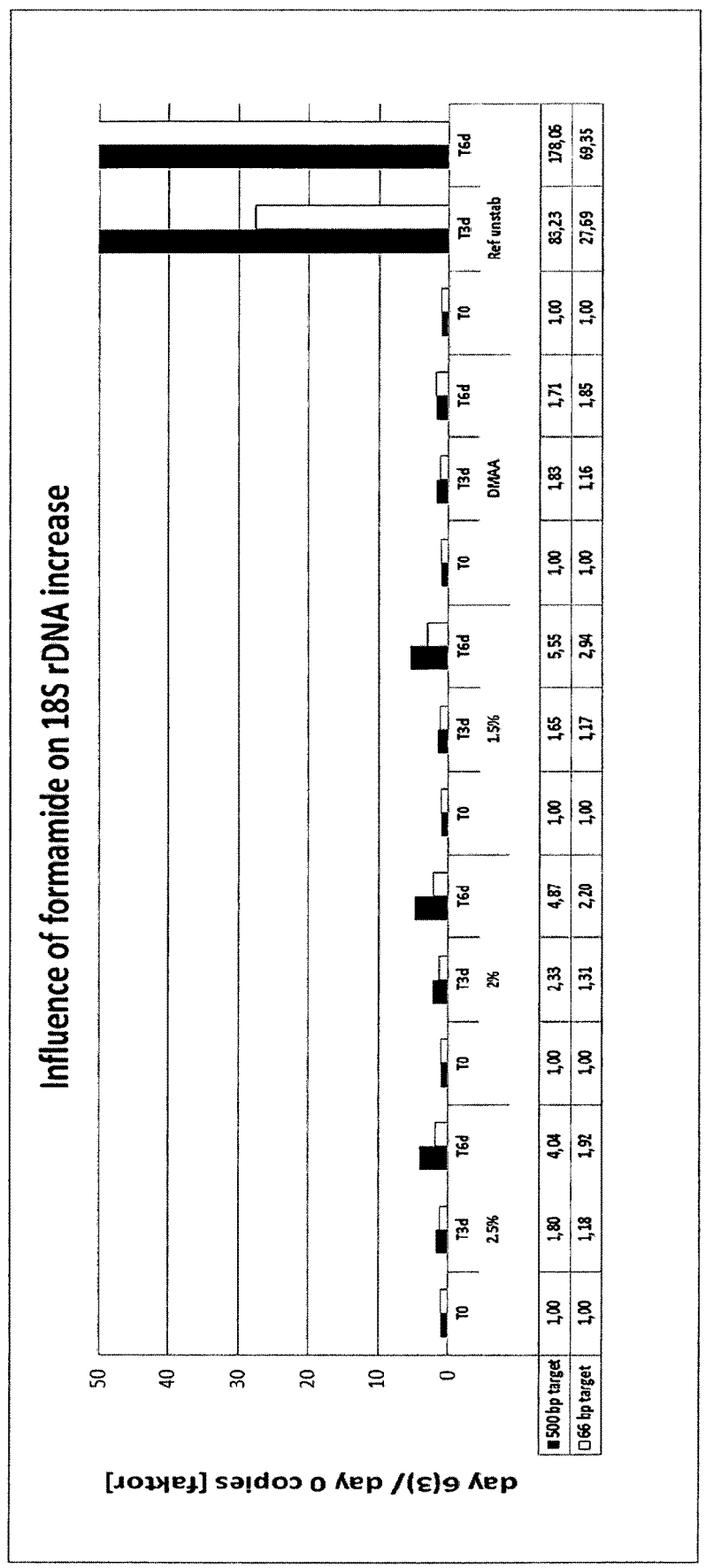
Figure 21:
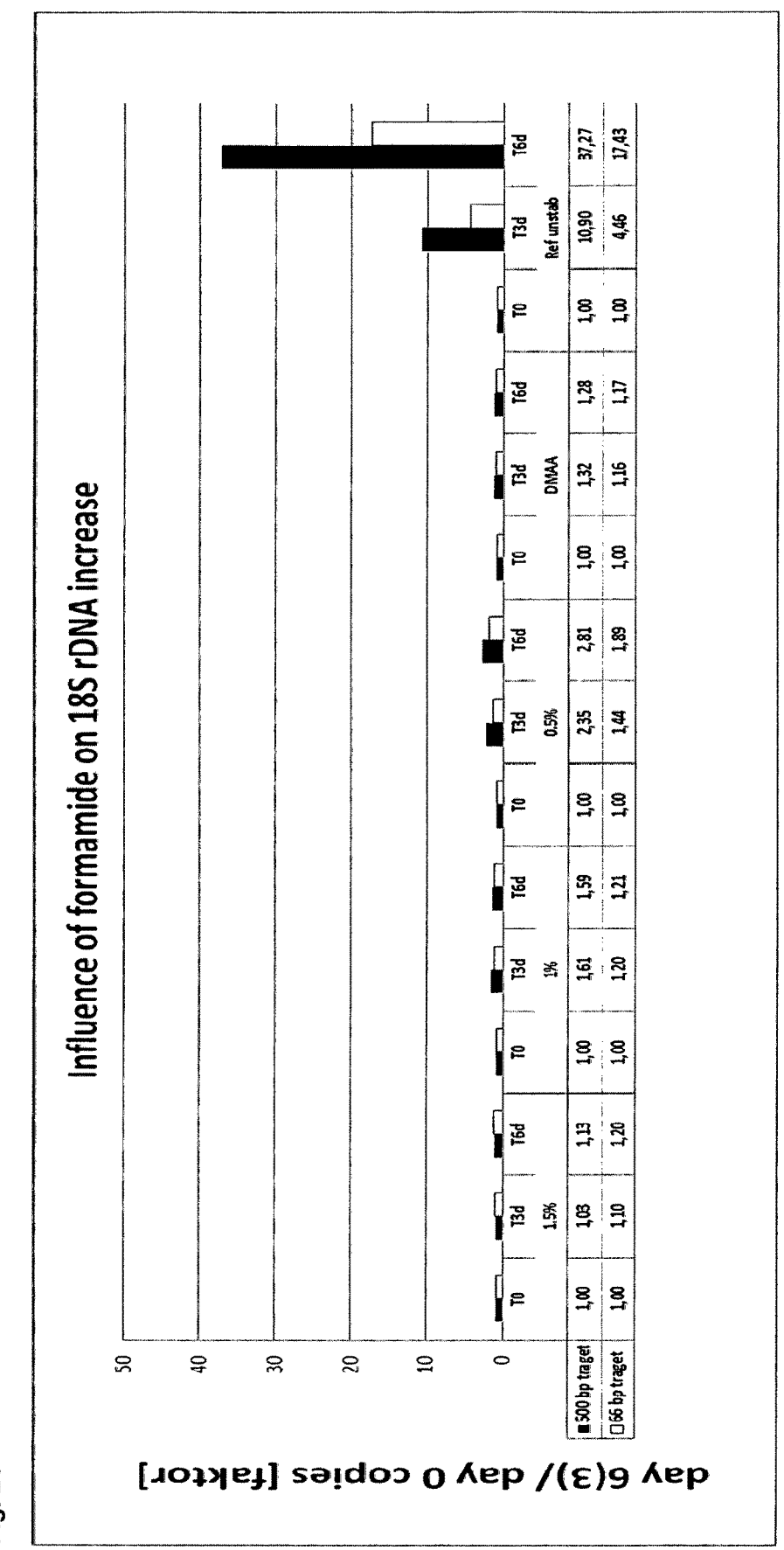

FIGS. 19 to 21 show the stabilization results obtained for blood from different donors wherein the blood samples were stabilized with formamide in different concentrations (see figures for details) in combination with a caspase inhibitor. Therefore, the stabilization solutions used comprised formamide and the caspase inhibitor. As can be seen, uniform stabilization results were obtained with various concentrations of formamide.

Example 5

Stabilization Using Acetamide with Caspase Inhibitor

In example 5, different concentrations of acetamide were used in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

The stabilization solutions comprised acetamide in different concentrations, a caspase inhibitor and EDTA. When adding these stabilization solutions to the blood sample, the following final concentrations were obtained in the blood/stabilization solution mixture:

7.2 mg/ml K2 EDTA, 1 µM Quinoline-Val-Asp-CH2-OPH (caspase inhibitor) and different concentrations of acetamide (see figures for details).

Figure 22:
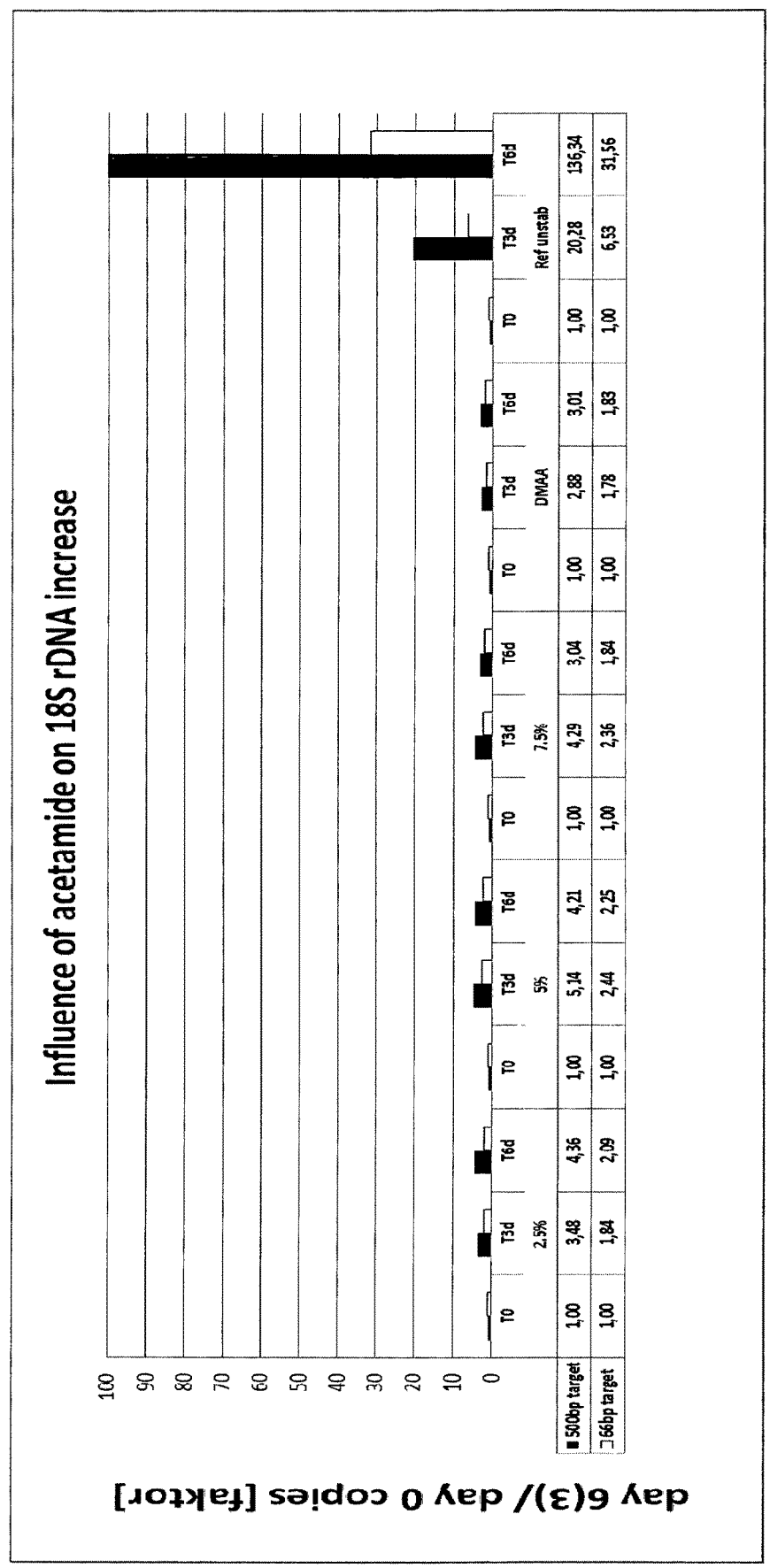
FIGS. 22 to 23: Stabilization of the extracellular nucleic acid population using acetamide in different concentrations in combination with a caspase inhibitor.
Figure 23:
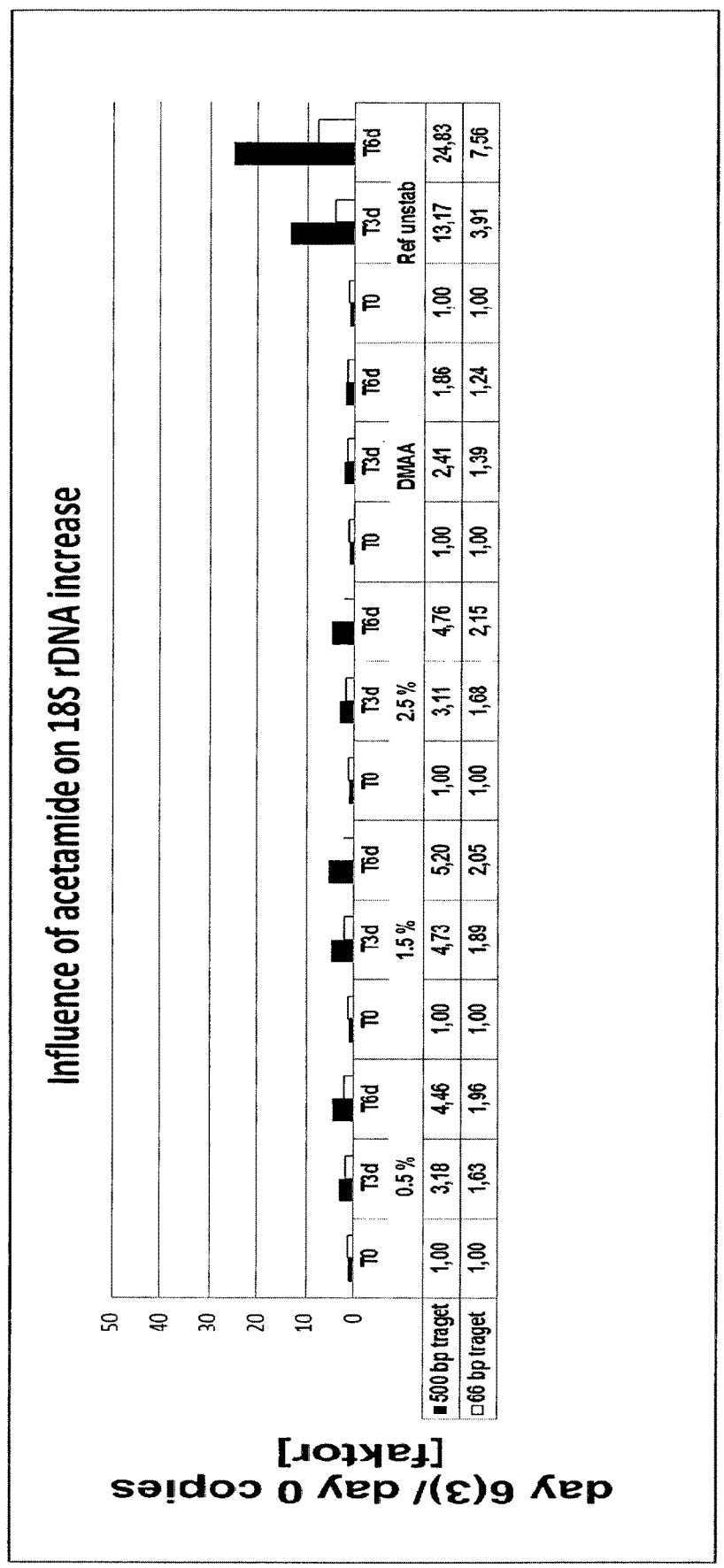

FIGS. 22 and 23 show the stabilization results obtained for blood from different donors wherein the blood samples were stabilized with acetamide in different concentrations (see figures for details) and a caspase inhibitor. As can be seen, the tested stabilization compositions comprising acetamide in different concentrations were effective to stabilize the extracellular nucleic acid population as can be seen from the significantly reduced increase in 18S rDNA in the acetamide stabilized samples.

Example 6

Stabilization Using Propanamide with Caspase Inhibitor

In example 6, different concentrations of propanamide were used in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

The stabilization solutions comprised propanamide in different concentrations, a caspase inhibitor and EDTA. When adding these stabilization solutions to the blood sample, the following final concentrations were obtained in the blood/stabilization solution mixture:

7.2 mg/ml K2 EDTA, 1 µM Quinoline-Val-Asp-CH2-OPH (caspase inhibitor) and different concentrations of propanamide (see figures for details).

Figure 24:
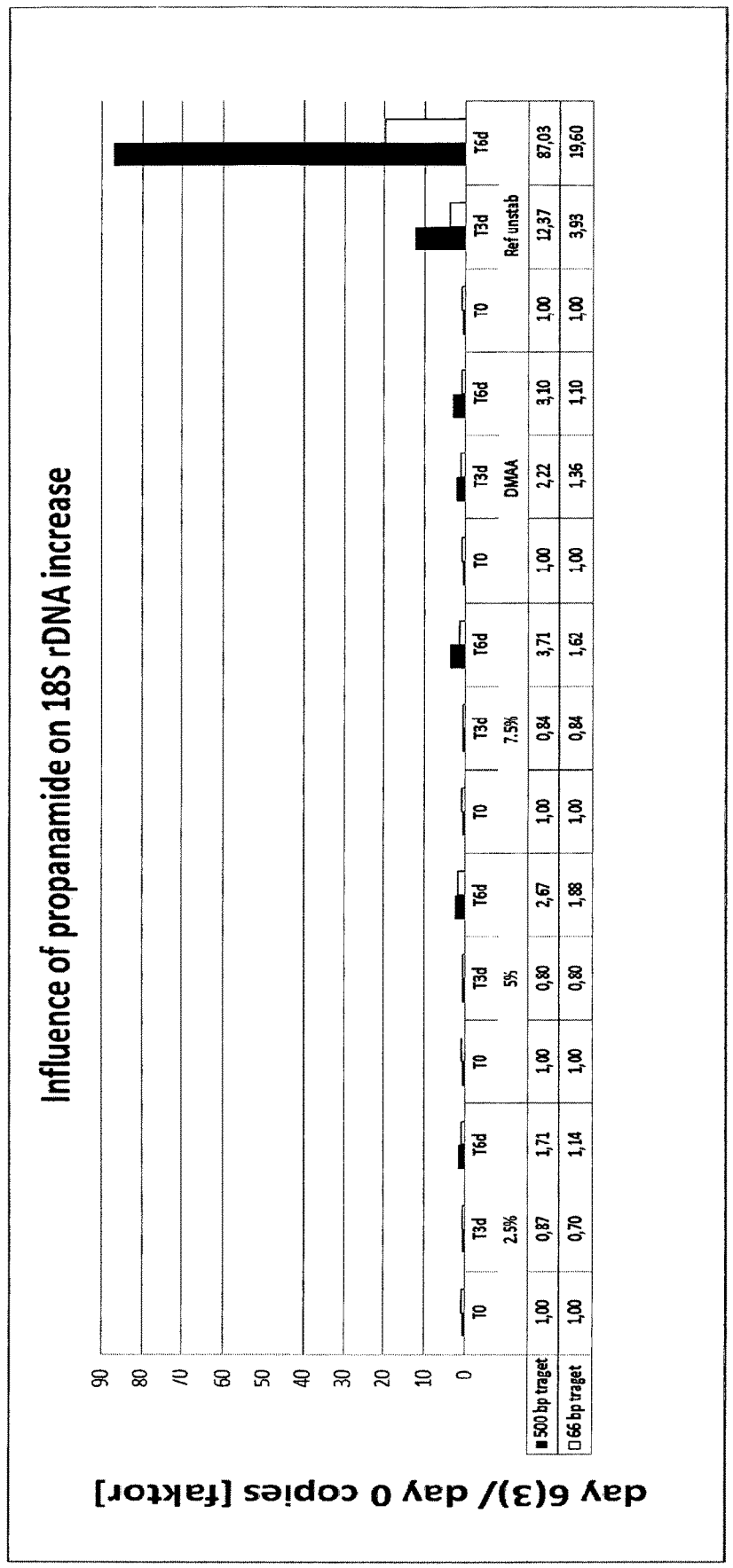
FIG. 24: Stabilization of the extracellular nucleic acid population using propanamide in different concentrations in combination with a caspase inhibitor.

FIG. 24 shows the stabilization results obtained when blood was stabilized with propanamide in different concentrations (see figure for details) and a caspase inhibitor. As can be seen, the tested stabilization compositions comprising propanamide were in different concentrations effective to stabilize the extracellular nucleic acid population as can be seen from the significantly reduced increase in 18S rDNA in the propanamide stabilized samples.

Example 7

Stabilization Using Butanamide Without and With Caspase Inhibitor

In example 7, different concentrations of butanamide were used either alone or in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

Stabilization Solutions Without Caspase Inhibitor

The stabilization solutions without the caspase inhibitor comprised butanamide in different concentrations and EDTA. When adding these stabilization solutions to the blood sample, the following final concentrations were obtained in the blood/stabilization solution mixture:

7.2 mg/ml K2 EDTA and different concentrations of butanamide (see figures for details)

Stabilization Solutions With Caspase Inhibitor

These stabilization solutions comprised butanamide in different concentrations, a caspase inhibitor and EDTA. When adding these stabilization solutions to the blood sample, the following final concentrations were obtained in the blood/stabilization solution mixture:

7.2 mg/ml K2 EDTA, 1 µM Quinoline-Val-Asp-CH2-OPH (caspase inhibitor) and different concentrations of butanamide (see figures for details).

Figure 25:
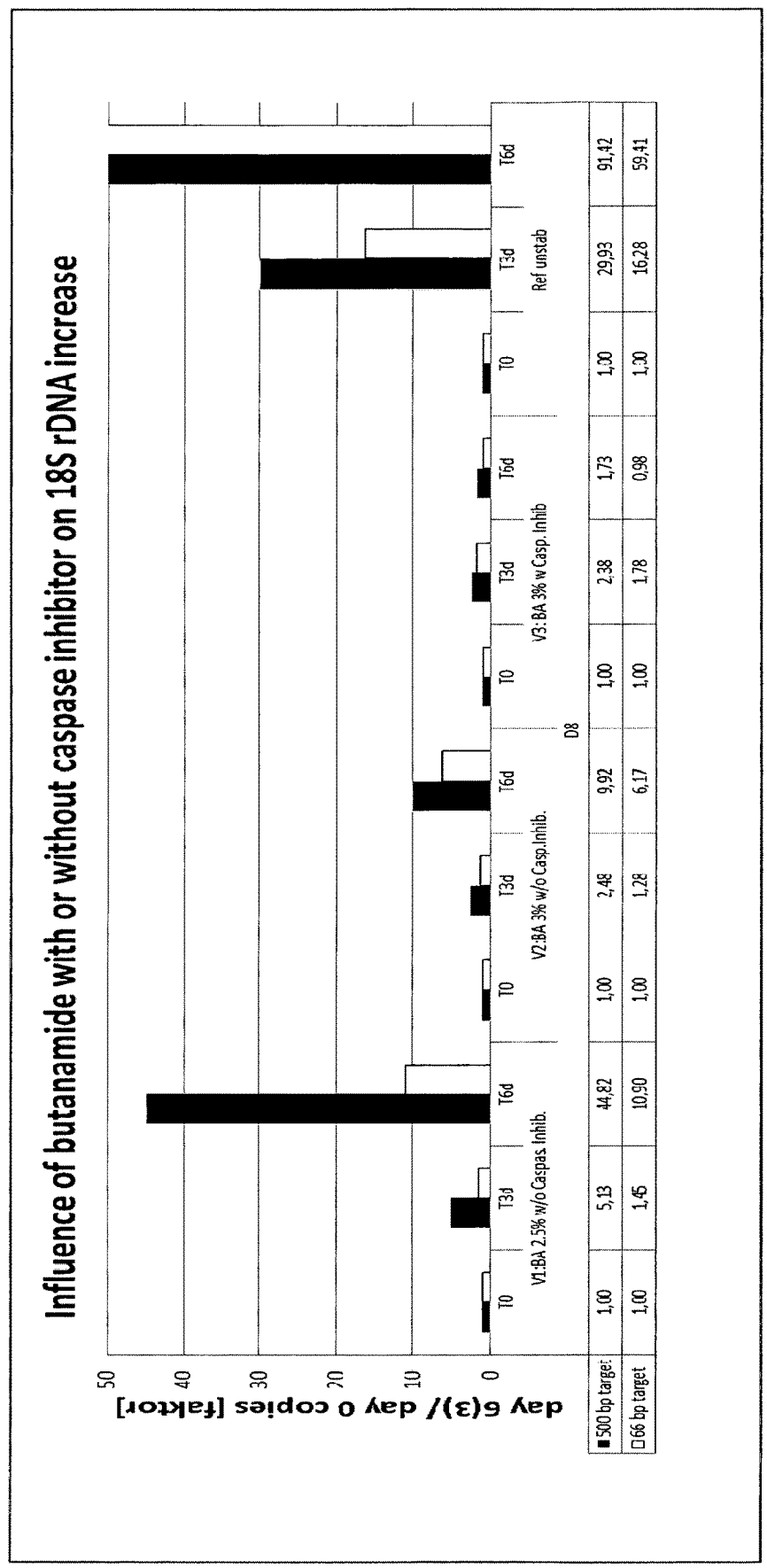
FIGS. 25 to 29: Stabilization of the extracellular nucleic acid population using butanamide in different concentrations either alone or in combination with a caspase inhibitor.
Figure 26:
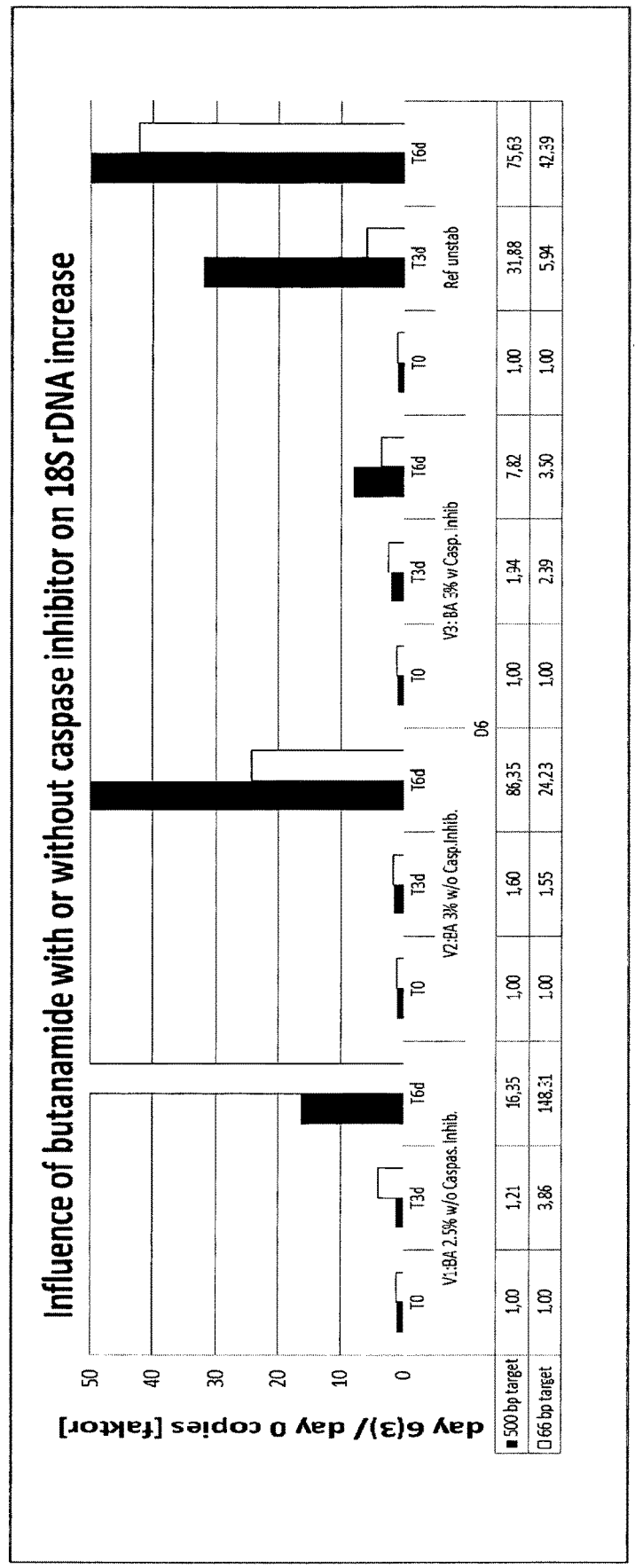
Figure 27:
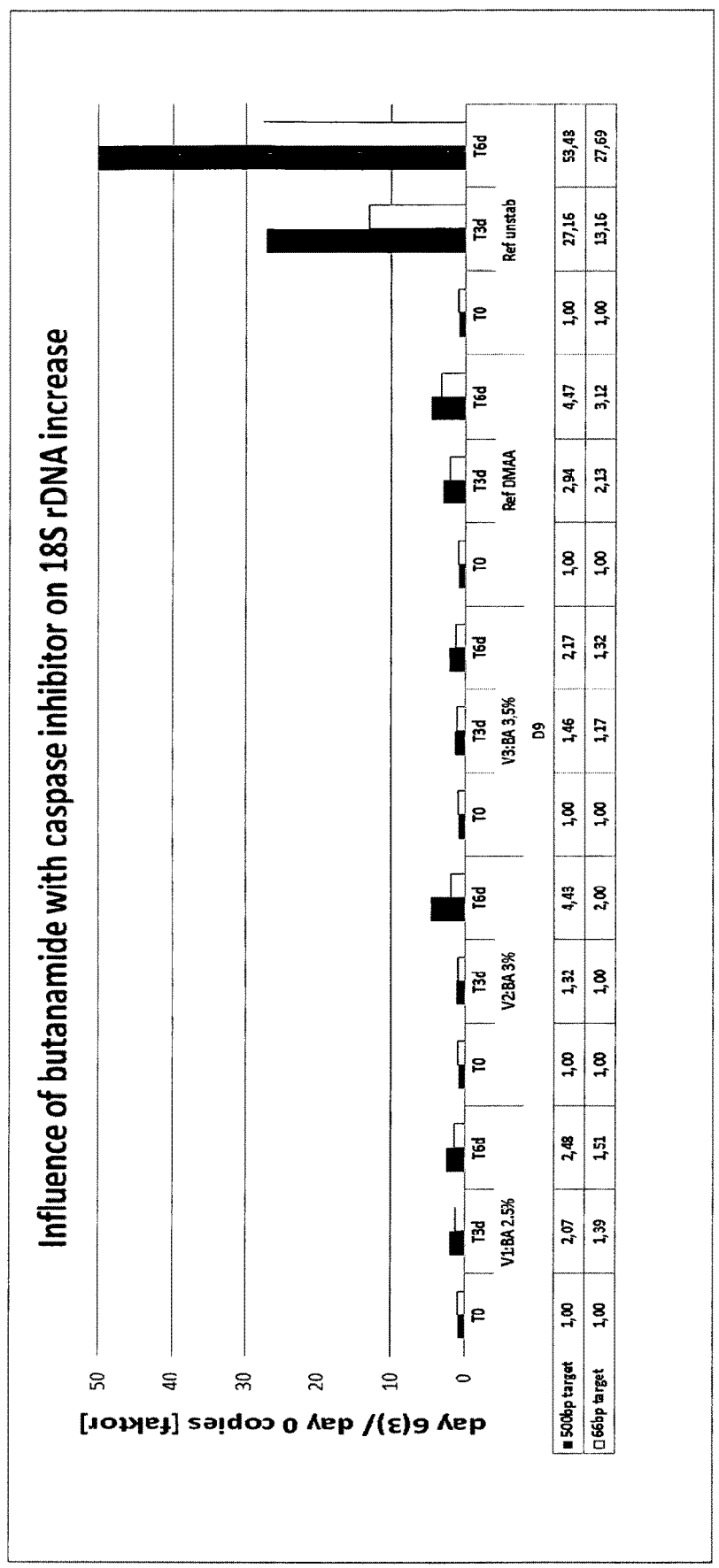
Figure 28:
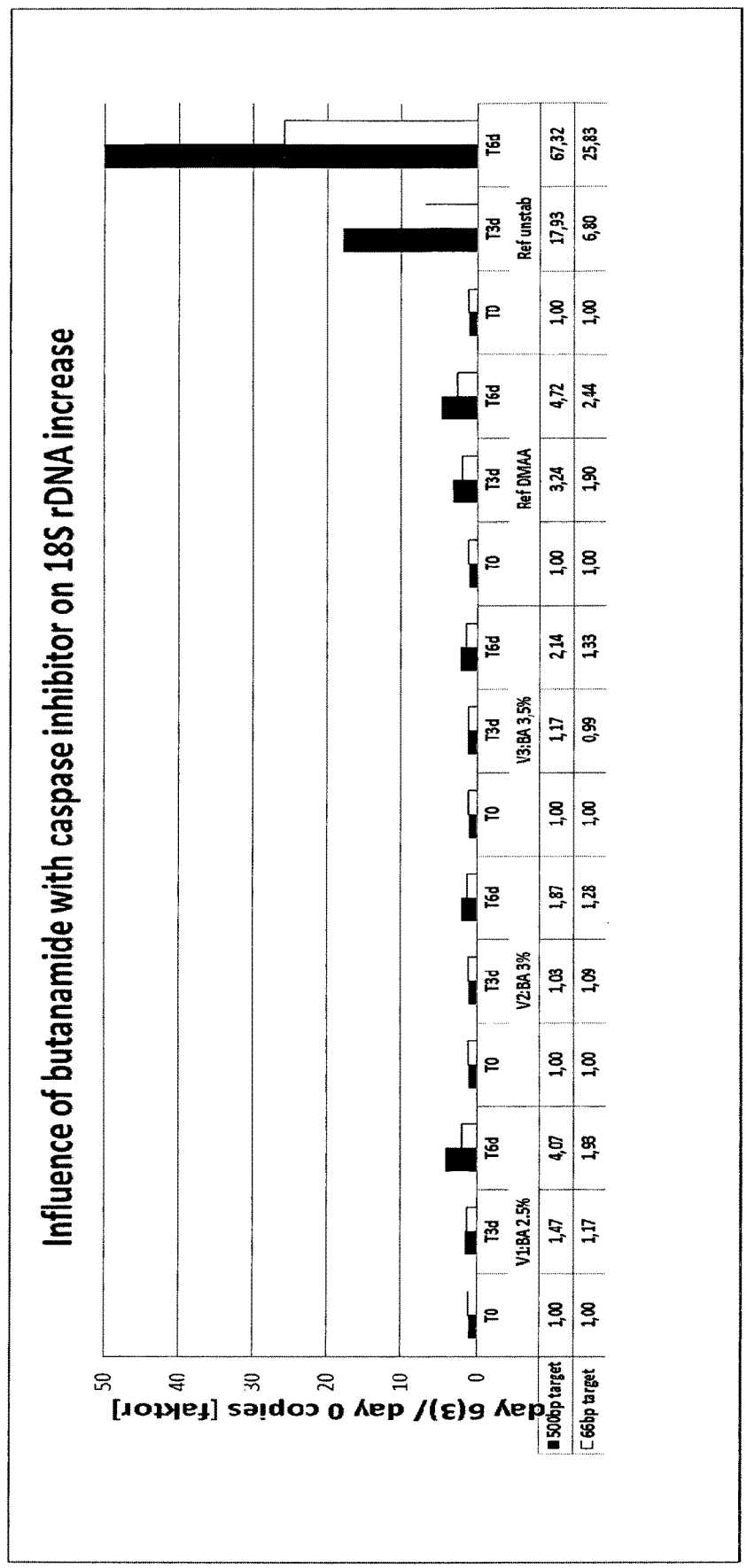
Figure 29:
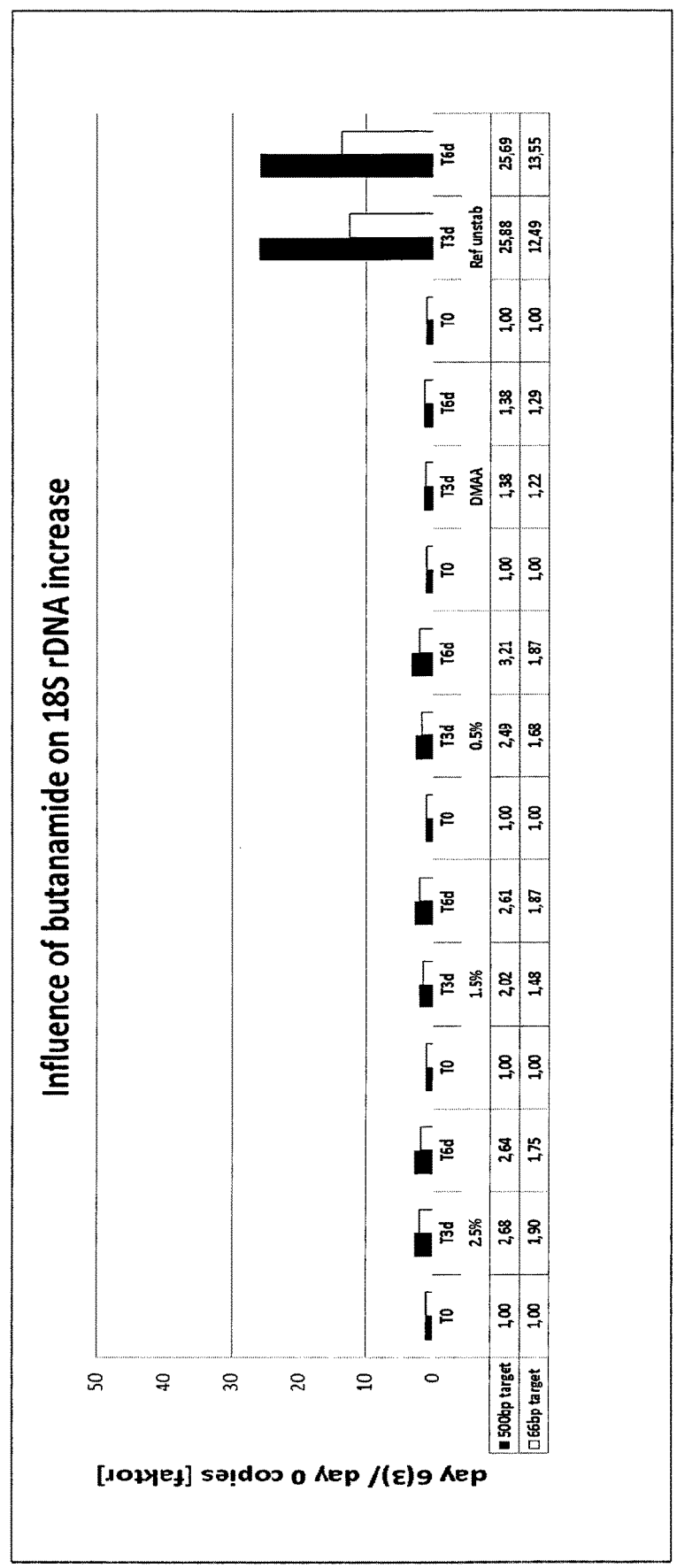

FIGS. 25 to 29 show the stabilization results obtained for blood from different donors using stabilization solutions comprising butanamide. FIGS. 25 and 26 compare the results that were achieved either with butanamide alone or butanamide in combination with the caspase inhibitor. As can be seen, butanamide alone was in different concentrations effective to stabilize the extracellular nucleic acid population as can be seen from the significantly reduced increase in 18S rDNA in butanamide stabilized samples. However, variations in the stabilization effectivity were seen between different donors. Such variations did not occur when using a caspase inhibitor in addition to butanamide. Therefore, it is preferred to use butanamide in combination with a caspase inhibitor. FIGS. 27 to 29 show the stabilization results obtained for blood from different donors wherein the blood samples were stabilized with butanamide in different concentrations (see figures for details) in combination with a caspase inhibitor. Therefore, the stabilization solutions used comprised formamide and the caspase inhibitor.

As can be seen, uniform stabilization results were obtained with various concentrations of butanamide.

Example 8

Stabilization using N-Methylformamide with Caspase Inhibitor

In example 8, different concentrations of N-methylformamide were used in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

The stabilization solutions comprised N-methylformamide in different concentrations, a caspase inhibitor and EDTA. When adding these stabilization solutions to the blood sample, the following final concentrations were obtained in the blood/stabilization solution mixture:

7.2 mg/ml K2 EDTA, 1 μM Quinoline-Val-Asp-CH2-OPH (caspase inhibitor) and different concentrations of N-methylformamide (see figures for details).

Figure 30:
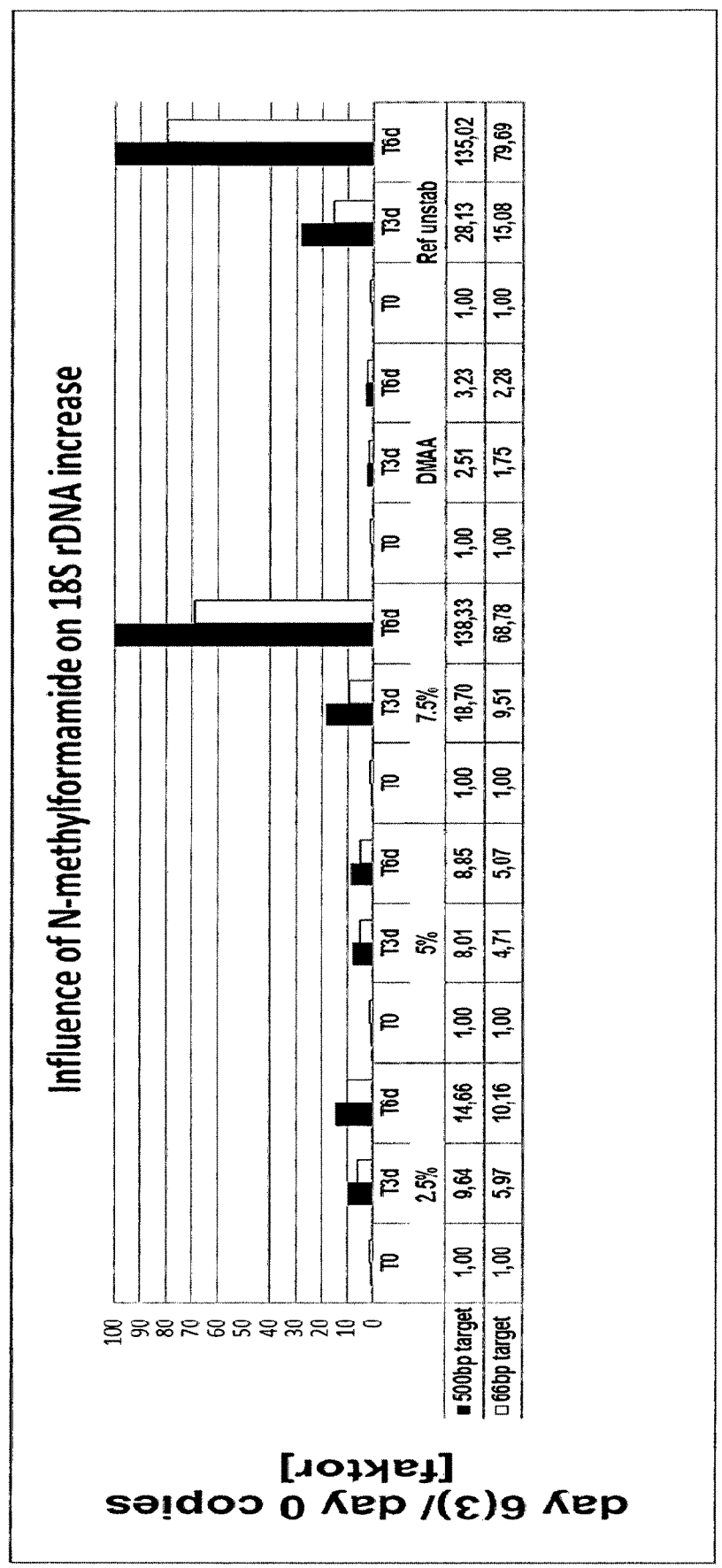
FIG. 30: Stabilization of the extracellular nucleic acid population using N-methylformamide in different concentrations in combination with a caspase inhibitor.

FIG. 30 shows the stabilization results obtained when blood was stabilized with N-methylformamide in different concentrations (see figure for details) and a caspase inhibitor. As can be seen, the tested stabilization compositions comprising N-methylformamide were in different concentrations effective to stabilize the extracellular nucleic acid population as can be seen from the significantly reduced increase in 18S rDNA in the N-methylformamide stabilized samples.

Example 9

Stabilization Using N-Methylacetamide With Caspase Inhibitor

In example 9, different concentrations of N-methylacetamide were used in combination with a caspase inhibitor for stabilizing blood samples. The focus of the analysis was the stabilization of the extracellular nucleic acid population as determined by analyzing the increase of 18S rDNA. Stabilization and processing of the samples were performed as described in materials and methods under II.

The stabilization solutions comprised N-methylacetamide in different concentrations, a caspase inhibitor and EDTA. When adding these stabilization solutions to the blood sample, the following final concentrations were obtained in the blood/stabilization solution mixture:

7.2 mg/ml K2 EDTA, 1 μM Quinoline-Val-Asp-CH2-OPH (caspase inhibitor) and different concentrations of N-methylacetamide (see figures for details).

Figure 31:
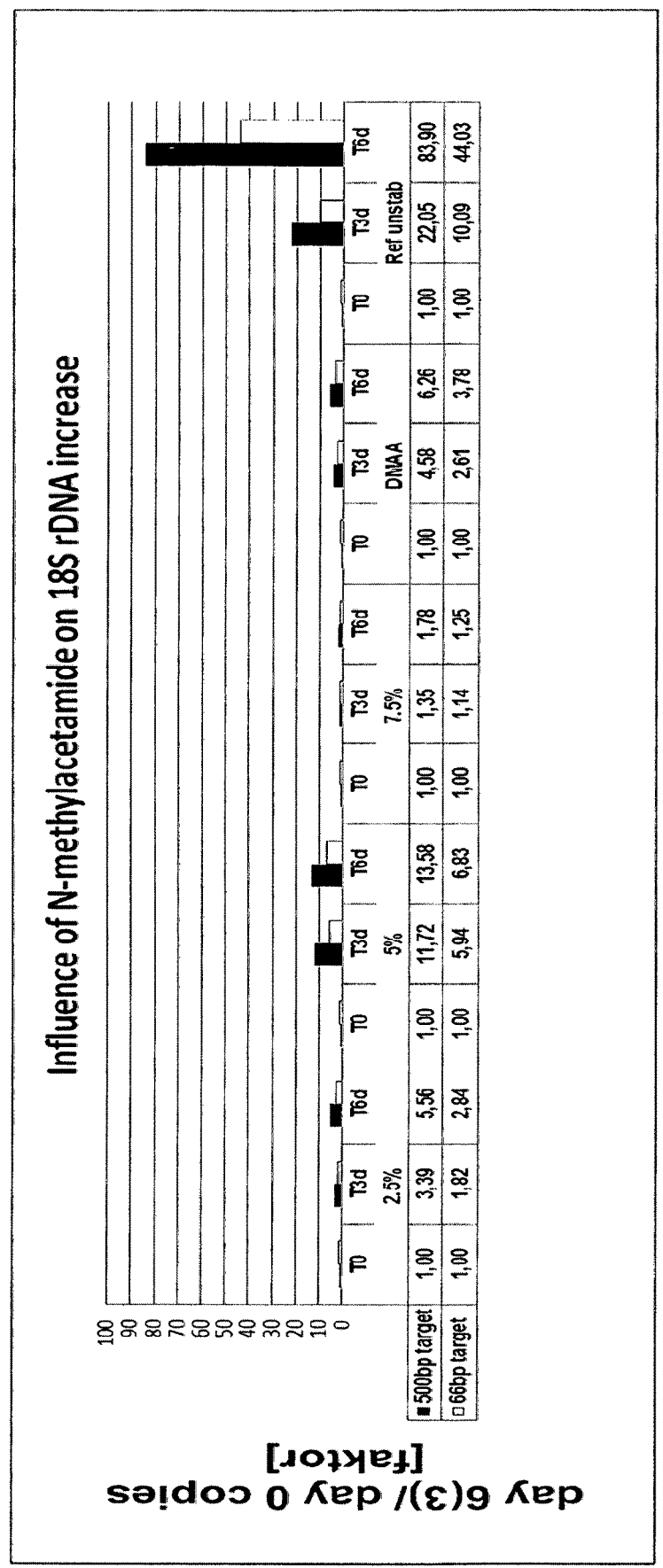
FIG. 31: Stabilization of the extracellular nucleic acid population using N-methylacetamide in different concentrations in combination with a caspase inhibitor.

FIG. 31 shows the stabilization results obtained when blood was stabilized with N-methylacetamide in different concentrations (see figure for details) and a caspase inhibitor. As can be seen, the tested stabilization compositions comprising N-methylacetamide were in different concentrations effective to stabilize the extracellular nucleic acid population as can be seen from the significantly reduced increase in 18S rDNA in the N-methylacetamide stabilized samples.

Examples 4 to 9 demonstrate that stabilizing solutions according to the present invention which accordingly comprise primary or secondary carboxylic acid amides show significantly lower amounts of released DNA after storage for 3 days at room temperature compared to unstabilized EDTA blood. As can be seen, all tested stabilizing agents achieved a stabilizing effect on the extracellular nucleic acid population for at least three days. Furthermore, for many stabilization solutions a stabilization effect of up to 6 days and longer was observed. Furthermore, the examples show that the stabilizing effect could be improved with all tested carboxylic acid amides when they were used in combination with a caspase inhibitor. Stabilization solutions which additionally comprised a caspase inhibitor achieved a prolonged stabilization effect for at least 6 days. Furthermore, when testing the stabilization solutions of the inventions on blood samples obtained from a plurality of different donors, it was found that the stabilization effect that is achieved with the combination of a primary or secondary carboxylic acid amide and a caspase inhibitor showed less variations in the achieved stabilization effect. Therefore, the stabilization was significantly improved when using these carboxylic acid amides in combination with a caspase inhibitor.

The invention claimed is:

1. A method for stabilizing a cell-containing biological sample, comprising:
 a) contacting the sample with
  (i) at least one carboxylic acid amide,
   wherein the carboxylic acid amide is selected from primary carboxylic acid amides and secondary carboxylic acid amides having formula 1

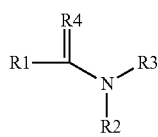

formula 1 wherein R1 is hydrogen or C1-05 alkyl, wherein R2 is hydrogen or C1-05 alkyl, wherein R3 is hydrogen, and wherein R4 is oxygen, and
  (ii) a caspase inhibitor,
 wherein the cell-containing biological sample is selected from the group consisting of body fluids, body secretions, body excretions, swab samples, and animal cell-containing biological samples,
 wherein said method is not based on cell lysis, and
 wherein the stabilization does not involve the use of a cross-linking agent that induces protein-nucleic acid and/or protein-protein crosslinks, the use of a formaldehyde releaser, or freezing the sample.

2. The method according to claim 1, wherein the stabilization results in a stabilization of intracellular RNA, and/or wherein the extracellular nucleic acid population comprised in the cell-containing sample is stabilized.

3. The method according to claim 1, having one or more of the following characteristics:
 a) the method comprises contacting the cell-containing sample with at least one primary carboxylic acid amide selected from the group consisting of formamide, acetamide, propanamide and butanamide;
 b) the method comprises contacting the cell-containing sample with butanamide;
 c) the method comprises contacting the cell-containing sample with at least one secondary carboxylic acid amide selected from the group consisting of N-alkylformamide, N-alkylacetamide and N-alkylpropanamide; or d) the method comprises contacting the cell-containing sample with at least one secondary carboxylic acid amide selected from N-methylformamide, N-methylacetamide and N-methylpropanamide.

4. The method according to claim 1, wherein the mixture that is obtained when contacting the cell-containing biological sample with the at least one carboxylic acid amide selected from primary carboxylic acid amides and secondary carboxylic acid amides comprises said carboxylic acid amide in a concentration of at least 0.1%, at least 0.25%, at least 0.5%, at least 0.75%, at least 1%, at least 1.25%, at least 1.5% or at least 2%.

5. The method according to claim 1, wherein the cell-containing sample is a blood sample, and the method comprises additionally contacting the blood sample with an anticoagulant.

6. The method according to claim 1, having one or more of the following characteristics:
   a) performing the method reduces the degradation of nucleic acids present in the cell-containing sample due to the stabilization;
   b) performing the method stabilizes intracellular RNA of the cell-containing biological sample;
   c) performing the method stabilizes the transcriptome and/or transcript levels in cells contained in the sample; and/or
   d) performing the method stabilizes the transcriptome and/or transcript levels in cells contained in the sample, wherein the transcript level of one or more marker genes selected from c-fos, IL-1beta, IL-8 and p53 is stabilized for at least 24h or at least 48h upon stabilization.

7. The method according to claim 1, wherein the method is suitable for stabilizing an extracellular nucleic acid population comprised in the cell-containing sample and wherein the release of genomic DNA from cells contained in the sample into the cell-free portion of the sample is reduced.

8. The method according to claim 1, having one or more of the following characteristics:
   a) the stabilization allows isolating cells from the stabilized sample;
   b) the cell-containing sample is a blood sample and wherein white blood cells are stabilized;
   c) the morphology of cells is preserved;
   d) the morphology of nucleated cells is preserved;
   e) the sample is a blood sample and contained lymphocytes and/or monocytes are stabilized;
   f) cell surface epitopes are preserved; and/or
   g) cell surface proteins are preserved.

9. The method according to claim 1, wherein the method comprises additionally contacting the cell-containing sample with at least one polyethylene glycol.

10. The method according to claim 1, wherein the method has one or more of the following characteristics:
    a) the at least one carboxylic acid amide which is a primary or secondary carboxylic acid amide and optionally further additives are comprised in a stabilising composition and wherein the volumetric ratio of the stabilising composition to the specified volume of the cell-containing sample is selected from 10:1 to 1:20, 5:1 to 1:15, 1:1 to 1:10 and 1:2 to 1:5;
    b) the method comprises subjecting the stabilized cell-containing sample to a nucleic acid analysis and/or detection method;
    c) the method comprises isolating intra- and/or extracellular nucleic acids from the stabilized sample and analyzing and/or detecting the isolated nucleic acids;
    d) the method comprises removing cells comprised in the stabilized sample;
    e) the method comprises storing (i) the stabilized cell-containing biological sample, (ii) the stabilized sample from which cells have been removed and/or (iii) cells removed from the sample; and/or
    f) the method comprises removing cells from the stabilized sample and i) analyzing the removed cells and/or ii) isolating biomolecules from removed cells.

11. The method according to claim 1, wherein the method comprises additionally contacting the cell-containing sample with at least one tertiary amide which is a compound according to formula 1

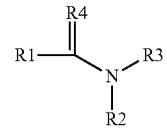

formula 1 wherein R1 is a hydrogen residue or an alkyl residue, wherein R2 and R3 are identical or different hydrocarbon residues with a length of the carbon chain of 1-20 atoms arranged in a linear or branched manner, and wherein R4 is an oxygen, sulphur or selenium residue.

12. The method of claim 1, further comprising:
    b) isolating nucleic acids from the stabilized sample.

13. The method according to claim 12, wherein step b) comprises isolating intracellular RNA.

14. The method according to claim 12, wherein cells are separated from the stabilized sample, and wherein in step b) extracellular nucleic acids are isolated from the remaining sample and/or intracellular nucleic acids are isolated from the removed cells.

15. The method according to claim 1, wherein the cell-containing biological sample is a human body fluid, a human body secretion, a human body excretion, a human swab sample, or a human cell-containing biological sample.

16. The method of claim 1, wherein the cell-containing biological sample is a body fluid.

17. The method of claim 16, wherein the body fluid is blood or urine.

18. The method according to claim 1, wherein in formula 1, R1 is either hydrogen or C1-C5alkyl, R2 is C1-C5 alkyl, R3 is hydrogen, and R4 is oxygen.

19. The method according to claim 1, wherein in formula 1, R1 is either hydrogen or C1-C4 alkyl, R2 is C1-C4 alkyl, R3 is hydrogen, and R4 is oxygen.

20. The method according to claim 1, wherein the caspase inhibitor is Quinoline-Val-Asp-CH2-OPH or Z-Val-Ala-Asp(OMe)-FMK.

* * * * *

UNITED STATES PATENT AND TRADEMARK OFFICE
CERTIFICATE OF CORRECTION

PATENT NO. : 11,525,155 B2  
APPLICATION NO. : 14/777902  
DATED : December 13, 2022  
INVENTOR(S) : Ralf Wyrich et al.

Page 1 of 1

It is certified that error appears in the above-identified patent and that said Letters Patent is hereby corrected as shown below:

In the Claims

Column 121, Claim 1, Line 55:
"C1-05 alky," should read: --C1-C5 alky,--.

Column 121, Claim 1, Line 56:
"C1-05 alky," should read: --C1-C5 alky,--.

Column 124, Claim 18, Line 46:
"C1-C5alky," should read: --C1-C5 alky,--.

Signed and Sealed this
Fourth Day of February, 2025

Coke Morgan Stewart
*Acting Director of the United States Patent and Trademark Office*